(12) United States Patent
Michels et al.

(10) Patent No.: US 9,175,030 B2
(45) Date of Patent: Nov. 3, 2015

(54) DERIVATIVES OF AVICIN D AND METHODS OF MAKING AND USING THEREOF

(71) Applicants: Jordan Gutterman, Houston, TX (US); Valsala Haridas, Houston, TX (US)

(72) Inventors: Peter C. Michels, Albany, NY (US); Yuri L. Khmelnitsky, Albany, NY (US); Jordan Gutterman, Houston, TX (US); Valsala Haridas, Houston, TX (US); Vadim M. Mozhaev, Albany, NY (US)

(73) Assignees: Jordan Gutterman, Houston, TX (US); Valsala Haridas, Houston, TX (US)

( * ) Notice: Subject to any disclaimer, the term of this patent is extended or adjusted under 35 U.S.C. 154(b) by 0 days.

(21) Appl. No.: 14/380,594

(22) PCT Filed: Feb. 22, 2013

(86) PCT No.: PCT/US2013/027362
§ 371 (c)(1),
(2) Date: Aug. 22, 2014

(87) PCT Pub. No.: WO2013/126730
PCT Pub. Date: Aug. 29, 2013

(65) Prior Publication Data
US 2015/0111843 A1    Apr. 23, 2015

Related U.S. Application Data

(60) Provisional application No. 61/602,917, filed on Feb. 24, 2012.

(51) Int. Cl.
*C07H 15/24* (2006.01)
(52) U.S. Cl.
CPC ..................................... *C07H 15/24* (2013.01)

(58) Field of Classification Search
None
See application file for complete search history.

(56) References Cited

U.S. PATENT DOCUMENTS

| | | | |
|---|---|---|---|
| 6,444,233 B1 | 9/2002 | Arntzen et al. | |
| 6,962,720 B2 | 11/2005 | Haridas et al. | |
| 7,105,186 B2 | 9/2006 | Arntzen et al. | |
| 7,670,632 B2 | 3/2010 | Arntzen et al. | |
| 7,985,435 B2 | 7/2011 | Arntzen et al. | |
| 8,324,177 B2 | 12/2012 | Arntzen et al. | |
| 2011/0117008 A1* | 5/2011 | Shastri et al. | ................ 424/1.11 |

FOREIGN PATENT DOCUMENTS

WO    WO 02/055016    7/2002

OTHER PUBLICATIONS

Jayatilake et al., J. Nat. Prod., 2003, 66, pp. 779-783.*
Jayatilake et al., "Isolation and structures of avicins D and G: in vitro tumor-inhibitory saponins derived from *Acacia victoriae*," *J. Nat. Prod.*, 66:779-783, 2003.
PCT International Search Report and Written Opinion issued in International Application No. PCT/US2013/027362, mailed May 31, 2013.

* cited by examiner

*Primary Examiner* — Traviss C McIntosh, III
(74) *Attorney, Agent, or Firm* — Parker Highlander PLLC

(57) ABSTRACT

Disclosed herein are novel oxetane derivatives of avicin D, including compounds of the formula (I), wherein the variables are defined herein. Also provided are pharmaceutical compositions, kits and articles of manufacture comprising these derivative compounds. Methods and intermediates useful for making the derivatives, and methods of using the derivatives and compositions thereof, including for the treatment of cancer, are also provided.

8 Claims, 71 Drawing Sheets

A

B

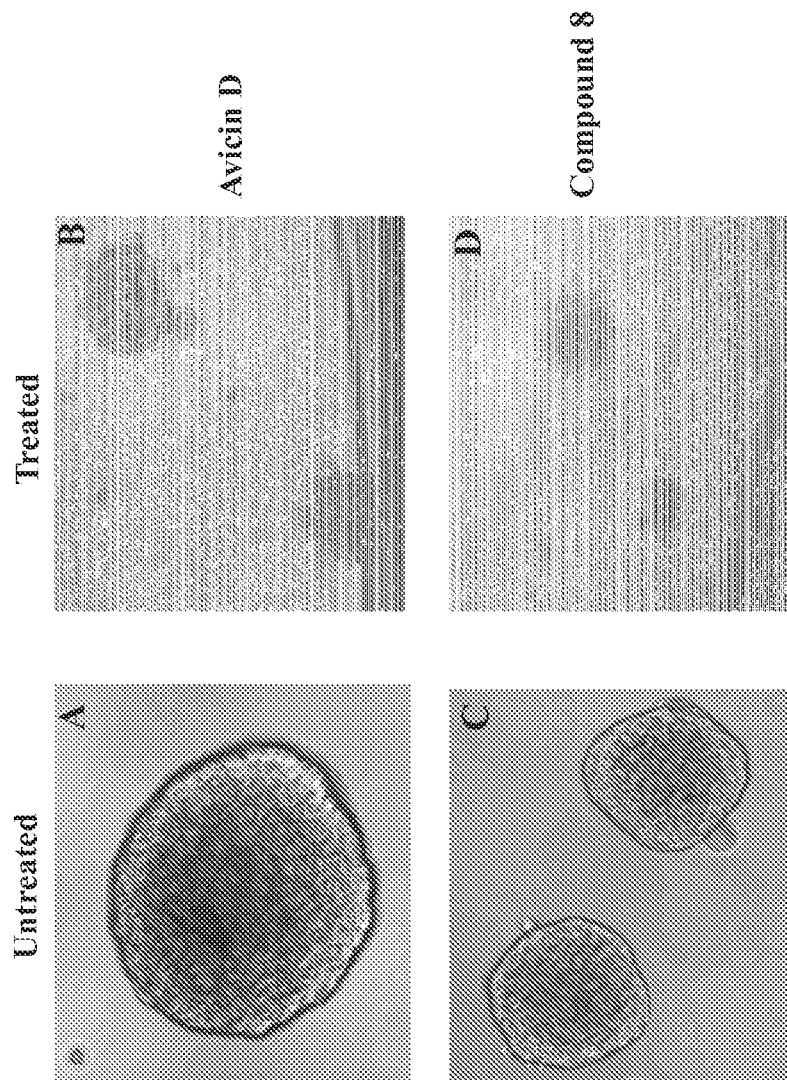
Figures 6A-D

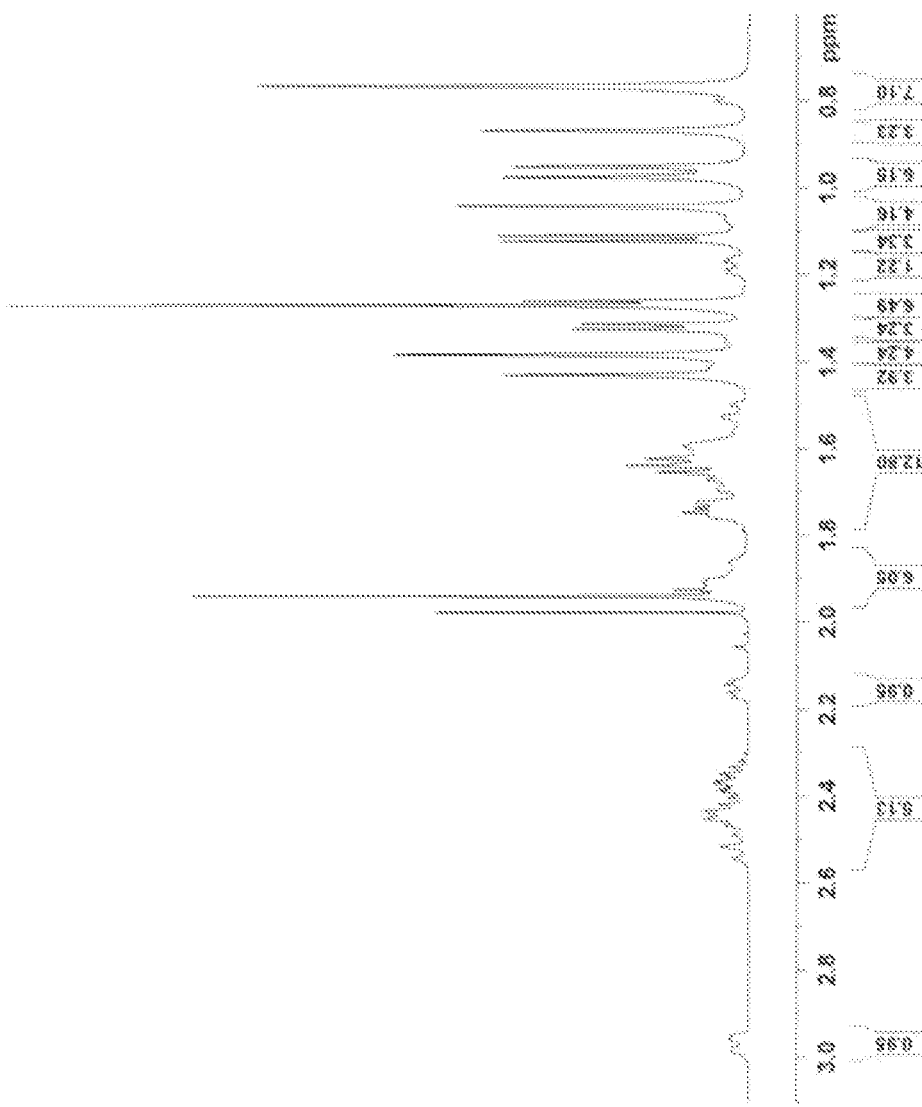

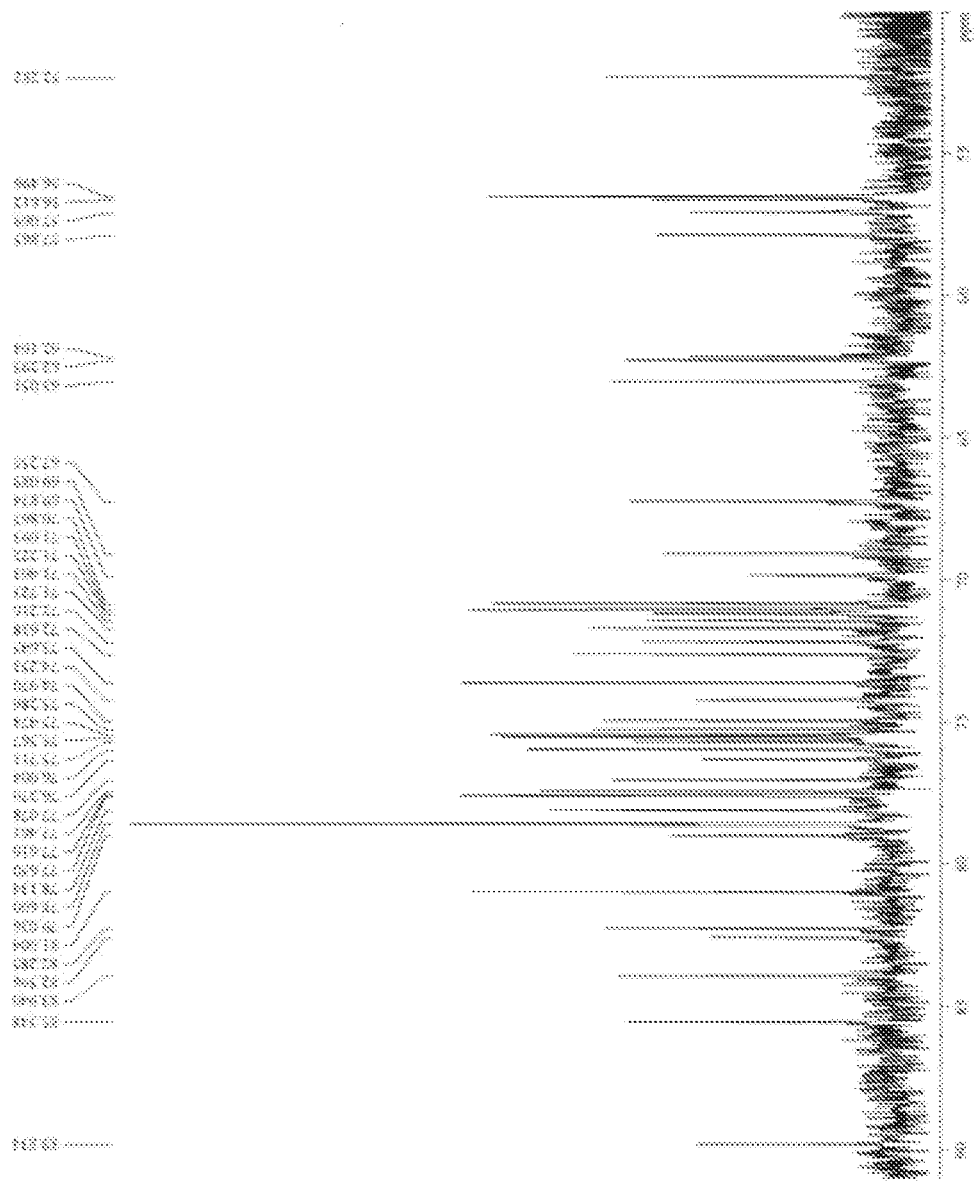

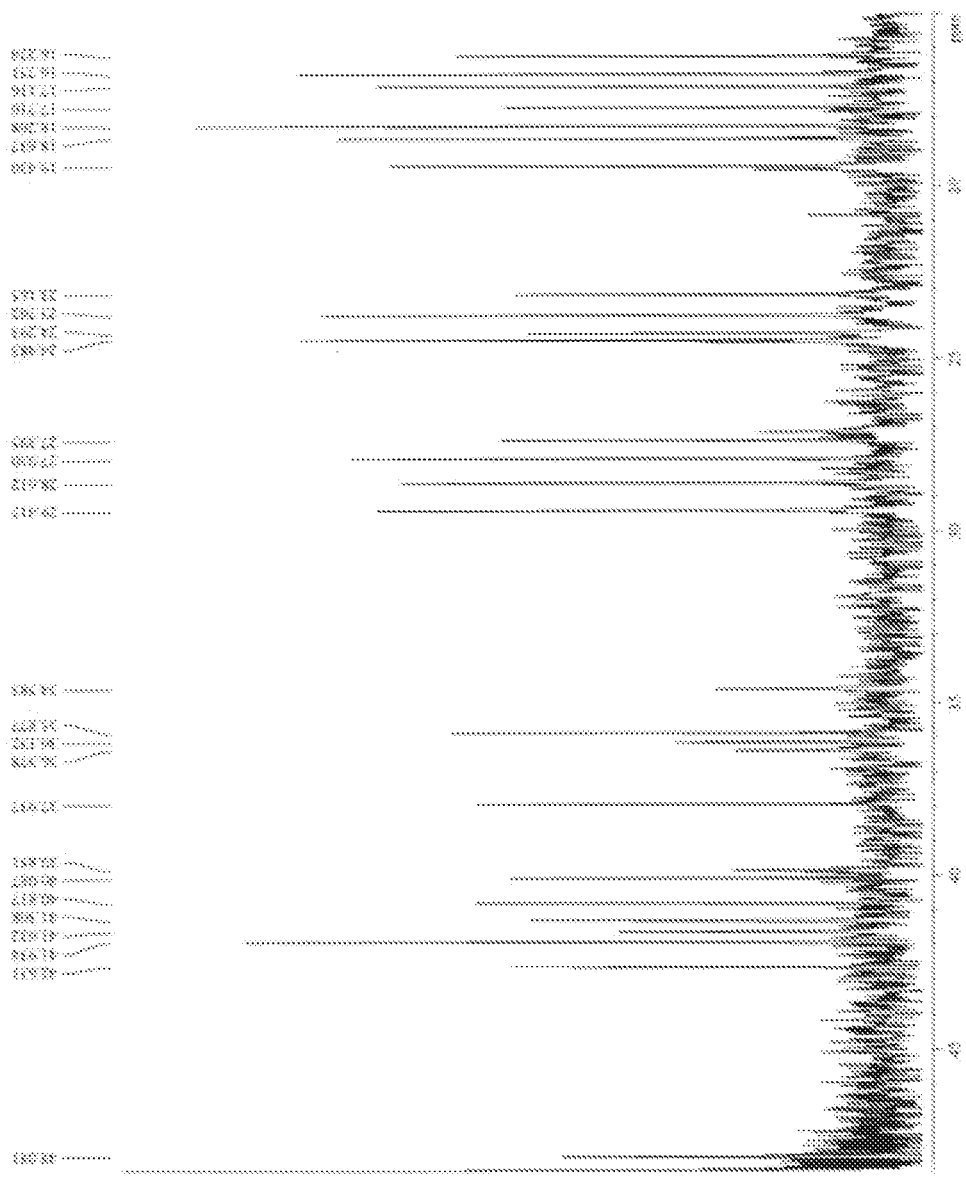

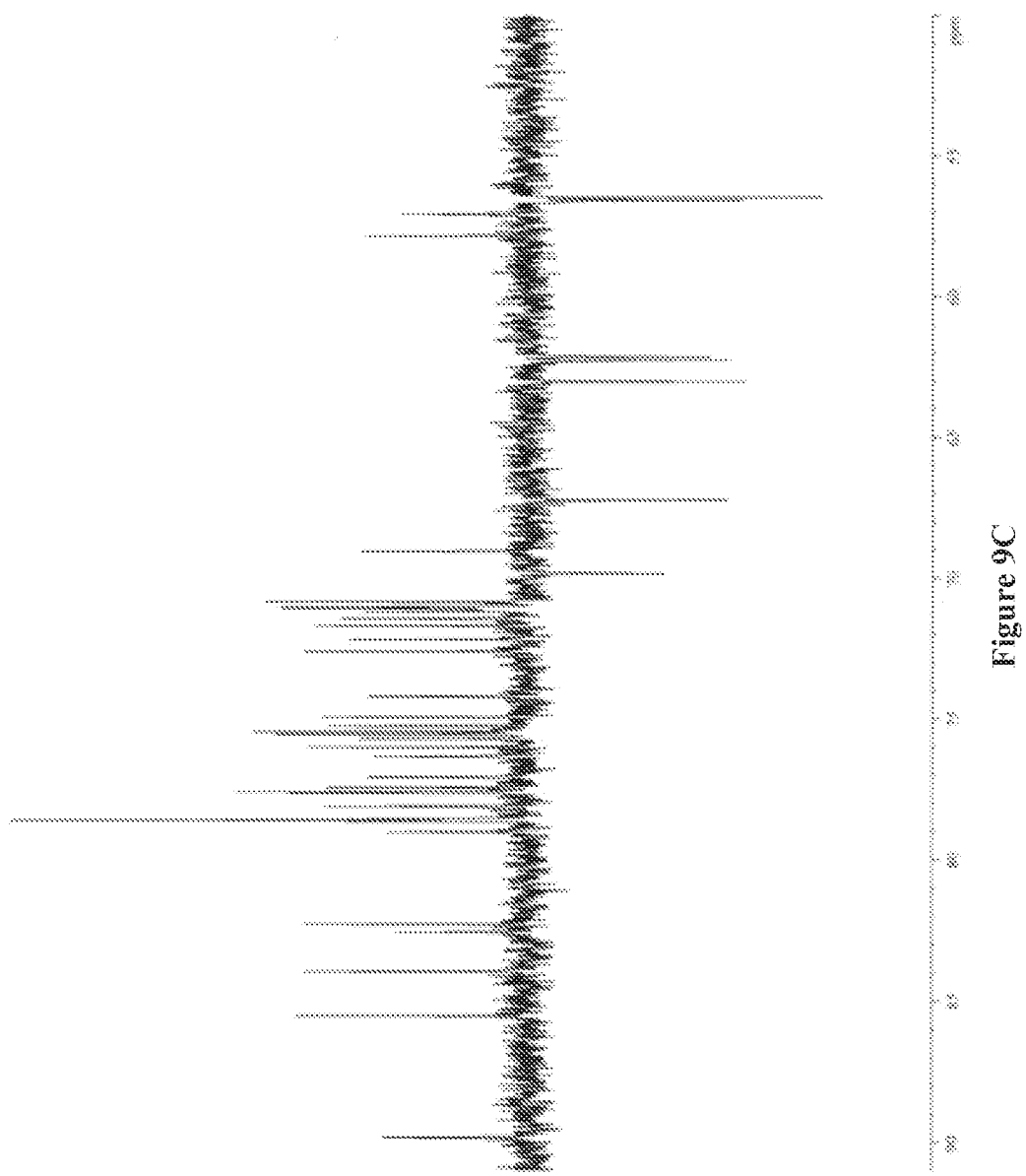

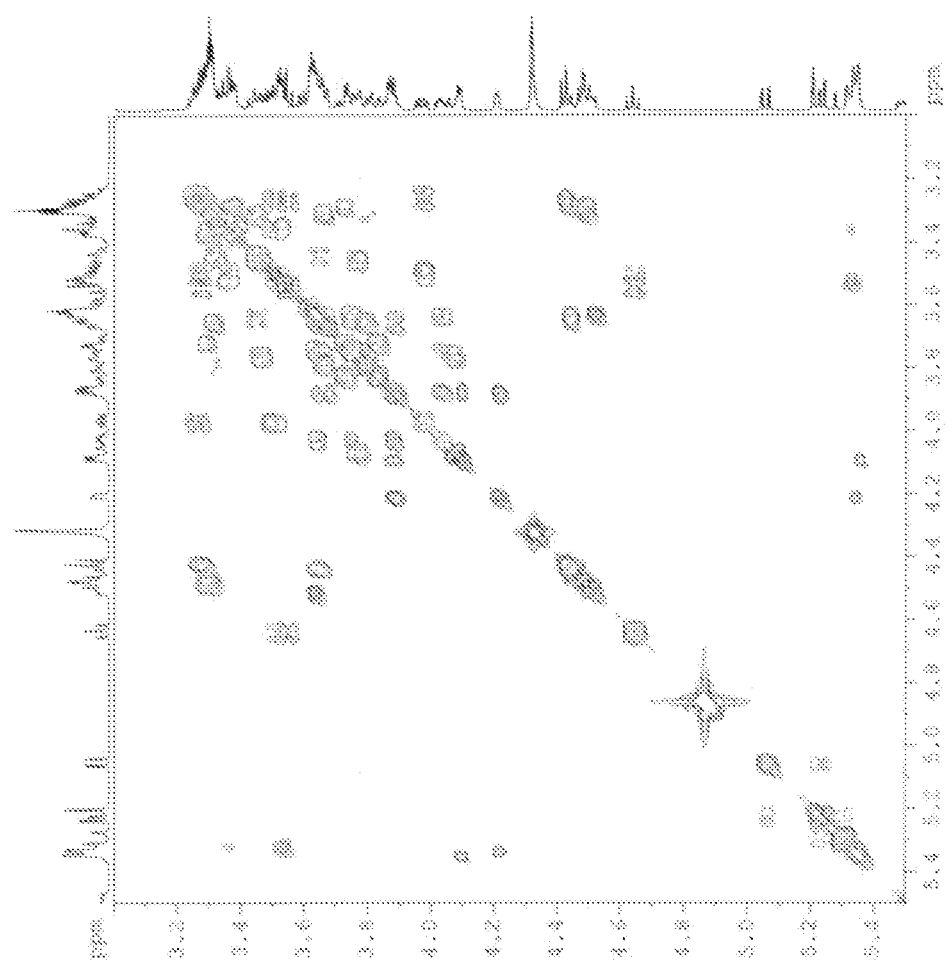

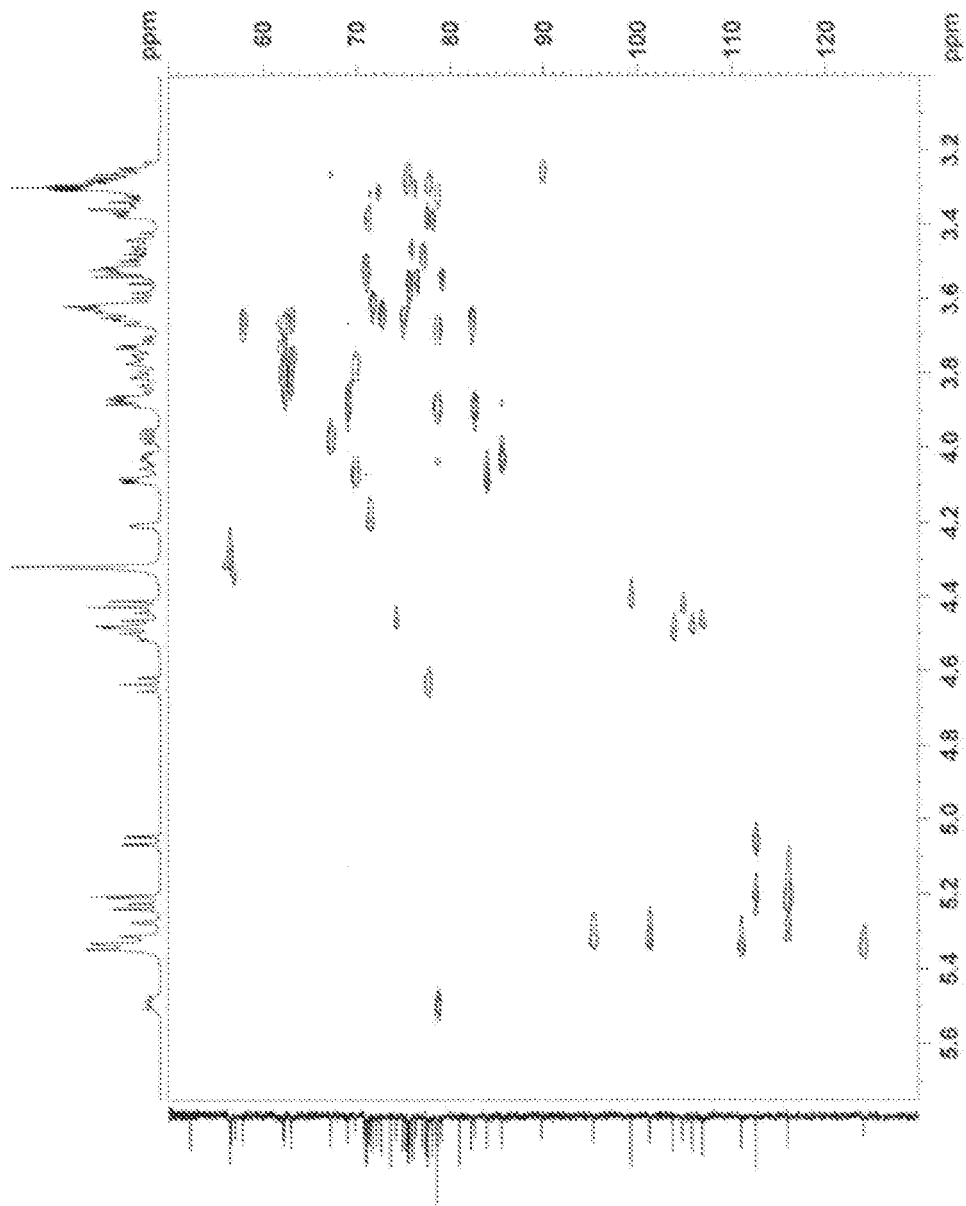

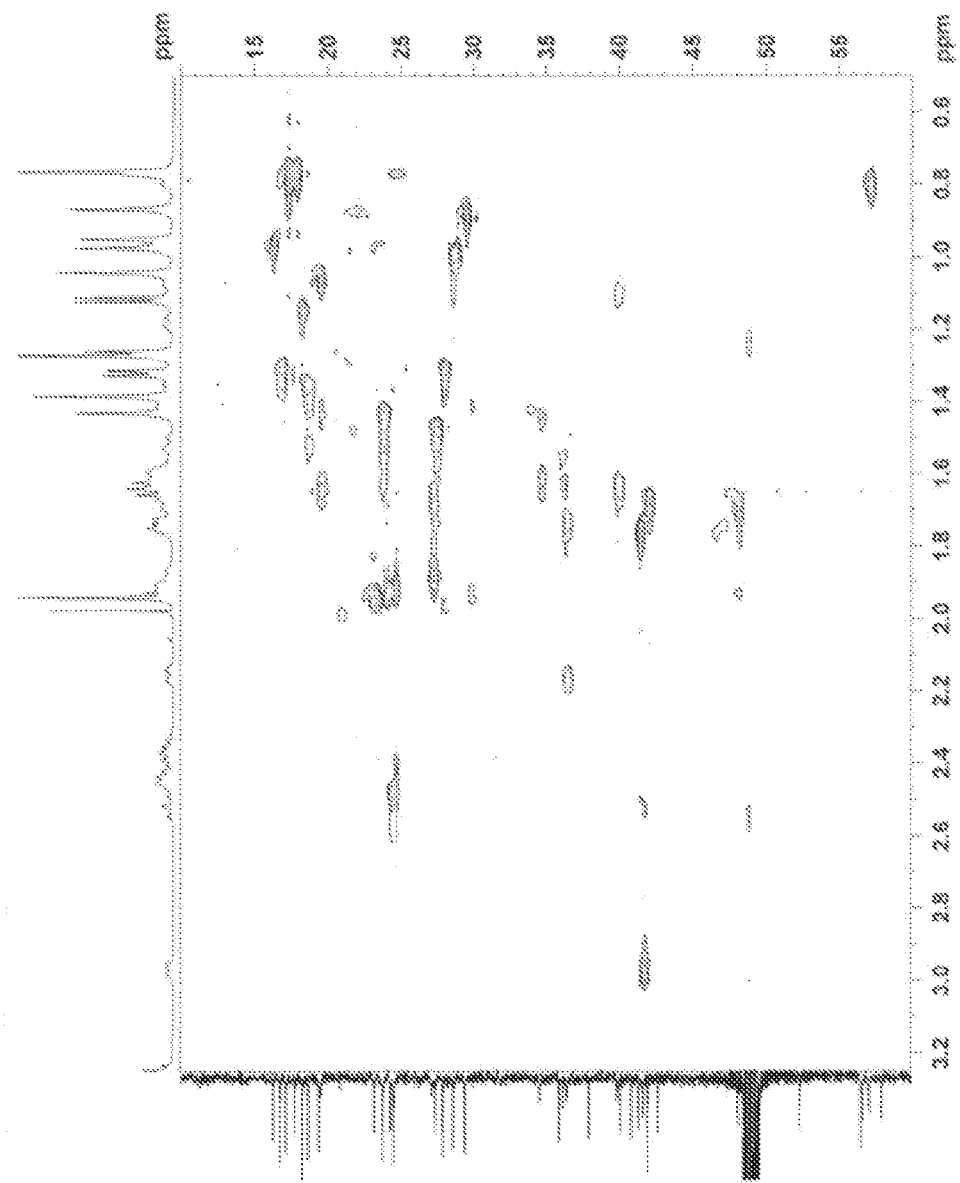

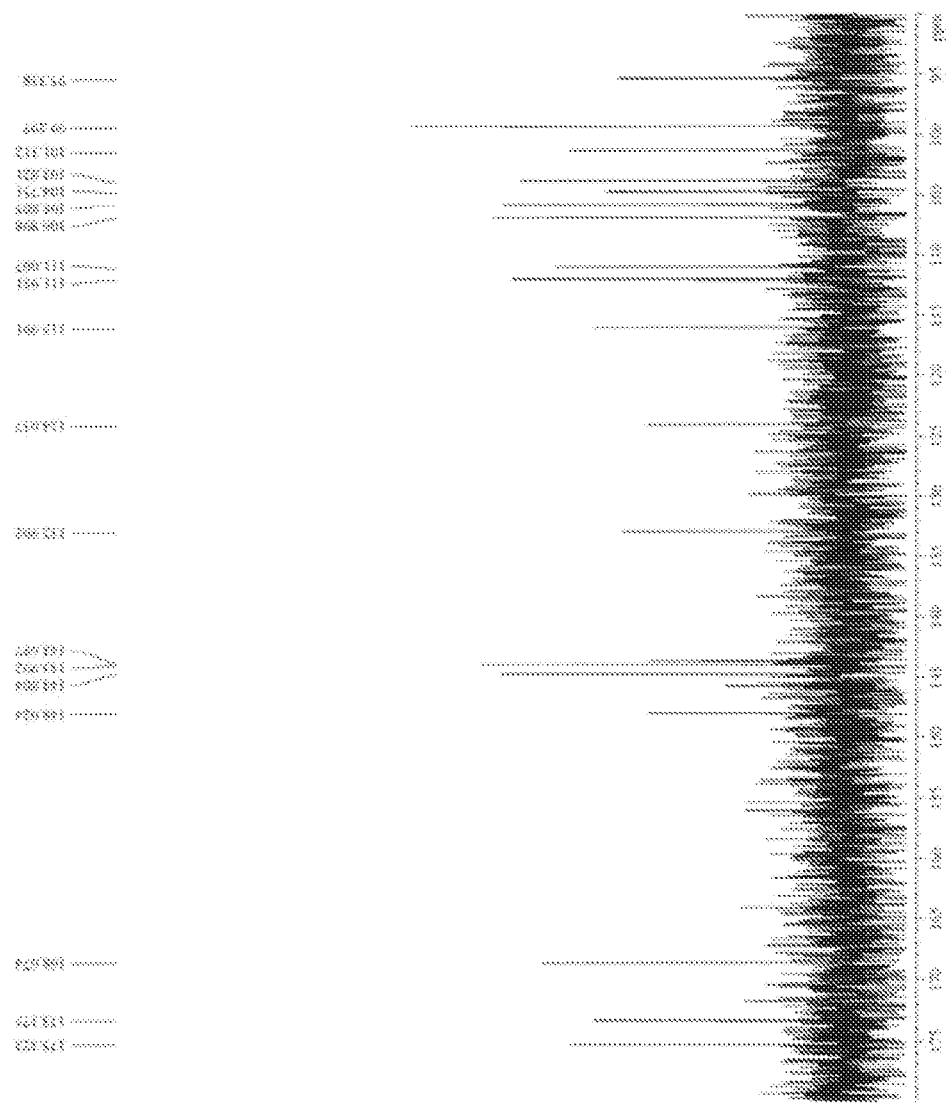

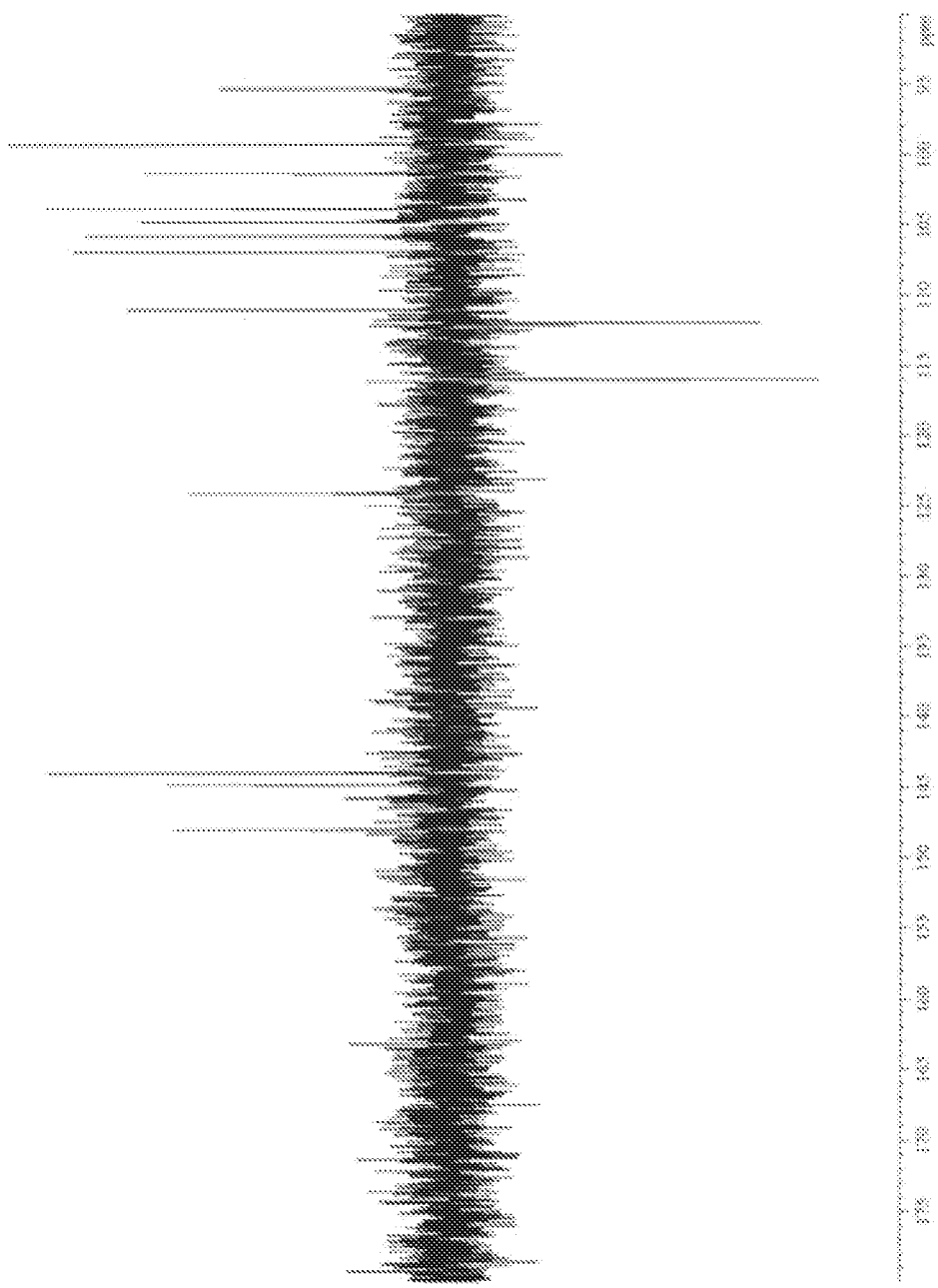

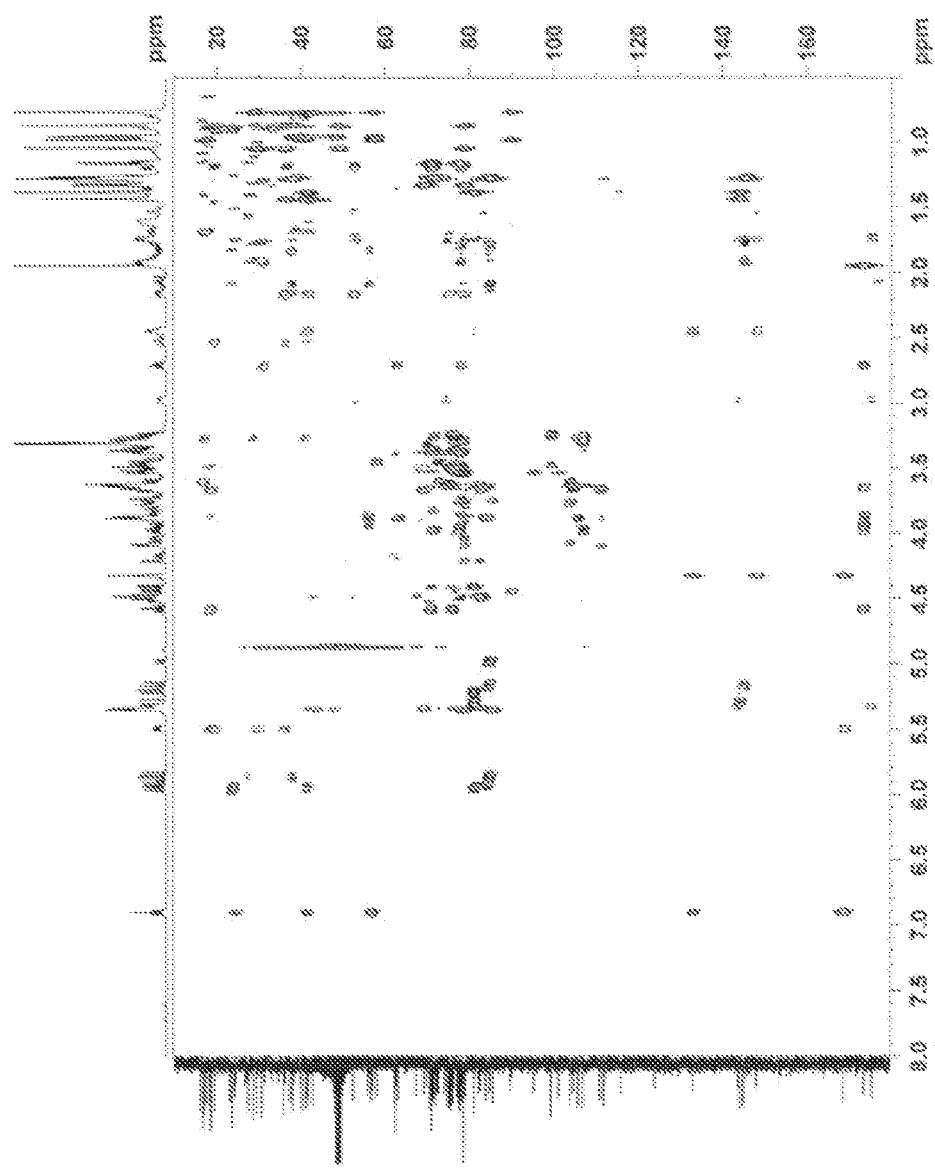

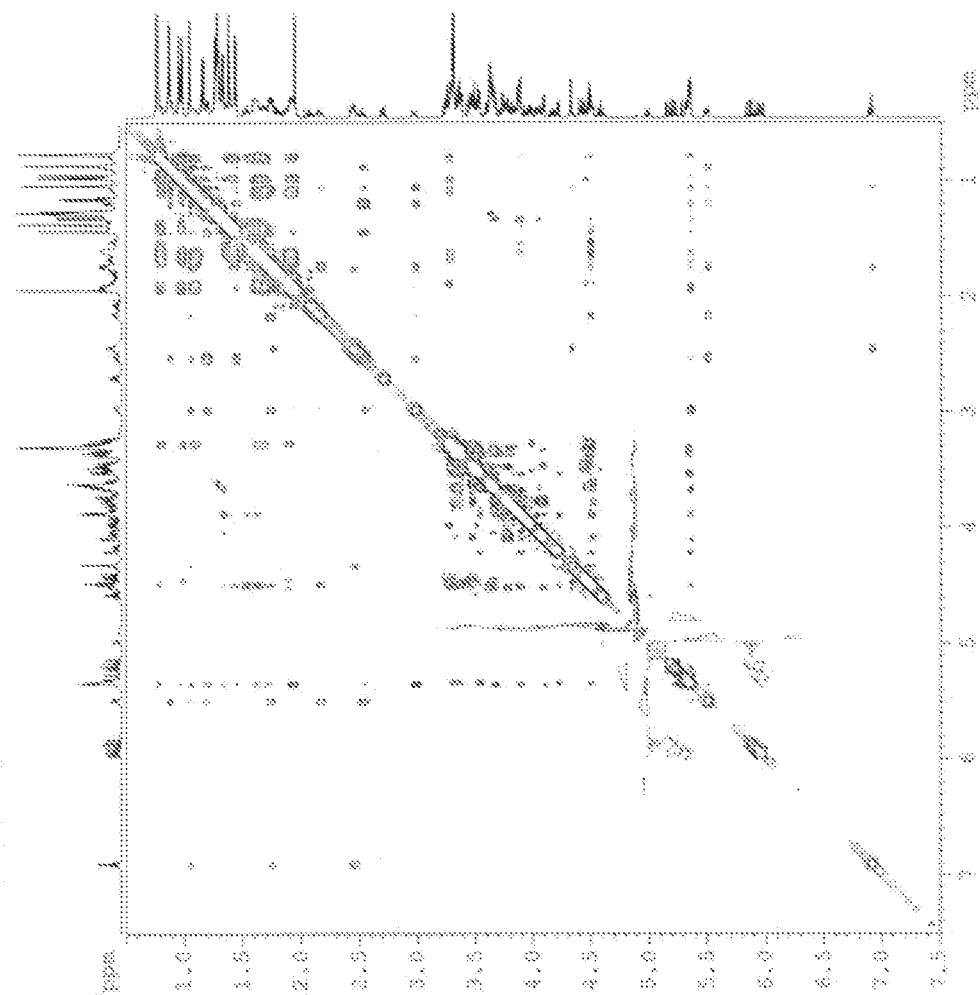

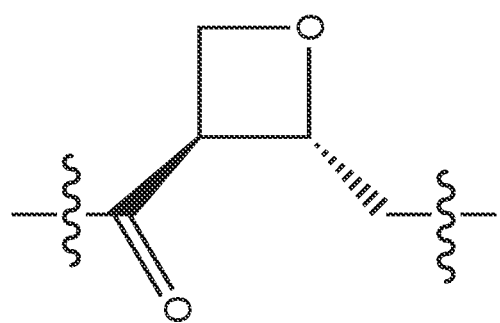
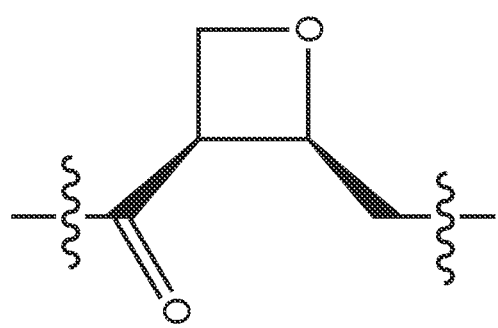
Figure 36

DERIVATIVES OF AVICIN D AND METHODS OF MAKING AND USING THEREOF

This application is a national phase application under 35 U.S.C. §371 of International Application No. PCT/US2013/027362, filed Feb. 22, 2013, which claims the benefit of U.S. Provisional Patent Application No. 61/602,917, filed Feb. 24, 2012, the entirety of each of which is incorporated herein by reference.

BACKGROUND OF THE INVENTION

I. Field of the Invention

The present invention relates generally to the fields of biology, chemistry and medicine. More particularly, it concerns derivatives of avicin D, and methods of making and using thereof, including for the treatment of cancer.

II. Description of Related Art

Avicins, a family of plant triterpene electrophiles, have been reported to trigger apoptosis-associated tumor cell death, and suppress chemical-induced carcinogenesis by their anti-inflammatory, anti-mutagenic, and antioxidant properties.

Avicins can be isolated from the Australian desert tree (Leguminosae) *Acacia victoriae*. The extraction and purification of avicins from the ground pods of *Acacia victoriae* is described in detail by U.S. Pat. No. 6,444,233, which is incorporated herein by reference. Using induction of cell cytotoxicity as a screen, two compounds, avicin D and avicin G, were identified as having significant activity.

Avicin D has been shown to inhibit NF-κB and activate NF-E2-related factor 2 (Nrf2) respectively, both in a redox-dependant manner, accounting for its anti-inflammatory and antioxidant properties. The ability of avicins to interact with, and modify cysteine residues was first demonstrated in a bacterial system with OxyR as a target, wherein it was demonstrated that the distal portion of the avicin side chain formed a reversible and covalent thioester bond with the critical cysteine (SH) on the OxyR molecule. This protein modification, termed avicinylation, suggested that avicins can be used induce post-translational changes in proteins to regulate their function.

Given these promising properties and the pressing need for improved therepeutics in a diverse range of indications, it is desirable to synthesize new compounds with diverse structures that may have improved biological activity profiles. Therefore, it is an object of the invention to provide derivatives of avicin D, and methods of making and using these. For example, recent studies have shown the existence of self renewing, stem-like cells within tumors, now called cancer stem cells (CSCs). See Reya et al., 2001, which is incorporated herein by reference. CSCs are resistant to most anti cancer treatments and possess the ability to seed new tumors. Therefore agents that can target and kill these CSCs are actively sought after for more effective anti-cancer treatment.

SUMMARY OF THE INVENTION

The present disclosure provides novel compounds, including derivatives of Avicin D, methods for their manufacture, and methods for their use, including for the treatment and/or prevention of cancer or other diseases.

In some embodiments, there are provided compounds of the formula:

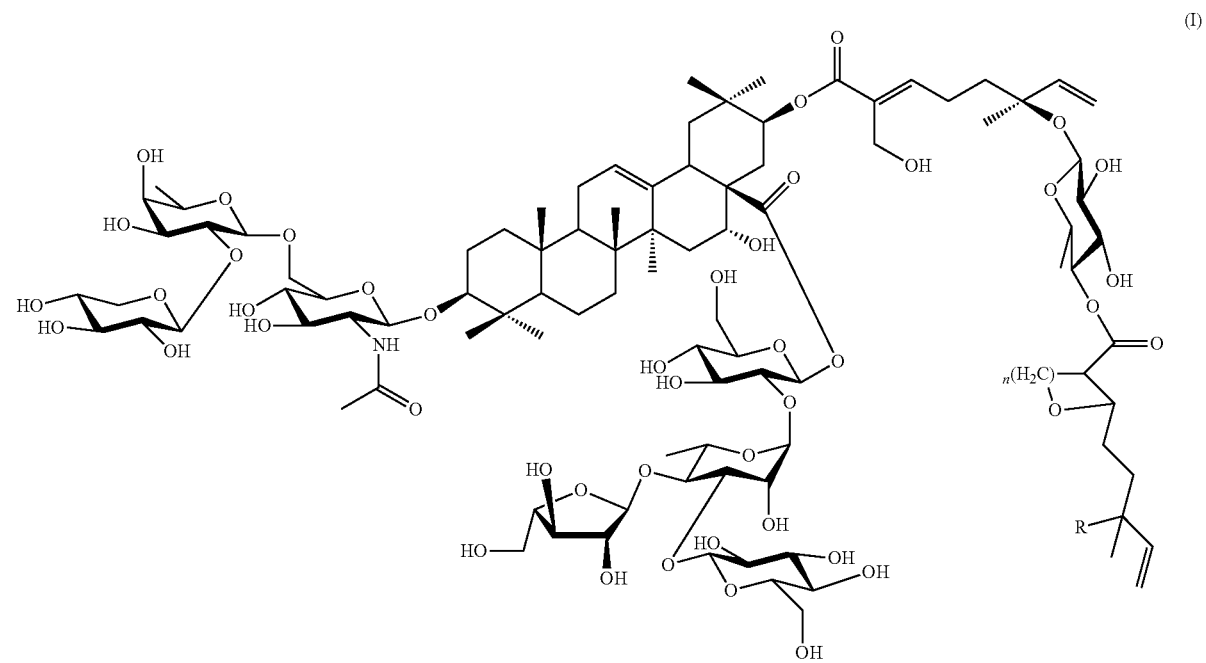

(I)

wherein:
n is 0-3, and
R is —H or —OH;
as well as pharmaceutically acceptable salts, acetals, ketals and tautomers thereof.

For example, there is provided a compound of the formula:

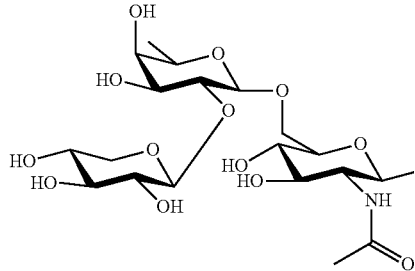
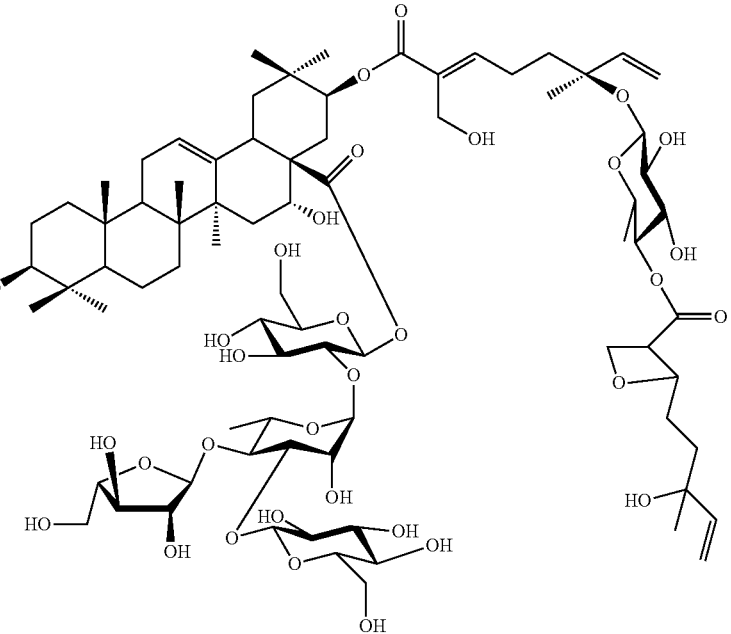

as well as pharmaceutically acceptable salts, acetals, ketals and tautomers thereof.

In some embodiments there are provided pharmaceutical compositions comprising one or more of the above compounds and a pharmaceutically acceptable carrier. In some embodiments, the composition is formulated for oral administration. In some embodiments, the pharmaceutical compositions further comprise one or more pharmaceutically acceptable excipients. In some embodiments, the composition is formulated for controlled release.

In some embodiments, there are provided methods of treating proliferative disorders comprising administering to patients in need thereof an effective amount of a compound as defined above. In some embodiments, the proliferative disorder is cancer.

In some embodiments, there are provided methods of treating inflammatory disorders comprising administering to patients in need thereof effective amounts of a compound as defined above.

In some embodiments, there are provided methods of treating a disease or disorder associated with chemotaxis comprising administering to patients in need thereof an effective amounts of a compound as defined above. In some embodiments, the disease or disorder is selected from the group consisting of autoimmune diseases and irritable bowel syndrome.

In some embodiments, there are provided methods of treating metabolic disorder comprising administering to patients in need thereof effective amounts of a compound as defined above. For example, in some embodiments, the metabolic disorder is obesity, diabetes, or combinations thereof.

The avicin derivatives described herein, and optional one or more additional active agents, can be combined with one or more pharmaceutically acceptable excipients and formulated for enteral, parenteral, topical, or pulmonary administration. Suitable oral dosage forms include, but are not limited to, tablets, caplets, capsules, syrups, solutions, suspensions, and emulsions. Suitable injectable formulations include solutions and suspensions. Suitable topical formulations include lotions, creams, ointments, and patches. Suitable pulmonary formulations include solution, suspensions, or aerosols which can be inhaled into the lung.

The compounds described herein can be used to treat a variety of diseases or disorders. Exemplary disorders include proliferative disorders, such as cancer; metabolic disorders, such as diabetes, diseases and disorders associated with chemotaxis, such as autoimmune diseases and irritable bowel syndrome, and combinations thereof.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

FIG. 2A shows that avicin D inhibits activation of NF-κB in a similar manner to dexamethasone (Dex). FIG. 2B shows that avicin D suppresses the expression of both constitutive and TNF-induced IL-6.

FIGS. 6A-D compares the effects of Avicin D and Compound 8 on the formation and growth of mammospheres generated from HMLE cells transfected with transcription factor TWIST. Expression of TWIST induces the HMLE cells to undergo an epithelial to mesenchymal transition (EMT) and is used as a model for cancer stem cells. Both Avicin D and Compound 8 appear to inhibit the development of mammospheres as measured by the size of these spheres. Shown in FIGS. 6B and 6D are spheres treated with 60 nM of avicin D and Compound 8, respectively, for fourteen days.

FIGS. 7A-7D are the $^1$H NMR spectra (500 MHz, CD$_3$OD) of Avicin D. FIG. 7A shows the spectrum of Avicin D at full scale. FIG. 7B shows an expansion of the spectrum of Avicin D in the downfield region. FIG. 7C shows an expansion of the spectrum of Avicin D in the midfield region. FIG. 7D shows an expansion of the spectrum of Avicin D in the upfield region.

FIGS. 8A-8D are the $^{13}$C NMR spectra (125 MHz, CD$_3$OD) of Avicin D. FIG. 8A shows the spectrum of Avicin D at full scale. FIG. 8B shows an expansion of the spectrum of Avicin D in the downfield region. FIG. 8C shows an expansion of the spectrum of Avicin D in the midfield region. FIG. 8D shows an expansion of the spectrum of Avicin D in the upfield region.

FIGS. 9A-9D are DEPT-135 spectra (125 MHz, CD$_3$OD) of Avicin D. FIG. 9A shows the spectrum of Avicin D at full scale. FIG. 9B shows an expansion of the spectrum of Avicin D in the downfield region. FIG. 9C shows an expansion of the spectrum of Avicin D in the midfield region. FIG. 9D shows an expansion of the spectrum of Avicin D in the upfield region.

FIGS. 10A-10B are $^1$H-$^1$H COSY spectra (500 MHz, CD$_3$OD) of Avicin D. FIG. 10A shows the spectrum of Avicin D at full scale. FIG. 10B shows the spectrum of Avicin D with an expanded view of the glycoside portion of the spectrum.

FIGS. 11A-11C are HSQC spectra (500 MHz, CD$_3$OD) of Avicin D. FIG. 11A shows the spectrum of Avicin D at full scale. FIG. 11B shows an expansion of the spectrum of Avicin D on the midfield region. FIG. 11C shows an expansion of the spectrum of Avicin D on the upfield region.

FIG. 12A shows the HMBC spectrum of Avicin D at full scale. FIG. 12B shows an expansion of the spectrum of Avicin D at both the $^1$H and $^{13}$C downfield quadrents. FIG. 12C shows an expansion of the spectrum of Avicin D at the $^1$H downfield quadrent and the $^{13}$C upfield quadrent. FIG. 12D shows an expansion of the spectrum of Avicin D at the $^1$H upfield quadrent and the $^{13}$C downfield quadrent. FIG. 12E shows an expansion of the spectrum of Avicin D at both the $^1$H and $^{13}$C upfield quadrents.

FIG. 13A shows the spectrum of Avicin D at full scale. FIG. 13B shows an expansion of the glycoside portion of the spectrum of Avicin D.

FIG. 14A shows the spectrum of Compound 8 at full scale. FIG. 14B shows an expansion of the spectrum of Compound 8 in the downfield region. FIG. 14C shows an expansion of the spectrum of Compound 8 in the midfield region. FIG. 14D shows an expansion of the spectrum of Compound 8 in the upfield region.

FIGS. 15A-15D are the $^{13}$C NMR spectra (125 MHz, CD$_3$OD) of Compound 8. FIG. 15A shows the spectrum of Compound 8 at full scale. FIG. 15B shows an expansion of the spectrum of Compound 8 in the downfield region. FIG. 15C shows an expansion of the spectrum of Compound 8 in the midfield region. FIG. 15D shows an expansion of the spectrum of Compound 8 in the upfield region.

FIGS. 16A-16D are the DEPT-135 spectra (125 MHz, CD$_3$OD) of Compound 8. FIG. 16A shows the spectrum of Compound 8 at full scale. FIG. 16B shows an expansion of the spectrum of Compound 8 in the downfield region. FIG. 16C shows an expansion of the spectrum of Compound 8 in the midfield region. FIG. 16D shows an expansion of the spectrum of Compound 8 in the upfield region.

FIG. 17A shows the spectrum of Compound 8 at full scale. FIG. 17B shows an expansion of the spectrum at the glycoside portion of Compound 8.

FIG. 18A shows the spectrum of Compound 8 at full scale. FIG. 18B shows an expansion of the spectrum of Compound 8 in the midfield region. FIG. 18C shows an expansion of the spectrum of Compound 8 in the upfield region.

FIGS. 19A-19E is the HMBC spectra (500 MHz, CD$_3$OD) of Compound 8. FIG. 19A shows the spectrum of Compound 8 at full scale. FIG. 19B shows an expansion of the spectrum at both the $^1$H and $^{13}$C downfield quadrents. FIG. 19C shows an expansion of the spectrum at the $^1$H downfield quadrent and the $^{13}$C upfield quadrent. FIG. 19D shows an expansion of the spectrum at the $^1$H upfield quadrent and the $^{13}$C downfield quadrent. FIG. 19E shows an expansion of the spectrum at both the $^1$H and $^{13}$C upfield quadrents.

FIG. 20A shows the spectrum of Compound 8 at full scale. FIG. 20B shows an expansion of the spectrum of Compound 8 at the glycoside region.

FIGS. 21A-21B are 2-D NOESY spectra (500 MHz, CD$_3$OD) of Compound 8. FIG. 21A shows the spectrum of Compound 8 at full scale. FIG. 21B shows an expansion of the spectrum of Compound 8 at the midfield region.

FIG. 36 shows the two stereoisomers of the oxetane, cis and trans.

DETAILED DESCRIPTION OF THE INVENTION

Figure 1A:
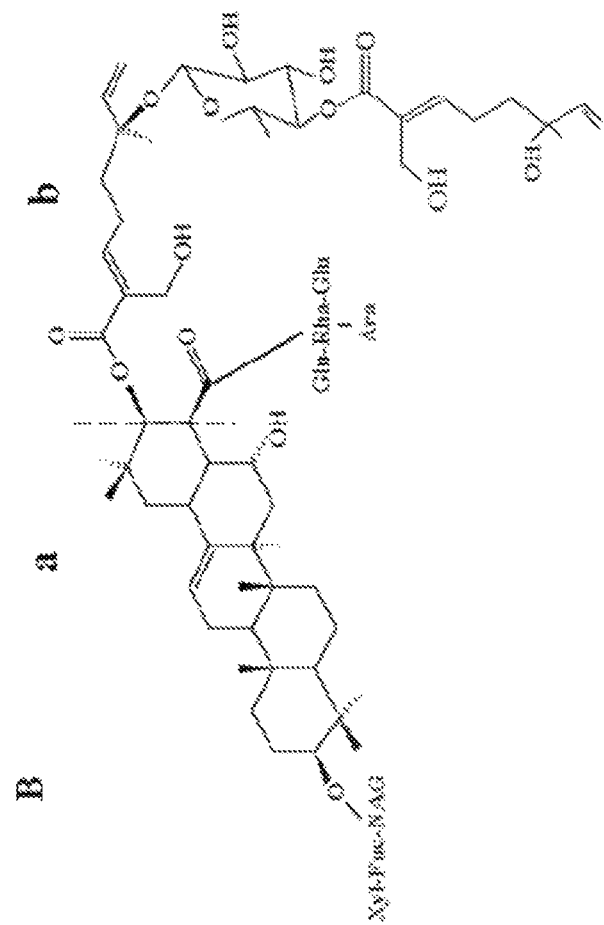
FIG. 1A is the steroidal backbone.

Disclosed herein are Avicin D derivatives, methods for their manufacture, and methods for their use, including for the treatment and/or prevention of cancer or other diseases.

I. DEFINITIONS

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$ or —$OC(O)CH_3$.

"Aglycone", as used herein, generally refers to the pentacyclic core of an avicin, exclusive of any carbohydrate and terpenoid groups.

"C-3 glycone", as used herein, refers to the sugar group at C-3 of the aglycone core.

"C-28 glycone", as used herein, refers to the glycoside substituent at the C-28 carbonyl of the aglycone core.

"C-21 glycone", as used herein, refers to the terpenoid-glycoside substituent at C-21 of the aglycone core. The C-21 terpenoid glycoside of Avicin D contains two monoterpene groups, referred to herein as $MT_1$ or inner monoterpene group and $MT_2$ outer monoterpene group.

The term "glycoside" refers to a compound in which a sugar group is bound to a non-carbohydrate moiety. Typically the sugar group (glycone) is bonded through its anomeric carbon to another group (aglycone) via a glycosidic bond that has an oxygen, nitrogen or sulfur atom as a linker.

A "simple sugar" are the basic structural units of carbohydrates, which cannot be readily hydrolyzed into simpler units. The elementary formula of a simple monosaccharide is $C_nH_{2n}O_n$, where the integer n is at least 3 and rarely greater than 7. simple monosachharides may be named generically according on the number of carbon atoms n: trioses, tetroses, pentoses, hexoses, etc. Simple sugars may be open chain (acyclic), cyclic or mixtures thereof. In these cyclic forms, the ring usually has 5 or 6 atoms. These forms are called furanoses and pyranoses, respectively—by analogy with furan and pyran. Simple sugars may be further classified into aldoses, those with a carbonyl group at the end of the chain in the acyclic form, and ketoses, those in which the carbonyl group is not at the end of the chain. Non-limiting examples of aldoses include: glycolaldehyde, glyceraldehydes, erythrose, threose, ribose, arabinose, xylose, lyxose, allose, altrose, glucose, mannose, gulose, idose, galactose and talose. Non-limiting examples of aldoses include: dihydroxyacetone, erythrulose, ribulose, xylulose, fructose, psicose, sorbose and tagatose. The 'D-' and 'L-' prefixes may be used to distinguish two particular stereoisomers which are mirror-images of each other. The term simple sugar also covers O-acetyl derivatives thereof.

A "amino sugar" refers to a derivative of a sugar, deoxy sugar, sugar acid or sugar alcohol, where one or more hydroxy group(s) has been replace with one more amino group(s). A "simple amino sugar" refers to a derivative of a simple sugar, simply deoxy sugar, simply sugar acid or sugar alcohol, where one or more hydroxy group(s) has been replace with one more amino group(s). These terms also cover N- and O-acetyl derivatives thereof. Non-limiting examples include N-acetylglucosamine, galactosamine, glucosamine and sialic acid.

The term "deoxy sugar" refers to a sugar derivative where one of the hydroxy groups of a carbohydrate has been replaced with a hydrogen atom. A "simple deoxy sugar" is a deoxy sugar derived from a simple sugar, as defined herein. These terms also cover O-acetyl derivatives thereof. Non-limiting examples of simple deoxy sugars are deoxyribose (based upon ribose), fucose, and rhamnose.

The term "sugar acid" refers to a sugar derivative where an aldehyde functional group or one or more hydroxy functional groups has been oxidized to a carboxyl group. Aldonic acids are those in which the aldehyde functional group of an aldose has been oxidized. Ulosonic acids are those in which the first hydroxyl group of a 2-ketose has been oxidized creating an α-ketoacid. Uronic acids are those in which the terminal hydroxyl group of an aldose or ketose has been oxidized. Aldaric acids are those in which both ends of an aldose have been oxidized. Non-limiting aldonic acids include glyceric acid (3C), xylonic acid (5C), gluconic acid (6C), and ascorbic acid (6C, unsaturated lactone). Non-limiting examples of ulosonic acids include neuraminic acid (5-amino-3,5-dideoxy-D-glycero-D-galacto-non-2-ulosonic acid) and ketodeoxyoctulosonic acid (KDO or 3-deoxy-D-manno-oct-2-ulosonic acid). Non-limiting examples of uronic acids include glucuronic acid (6C), galacturonic acid (6C), and iduronic acid (6C). Non-limiting example of aldaric acids include tartaric acid (4C), meso-galactaric acid (mucic acid) (6C), and D-glucaric acid (saccharic acid) (6C). A "simple sugar acid" is a sugar acid derived from a simple sugar. These terms also cover O-acetyl derivatives thereof.

The term "sugar alcohol" refers to a sugar derivative whose carbonyl group (aldehyde or ketone, reducing sugar) has been reduced to a primary or secondary hydroxyl group. Non-limiting examples of sugar alcohols include: glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), iditol (6-carbon), isomalt (12-carbon), maltitol (12-carbon), lactitol (12-carbon) or polyglycitol. A "simple sugar alcohol" is a sugar alcohol derived from a simple sugar. These terms also cover O-acetyl derivatives thereof.

As used herein, the term "monosaccharide group" refers to a monovalent carbohydrate group, with a carbon atom as the point of attachment. The term covers the groups resulting from removal of a hydroxyl radical from a simple sugar (e.g., glucose), simple deoxy sugar (e.g., fucose), simple sugar acid (e.g., gluconic acid), simple sugar alcohol (e.g., xylitol) or simple amino sugar (e.g., glucosamine) Typically the monosaccharide group is bonded through its anomeric carbon to another group (aglycone) via oxygen atom linker. In some cases the linker may be a nitrogen or sulfur atom.

A "disaccharide group" is a monovalent carbohydrate group consisting of two monosaccharide groups, wherein the second monosaccharide group replaces a hydrogen on a hydroxy group of the first monosaccharide group. Non-limiting examples of disaccharide groups include those derived from sucrose, lactulose, lactose, maltose trehalose and cellobiose.

A "trisaccharide group" is a monovalent carbohydrate group consisting of three monosaccharide groups, wherein the second monosaccharide group replaces a hydrogen on a hydroxy group of the first monosaccharide group and the third monosaccharide group replaces a hydrogen on a hydroxy group of either the first or the second monosaccharide groups.

An oligosaccharide is a monovalent carbohydrate group consisting of three to ten, preferably three to six monosaccharide groups, wherein the second monosaccharide replaces a hydrogen on a hydroxy group of the first monosaccharide, the third monosaccharide replaces a hydrogen on a hydroxy group of either the first or the second monosaccharide groups, and subsequent monosaccharide groups replace hydrogens on any previously joined monosaccharide groups, thus forming either a linear or branched structure.

A terpenoid group is a monovalent radical derived from removing a hydrogen from a terpene, that is from compound derived from the biosynthesis of isoprene and having the molecular formula $(C_5H_8)_n$, wherein n is 1, 2, 3, 4, 5, 6, 7 or 8.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2 n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. OXETANE DERIVATIVES OF AVICIN

In some embodiments, the invention provides Avicin derivatives having the following formula:

(I)

wherein:
n is 0-3, and
R is —H or —OH;
as well as pharmaceutically acceptable salts, acetals, ketals and tautomers thereof.

The compounds provided by the present disclosure are above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The compounds can be formulated as a mixture of one or more diastereomers. Alternatively, the diastereomers can be separated and one or more of the diastereomers can be formulated individually. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

The compounds described herein may exist in unsolvated forms as well as solvated forms, including hydrated forms. In general, the solvated forms are equivalent to unsolvated forms and are within the scope of the compounds described herein. The compounds described herein may exist in multiple crystalline or amorphous forms. In general, all physical forms are equivalent for the uses described herein and are intended to be within the scope of the compounds described herein.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailabil-

III. FORMULATIONS

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

In one embodiment, the avicin derivative(s) are formulated in a carrier containing 5% dextrose, alone or in combination with 10% propylene glycol. In another embodiment, the avicins are formulated in 150 mMol NaCl solution and 10 mMol sodium acetate (pH adjusted to 4.5), optionally containing polysorbate 80. Formulations may be stable over a period of 6 months when stored at room temperature or 5° C., with the avicin purity averaging about 95%.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references such as "Pharmaceutical dosage form tablets" (1989), "Remington—The science and practice of pharmacy" (2000), and "Pharmaceutical dosage forms and drug delivery systems" (1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more avicin derivatives and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more avicins and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more avicin derivatives, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the avicins and/or additional active agents.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

D. Pulmonary Formulations

In one embodiment, the avicin derivatives are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids (Patton and Platz, 1992).

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung (Gonda, 1990). The deep lung, or alveoli, are the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm$^3$, porous endothelial basement membrane, and it is easily accessible.

IV. METHODS OF MAKING AVICIN DERIVATIVES

Precursor molecules used to make compounds described herein can be isolated from extracts of the species *Acacia victoriae*. Methods of extracting triterpene compositions and avicins are described in U.S. Pat. No. 6,444,233 to Arntzen et al., which are incorporated herein by reference. The avicin derivatives, particularly the oxetane derivatives, can also be prepared by the biocatalysis of avicin-containing extracts. Generally, one or more starting materials, such as Avicin D, is reacted with one or more enzymes and the resulting products are analyzed. Suitable enzymes include hydrolases (e.g., glycosidases, proteases, esterases, acylases, and lipases); laccases and oxidase/mediator combinations.

Alternatively, the oxetane derivatives described can be prepared synthetically or semi-synthetically from a naturally occurring precursor component, such as Avicin D, or another suitable starting material. Methodologies for converting an alkene to a cyclic moiety, such as cycloalkane, oxygen heterocycle, nitrogen heterocycle, sulfur heterocycle, or selenium heterocycle, are well known in the art. Larock (1999) describes methodologies for a variety of organic functional group transformations. These are incorporated herein by reference.

V. METHODS OF USING AVICIN DERIVATIVES

The compounds described herein can be administered to provide an effective amount to treat a variety of diseases and disorders, such as proliferative disorders (e.g., cancers), metabolic disorders (e.g., obesity and diabetes), diseases associated with chemotaxis (e.g., autoimmune disorders, infections, irritable bowel syndrome), and combinations thereof. The therapeutically effective doses are readily determinable using an animal model, as described in U.S. Pat. No. 6,444,233. For example, experimental animals bearing solid tumors are frequently used to optimize appropriate therapeutic doses prior to translating to a clinical environment. Such models are known to be reliable in predicting effective anti-cancer strategies.

In certain embodiments, it may be desirable to provide continuous delivery of one or more avicin derivatives to a patient in need thereof. For intravenous or intraarterial routes, this can be accomplished using drip systems, such as by intravenous administration. For topical applications, repeated application can be done or a patch can be used to provide continuous administration of the avicin derivatives over an extended period of time. Extended release formulations can also be used that provide limited but constant amounts of the drug over an extended period of time.

For internal applications, continuous perfusion of the region of interest may be desirable. This could be accomplished by catheterization, post-operatively in some cases, followed by continuous administration of the one or more avicin derivatives. The time period for perfusion can be readily determined by the attending physician clinician for a particular patient. Perfusion times typically range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered.

The compositions described herein contain an effective amount of the one or more avicin derivatives. The amount to be administered can be readily determined by the attending physician based on a variety of factors including, but not limited to, age of the patient, weight of the patient, disease or disorder to be treated, presence of a pre-existing condition, and dosage form to be administered (e.g., immediate release versus modified release dosage form). Typically, the effective amount is from about 0.1 mg/kg/day to about 100 mg/kg/day, more preferably from 0.1 mg/kg/day to 50 mg/kg/day, more preferably from 0.1 mg/kg/day to 25 mg/kg/day, and most preferably from 0.1 mg/kg/day to 10 mg/kg/day. Dosages greater or less than this may be administered depending on the diseases or disorder to be treated. For example, preliminary data suggests that avicins, such as Avicin D, are effective at inhibiting chemotaxis at picomolar and nanomolar concentrations, as discussed below.

A. Proliferative Disorders

1. Cancers

The avicin derivatives described herein can be administered to a subject in need thereof to treat the subject either prophylactically (i.e., to prevent cancer) or therapeutically (i.e., to treat cancer after it has been detected), including reducing tumor growth, reducing the risk of local invasiveness of a tumor, increasing survival time of the patient, and/or reducing the risk of metastasis of a primary tumor. The compounds described herein can contact a target cell to inhibit the initiation and promotion of cancer, to kill cancer/malignant cells, to inhibit cell growth, to induce apoptosis, to inhibit metastasis, to decrease tumor size, to otherwise reverse or reduce the malignant phenotype of tumor cells, and combinations thereof. This may be achieved by contacting a tumor or tumor cell with a single composition or pharmacological formulation that includes the avicin derivative(s), or by contacting a tumor or tumor cell with more than one distinct composition or formulation, simultaneously, wherein one composition includes one or more avicin derivatives described herein and the other includes a second agent.

Exemplary cancers which can be treated include, but are not limited to, cancer of the skin, colon, uterine, ovarian, pancreatic, lung, bladder, breast, renal system, and prostate. Other cancers include, but are not limited to, cancers of the brain, liver, stomach, esophagus, head and neck, testicles, cervix, lymphatic system, larynx, esophagus, parotid, biliary tract, rectum, endometrium, kidney, and thyroid; including squamous cell carcinomas, adenocarcinomas, small cell carcinomas, gliomas, neuroblastomas, and the like. Assay methods for ascertaining the relative efficacy of the compounds described herein in treating the above types of cancers as well as other cancers are well known in the art.

The compounds described herein can also be used to treat metastatic cancer either in patients who have received prior chemo, radio, or biological therapy or in previously untreated patients. In one embodiment, the patient has received previous chemotherapy. Patients can be treated using a variety of routes of administration including systemic administration, such as intravenous administration or subcutaneous administration, oral administration or by intratumoral injection. The pharmaceutical dose(s) administered would preferably contain from about 10 to about 25 mg of avicins per kg of patient body weight per day, including about 13, 16, 19, and 22 mg/kg/day. Alternatively, the patient could be treated with one or more pharmaceutical compositions comprising from about 1 mg/kg/day of the avicins of the invention to about 100 mg/kg/day, including about 3, 6, 9, 12, 15, 18, 21, 28, 30, 40, 50, 60, 70, 80 and 90 mg/kg/day of the avicins described herein.

The treatment course typically consists of daily treatment for a minimum of eight weeks or one injection weekly for a minimum of eight weeks. Upon election by the clinician, the regimen may be continued on the same schedule until the tumor progresses or the lack of response is observed.

The avicin derivatives described herein can also be used to treat patients who have been rendered free of clinical disease by surgery, chemotherapy, and/or radiotherapy. In these aspects, the purpose of therapy is to prevent or reduce the likelihood of recurrent disease. Adjuvant therapy can be administered in the same regimen as described above to prevent recurrent disease.

The avicin derivatives described herein can also be used to target and/or kill cancer stem cells (CSCs). Recent studies have shown the existence of self renewing, stem-like cells within tumors, now called cancer stem cells (CSCs). Reya et al., 2001, which is incorporated herein by reference. CSCs are resistant to most anti cancer treatments and possess the ability to seed new tumors. Based on the cytotoxicity results using a CSC model (Example 4), the avicin deriviates may be used to kill cancer stem cells (CSCs).

2. Anti-Inflammatory Disorders

The compounds described herein can also be used as anti-inflammatory agents. Avicin D has been shown to be an inhibitor of transcription factor NF-KB, which plays an important role in the inflammatory response. This finding is particularly significant given the increasing amount of evidence suggesting the central role of inflammatory response in carcinogenesis. Treatment of patients with the avicins described herein may, therefore, potentially alleviate a wide degree of ailments associated with inflammation, including tumorigenesis and tissue damage.

The initial stages of an inflammatory response are characterized by increased blood vessel permeability and release (exudation) of histamine, serotonin and basic polypeptides and proteins. This is accompanied by hyperaemia and oedema formation. Subsequently, there is cellular infiltration and formation of new conjunctive tissue. It is believed that treatment with the compounds of the invention can limit these early stages of inflammation and, thereby, decrease the negative effects associated with the inflammatory condition.

In one embodiment, one or more avicin derivatives are administered as non-steroidal selective glucocorticoid receptor modulators, alone or in combination with one or more glucocorticoids. Glucocorticoids (GCs) are essential steroid hormones, secreted by the adrenal cortex, that play a critical role in the maintenance of homeostasis in mammals. GCs are involved in the regulation of development, metabolism and stress responses. They are also known to be potent immunosuppressive, anti-allergic, and anti-inflammatory drugs.

GCs exert their effects via the glucocorticoid receptor (GR), a cytoplasmic transcription factor belonging to the superfamily of thyroid/steroid nuclear hormone receptors. Upon binding of a ligand, the GR is released from an inactive cytoplasmic complex, and translocates into the nucleus. In the nucleus, GR binds as a homodimer to consensus sequences, termed GC response elements (GREs), in the promoter region of GC-sensitive genes to induce transcription (transactivation), of various genes such as those encoding tyrosine amino transferase (TAT), some key enzymes of glycolysis, lipid metabolism and immune response. Another important mechanism of GR-mediated transcriptional regulation involves repression (transrepression) of transcription, and is mediated through GR-protein interactions.

For its transrepressive action, GR binds as a monomer to transcription factors, such as NF-KB, AP-1, Stat5 and others. Studies using transgenic mice harboring mutated GR have shown that the transrepressive activity of GRs is responsible for the anti-inflammatory actions of GCs. The desired anti-inflammatory and immunosuppressant effects of GCs, however, are most often accompanied by undesirable side effects, such as diabetes, obesity, hypertension, skin atrophy, and many others, most of which are believed to be mediated via transactivation. Studies showing that these two activities of GR are seperable has resulted in extensive efforts to identify ligands that preferentially induce the transrepression and not the transactivation function of GRs. Such ligands termed as "dissociated ligands" are likely to have immense therapeutic value with reduced side effects.

Figure 1B:
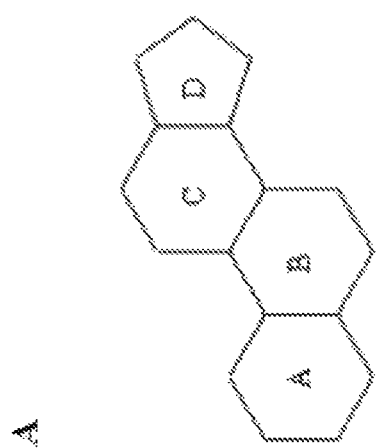
FIG. 1B is the structure of avicin D.
Figure 2A:
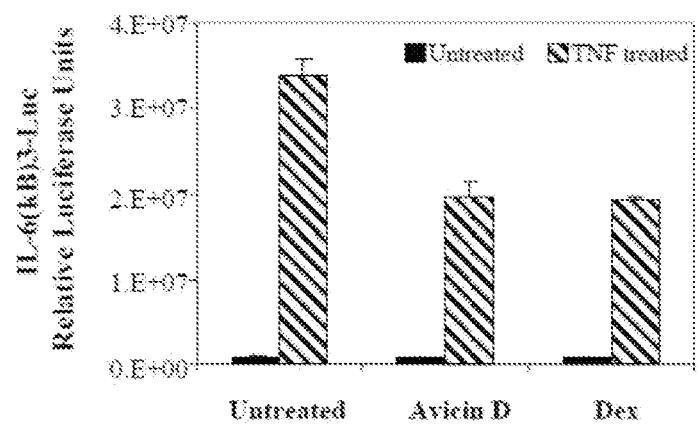
FIGS. 2A & 2B are graphs showing the ability of avicins to inhibit NF-KB and activate NF-E2-related factor 2 (Nrf2).
Figure 2B:
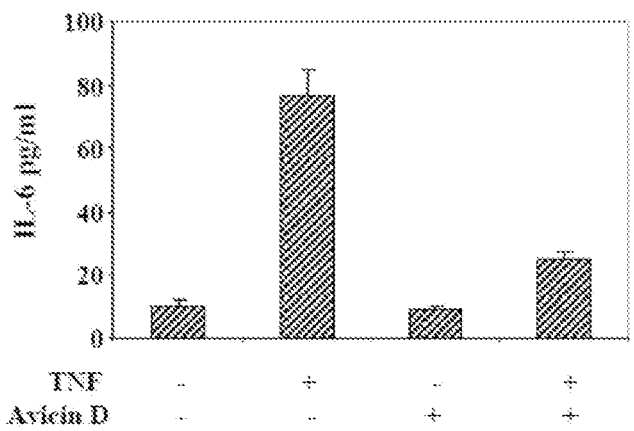

The pentacyclic backbone in the avicin derivatives described herein makes them structurally comparable to steroids (see FIGS. 1A & 1B). FIG. 1A is the steroidal backbone while FIG. 1B is Avicin D. Studies have shown that avicins are inhibitors of NF-KB and activate NF-E2-related factor 2 (Nrf2), accounting for their anti-inflammatory and stress responsive properties (see FIG. 2). FIG. 2A shows that Avicin D inhibits activation of NF-κB in a similar manner to dexamethasone. FIG. 2B shows that avicin D suppresses the expression of both constituitive and TNF-induced IL-6, in confirmation with the anti-inflammatory effects of avicins.

Figure 3:
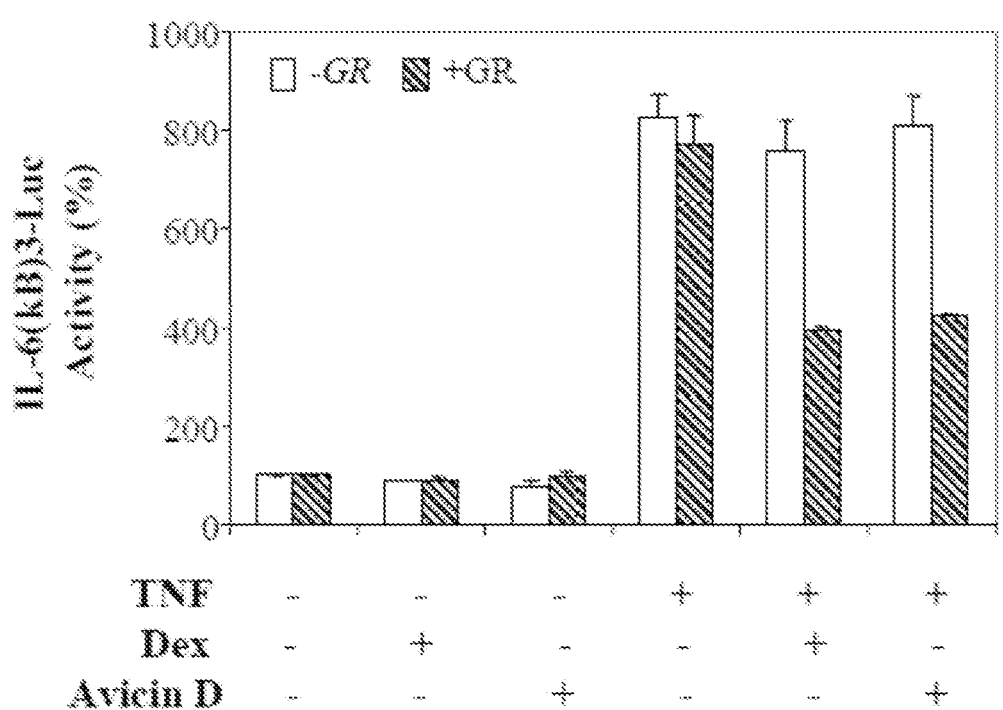
FIG. 3 is graph showing the expression of glucocorticoid receptor (GR) in HEK293T cells with and without GR.
Figure 4:
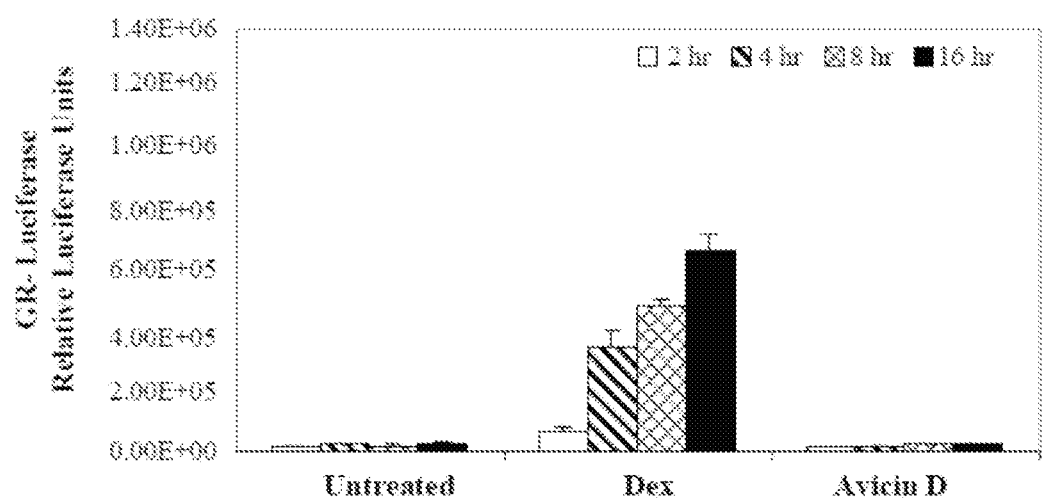
FIG. 4 is graph showing that avicin D does not enhance phosphorylation of Ser-211 even after 16 hours.

Previous studies have demonstrated that avicins can bind to GR and induce its nuclear translocation. This event is followed by inhibition of NF-KB activity via GR (see FIG. 3), while GR-driven transactivation itself is not induced, suggesting that avicins could act as dissociated ligands for GR (see FIG. 4). FIG. 3 shows the expression of GR in HEK293T cells with A549 and other cell lines. As shown in FIG. 3, neither avicin D nor dexamethasone had an effect on the luciferase activity in wild type HEK 293T cells. However, TNF-induced activation of p(IL6-κB)350hu.IL6P-Luc was inhibited by both avicin D and Dex in HEK 293T cells transfected with GR (FIG. 3). These results indicate that the presence of GR is required for avicin (as well as Dex) to down-regulate the activation of NF-κB. FIG. 4 shows that avicin D does not enhance phosphorylation of Ser-211 even after 16 hours. In contrast, dexamethasone under similar conditions induced Ser-211 phosphorylation. This observation supports the notion that avicins are not able to induce GR transactivation.

Modeling of avicin-GR interaction revealed that the avicin molecule binds to the antagonist confirmation of the GR, which supports the finding that avicins can act as a dissociated GR ligand. Avicins can therefore be classified as nonsteroidal selective GR modulators. The use of avicins in place of, or in combination with one or more glucocorticoids, reduces the dosage of glucocorticoid administered and thus should minimize the adverse side effects associated with these compounds.

3. Metabolic Disorders

The avicins described herein may be used to treat metabolic disorders. Recent studies have shown that avicins regulate cellular energy metabolism and activated AMP-activated protein kinase (AMPK), a key regulator of fatty acid and glucose homeostasis. This suggests that the avicins described herein may be used to treat metabolic diseases including obesity, a burgeoning disorder that contributes to cardiovascular disease, and diabetes (including both type I and type II diabetes). The avicins described herein can also be used to treat insulin resistance and metabolic syndrome.

Avicin D has been shown to inhibit adipogenesis and reduce intracellular triglyceride level in a dose-dependent manner in 3T3-L1 cells. Avicin D suppressed preadipocyte differentiation, but did not affect adipolysis and adipocyte apoptosis. Avicin D inhibited PKA-mediated CREB activity, which in turn suppressed the expression of adipogenesis genes, such as CEBPs and PPAR-γ. Avicin D increased the expression and secretion of adiponectin in adipocytes. Importantly, avicin D inhibited the differentiation of human preadipocytes to mature adipocytes and reduced intracellular triglyceride levels as well. Taken together, these results suggest that avicins could serve as important metabolic regulators in the control of adipogenesis and treatment and prevention of metabolic syndromes.

As discussed above, avicins can inactivate NF-κB pathway and decrease IL-6, TNFα-mediated inflammatory reaction. In addition, avicins can also activate the proteins downstream of Nrf2, such as glutathione peroxidase, heme oxygenase, and thioredoxin reductase in vitro and in vivo, indicative of their antioxidant effects. These data suggest that avicins may be effective in adipogenesis control.

As shown in the examples below, avicins exhibit potent activity to inhibit adipogenesis in vitro, and reduced serum total cholesterol, triglyceride, and LDL levels, increased serum HDL concentration ($p<0.05$) in vivo. More importantly, applying these compounds to either undifferentiated fibroblasts or mature adipocytes does not produce any cytotoxic effects. Administering avicins to hamsters orally did not cause observable side effects in these animals. Thus it has been demonstrated that avicins are highly effective in inhibiting adipogenesis while having no short-term side effects, which makes avicins potentially useful candidates for obesity control.

4. Diseases and Disorders Associated with Chemotaxis

Chemotaxis is the phenomenon in which bodily cells, bacteria, and/or other single-cell or multicellular organisms direct their movements according to certain chemicals in their environment. In multicellular organisms, chemotaxis is critical to early (e.g. movement of sperm towards the egg during fertilization) and subsequent phases of development (e.g. migration of neurons or lymphocytes) as well as in normal function. In addition, it has been recognized that mechanisms that allow chemotaxis in animals can be subverted during cancer metastasis.

In one embodiment, one or more avicin derivatives are administered alone or in combination with an additional active agent, such as corticosteroid to inhibit chemotaxis, for example, the migration of immune cells or cancer cells. The compounds described herein may inhibit chemotaxis at picomolar to low nanomolar concentrations.

5. Other Uses

The compounds described herein can be also be used as anti-fungal and anti-viral agents, piscicides or molluscicides, contraceptives, antihelmintics, UV-protectants, expectorants, diuretics, anti-inflammatory agents, regulators of cholesterol metabolism, cardiovascular effectors, anti-ulcer agents, analgesics, sedatives, immunomodulators, antipyretics, angiogenesis regulators, agents for decreasing capillary fragility, agents to combat the effects of aging, and agents for improving cognition and memory.

The compounds described herein may be used to regulate angiogenesis, alone or in combination with one or more additional angiogenesis modulators. Angiogenesis or neovascularization is defined as the growth of new blood vessels. Tumors and cancers induce angiogenesis to provide a life-line for oxygen and nutrients for the tumor to thrive. The development of new blood vessels also provides exits for malignant cancer cells to spread to other parts of the body. Angiogenesis inhibition therefore benefits cancer patients. On the other hand, angiogenesis is required at times such as wound healing. These wounds can be external wounds or internal organ wounds that result from accidents, burns, injury and surgery. Thus, agents that promote angiogenesis have a great potential for use in therapy for wound healing.

The compounds described herein can be used to modulate cholesterol metabolism. In particular, the compounds described here may be used to lower the serum cholesterol levels of human patients. For the treatment of cardiovascular conditions, the compounds described herein can be used to treat arrhythmic action and further may be used as a vascular relaxant, resulting in antihypertensive activity.

The plant species from which the compounds of the invention were identified, *Acacia victoriae*, was selected, in part, because it is native to arid regions. An important function of the metabolism of plants from these regions is the production of compounds which protect cells from ultraviolet radiation. The compounds described herein can be used as UV-protectants. For example, suitable applications include the use of the avicins described herein as an ingredient in sunblock, or other similar lotions for application to human skin.

Other possible applications of the avicins described herein include protection in the central nervous system damage, in effect, memory loss or enhanced cognitive function, use as an antioxidant (monitoring blood levels of oxidative molecules), or increase of nitric oxide (NO), for the treatment of hypertension or atherosclerosis.

VI. KITS

In various aspects, a kit is envisioned containing one or more compounds described herein. The kit may contain one or more sealed containers, such as a vial, containing any of the compounds described herein and/or reagents for preparing any of the compounds described herein. In some embodiments, the kit may also contain a suitable container means, which is a container that will not react with components of the kit, such as an Eppendorf tube, an assay plate, a syringe, a bottle, or a tube. The container may be made from sterilizable materials such as plastic or glass.

The kit may further include instructions that outline the procedural steps for methods of treatment or prevention of disease, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of one or more compounds described herein.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the claims.

Example 1

Preparation of Compound 8, an Oxetane Derivative of Avicin D

Figure 5:
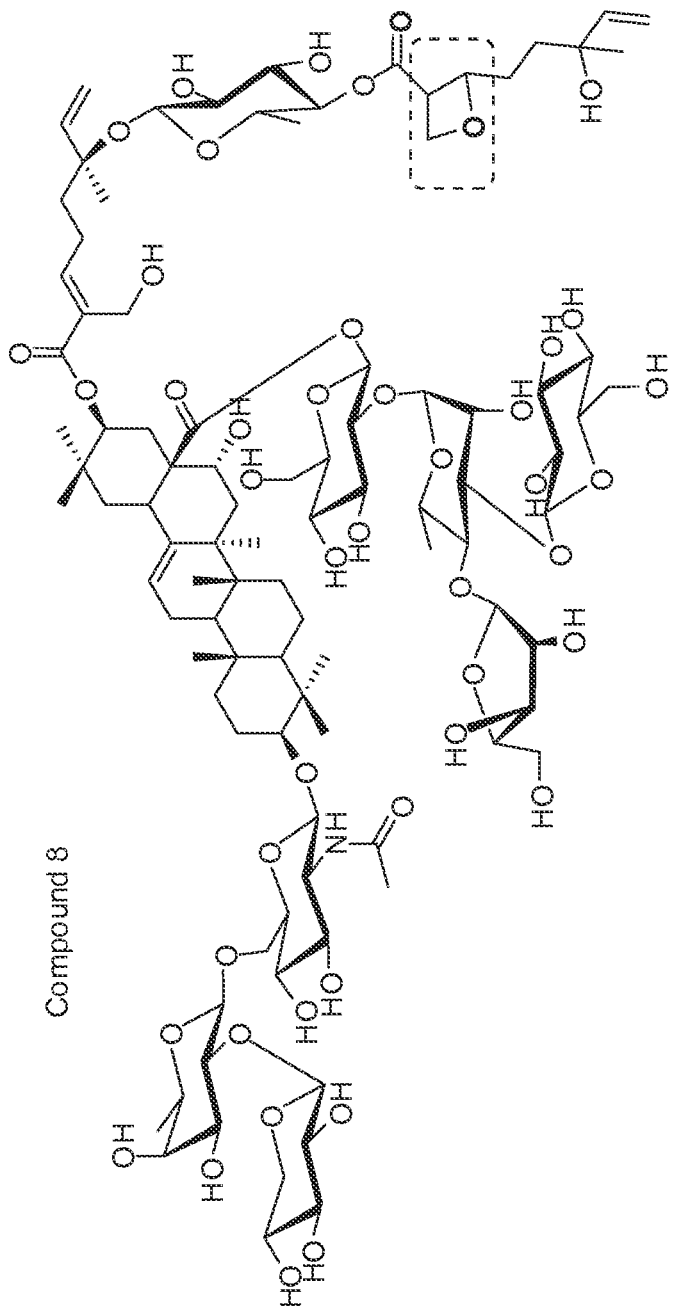
FIG. 5 shows the formula of Compound 8 [ALB-151440], an oxetane derivative of Avicin D. The dashed box highlights the oxetane group.
Figure 7A:
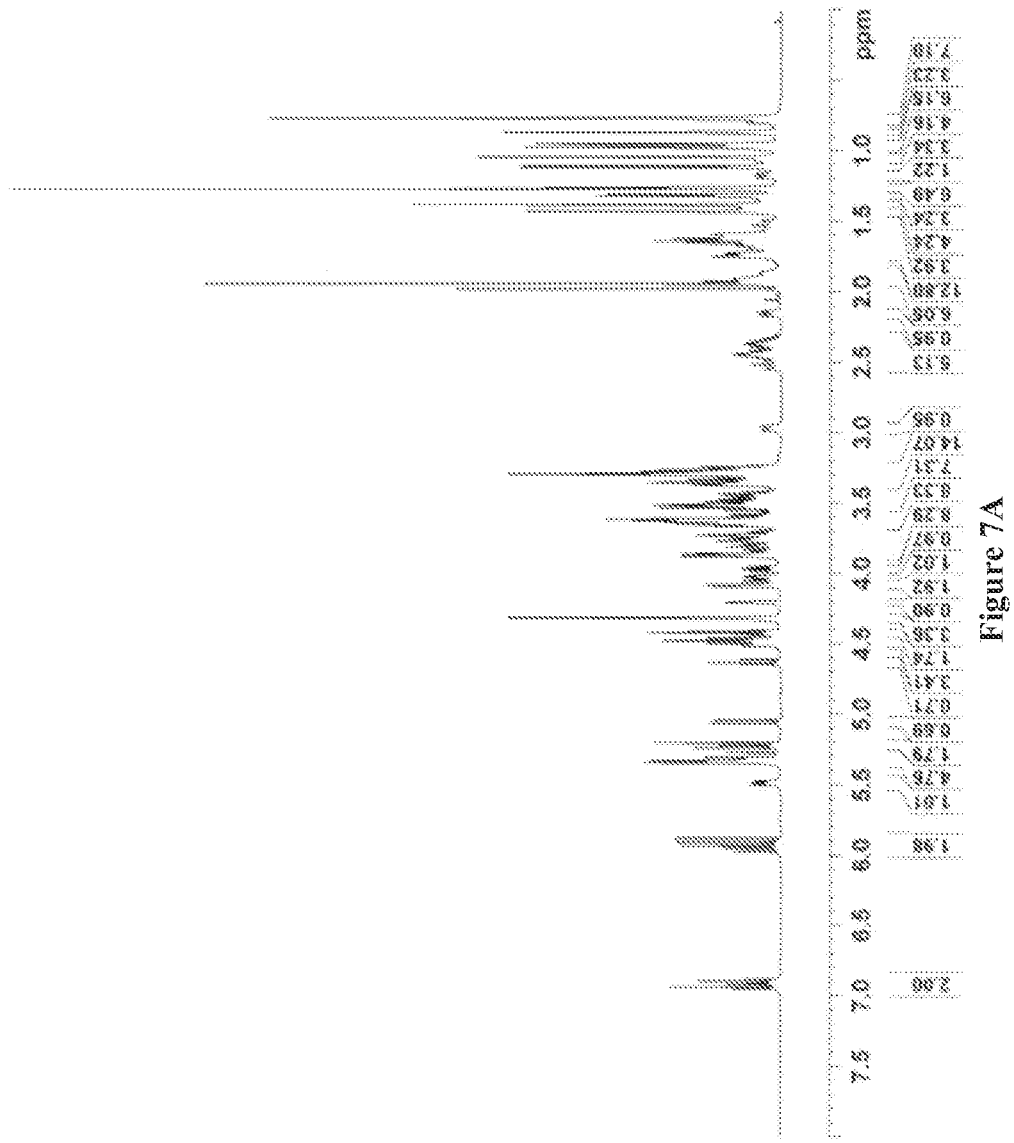
Figure 7B:
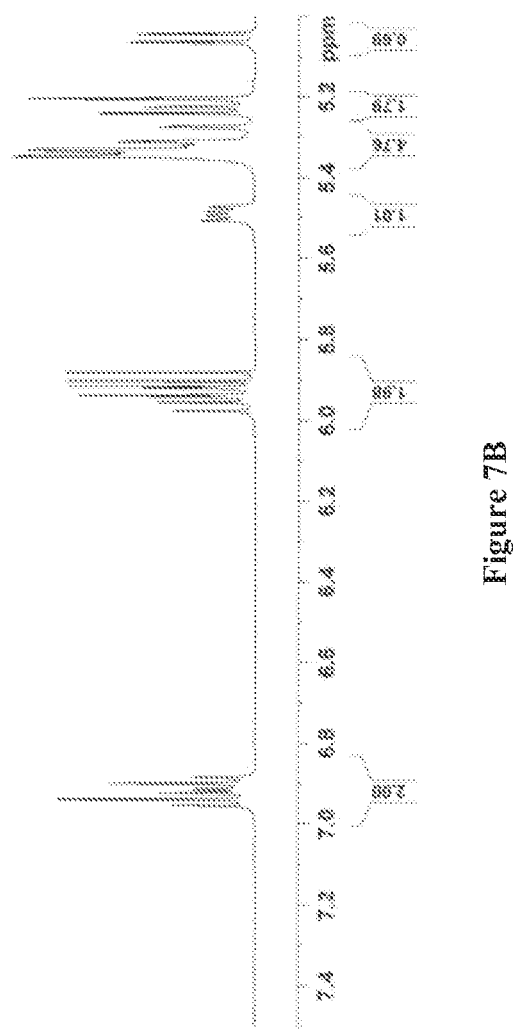
Figure 7C:
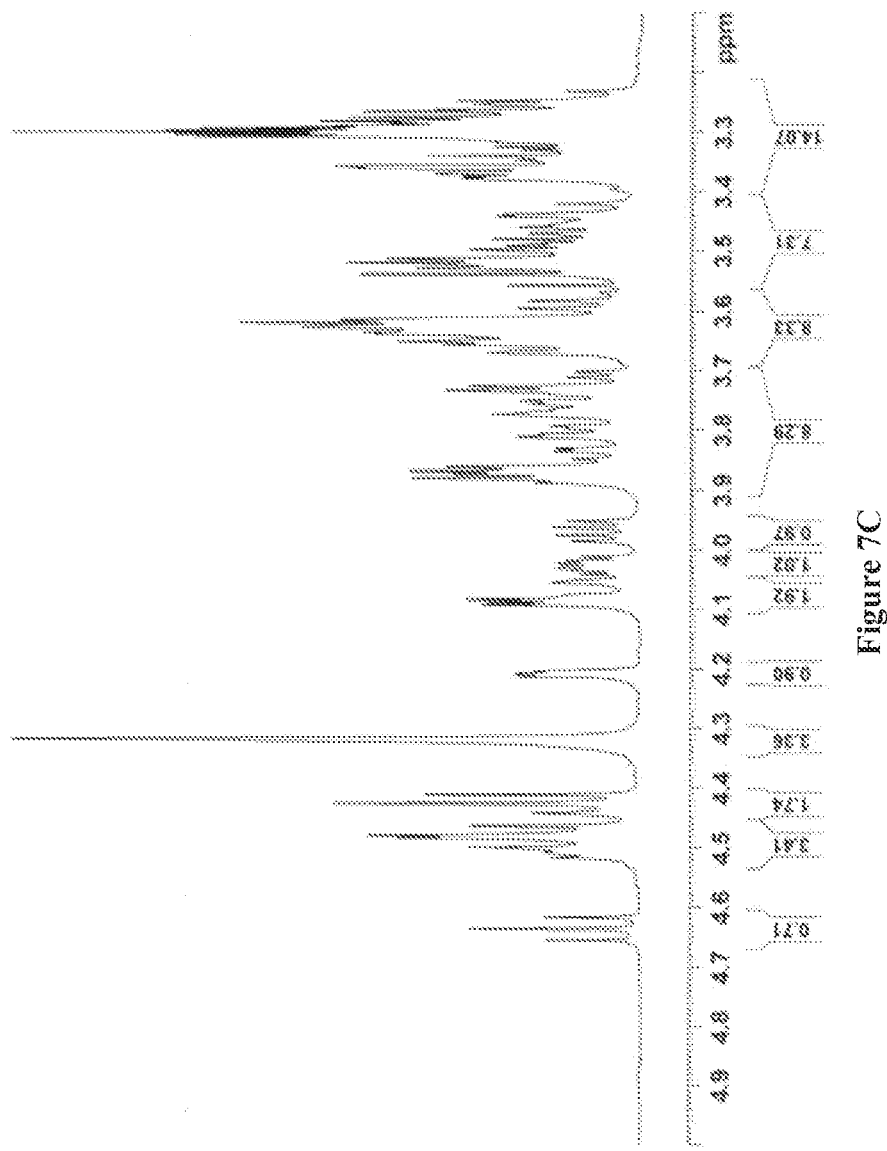
Figure 8A:
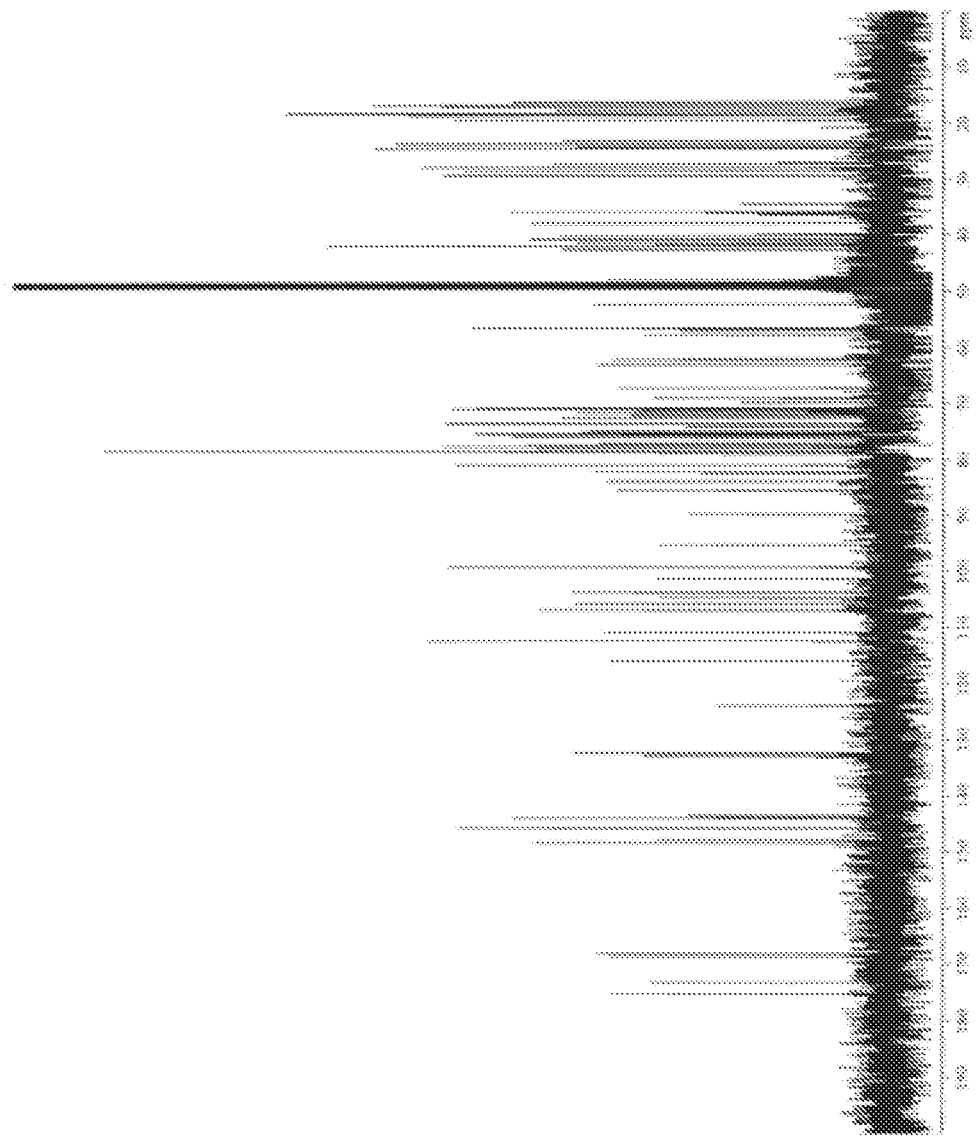
Figure 8B:
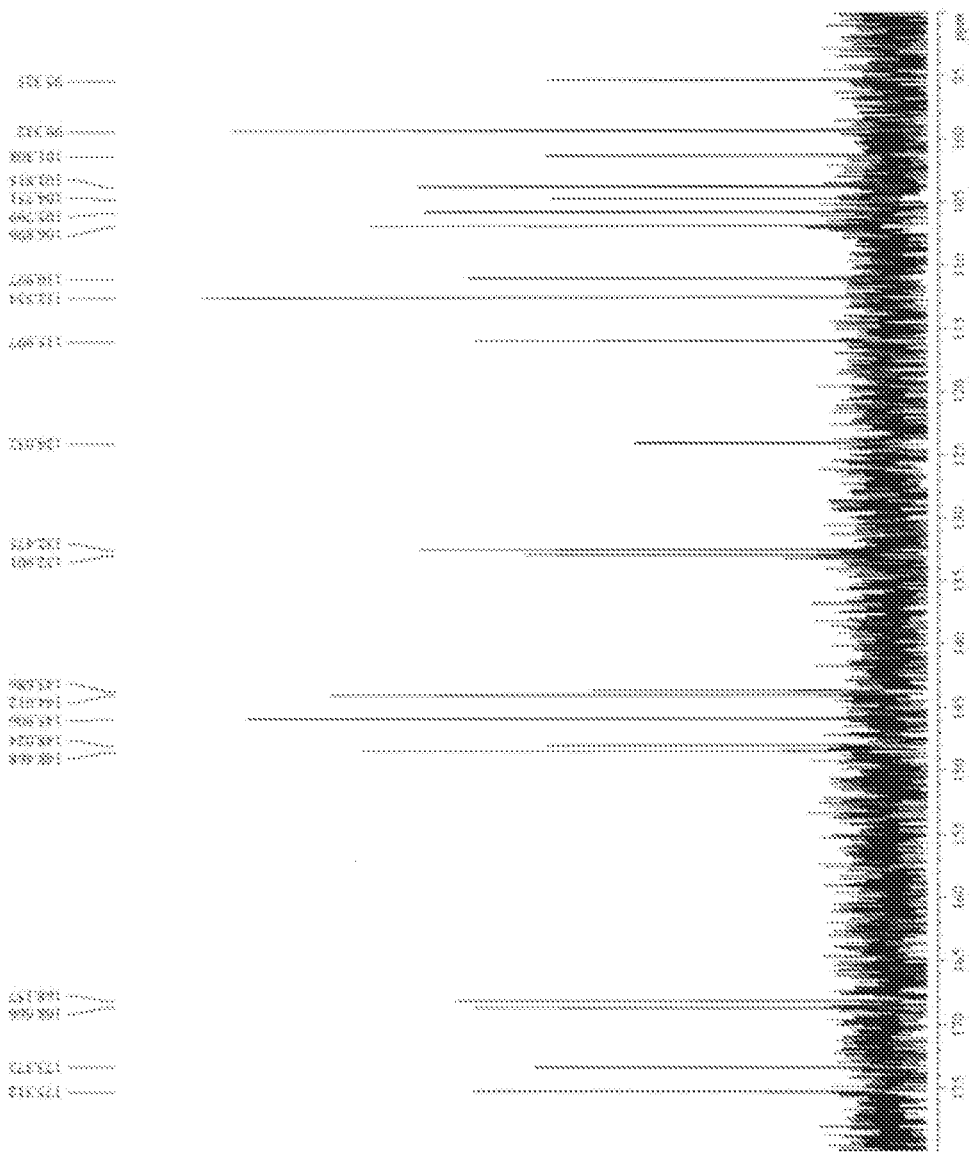
Figure 9A:
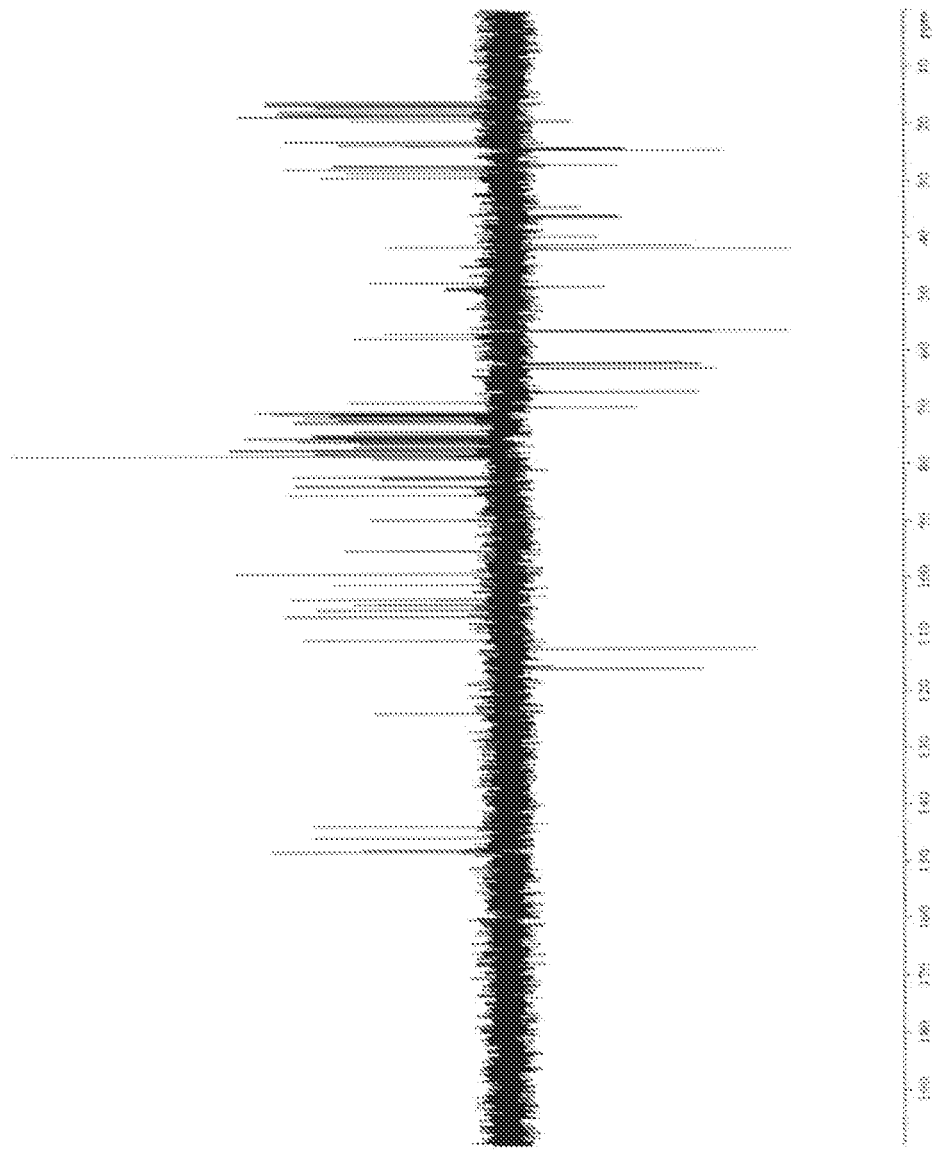
Figure 9B:
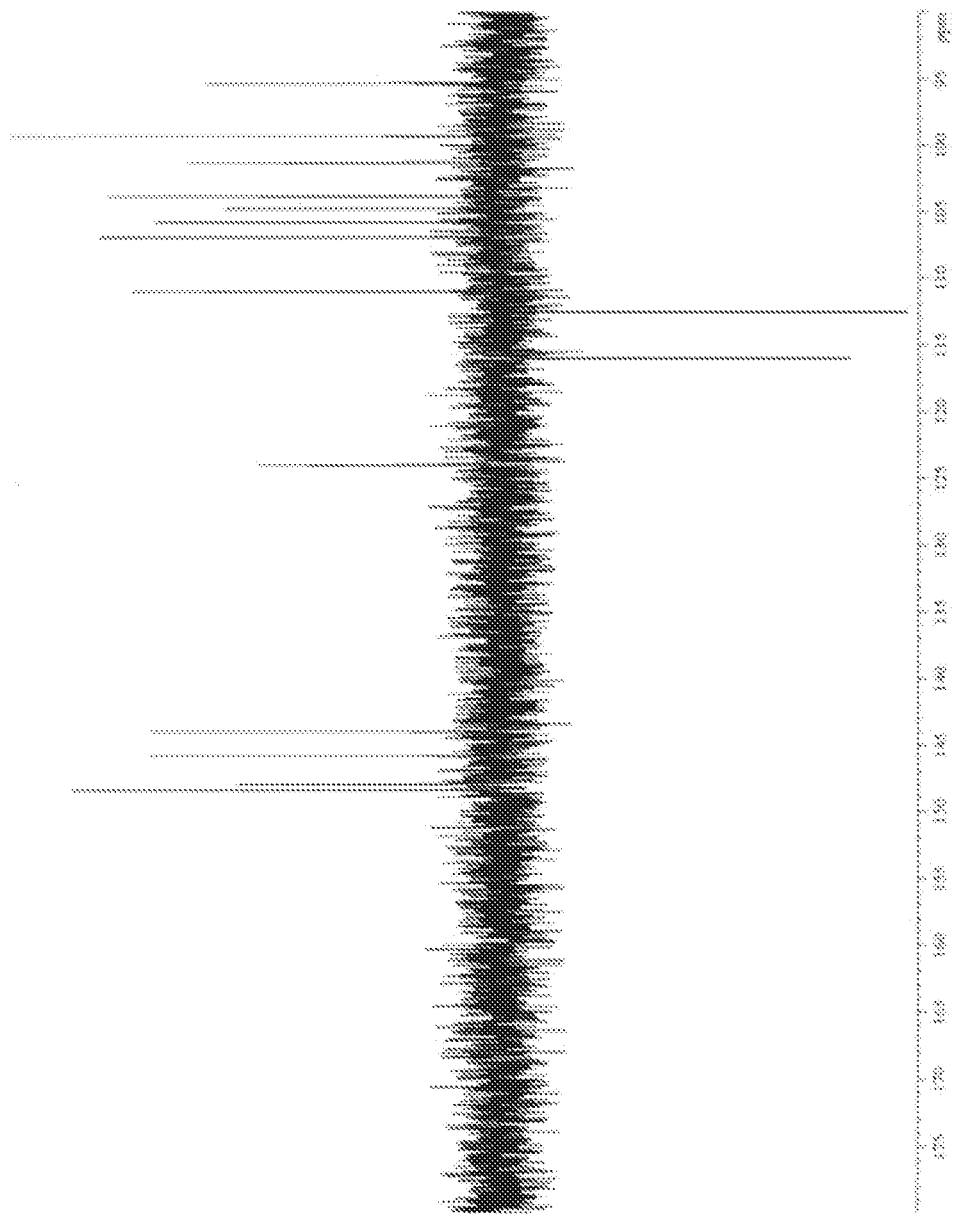
Figure 9D:
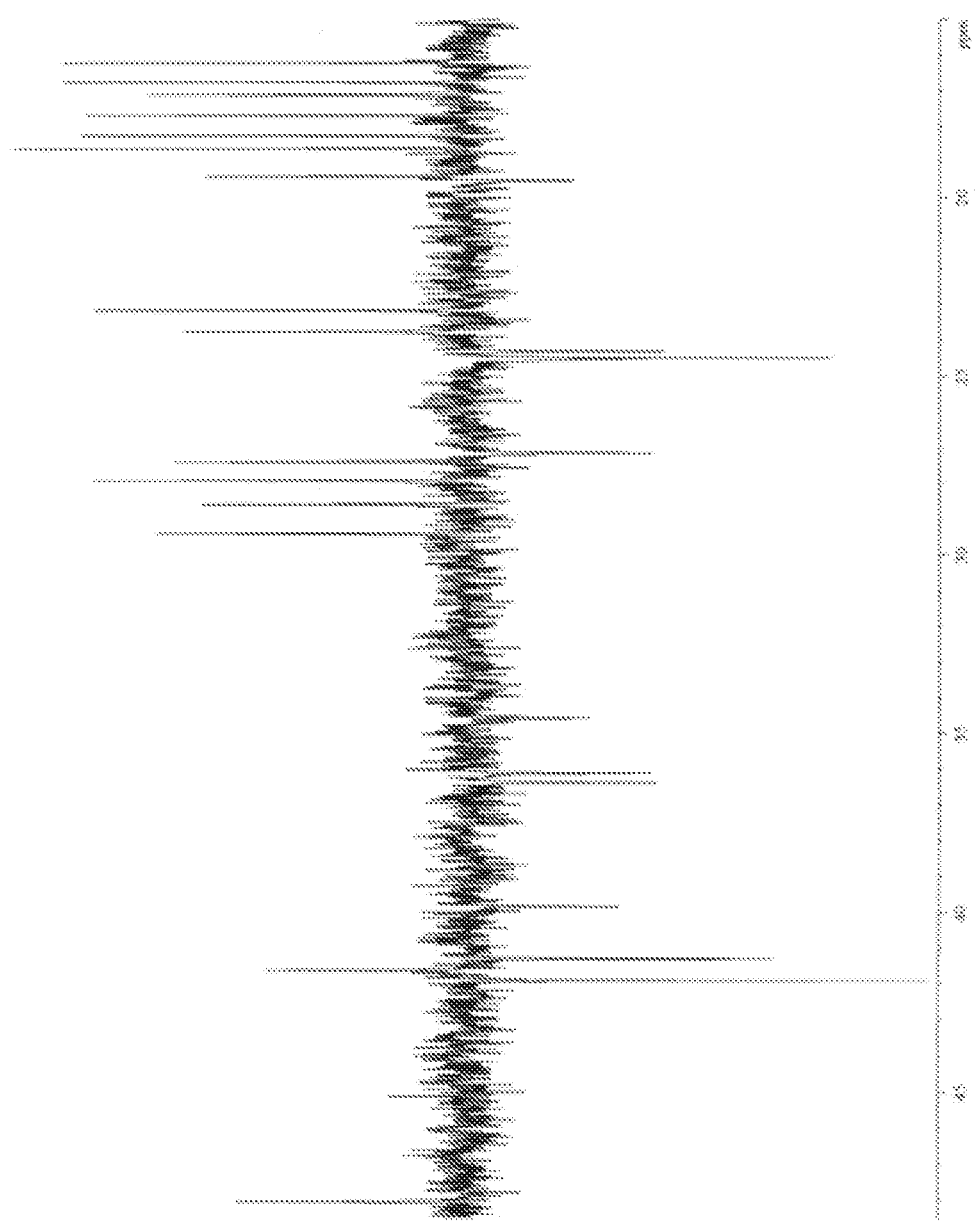
Figure 10A:
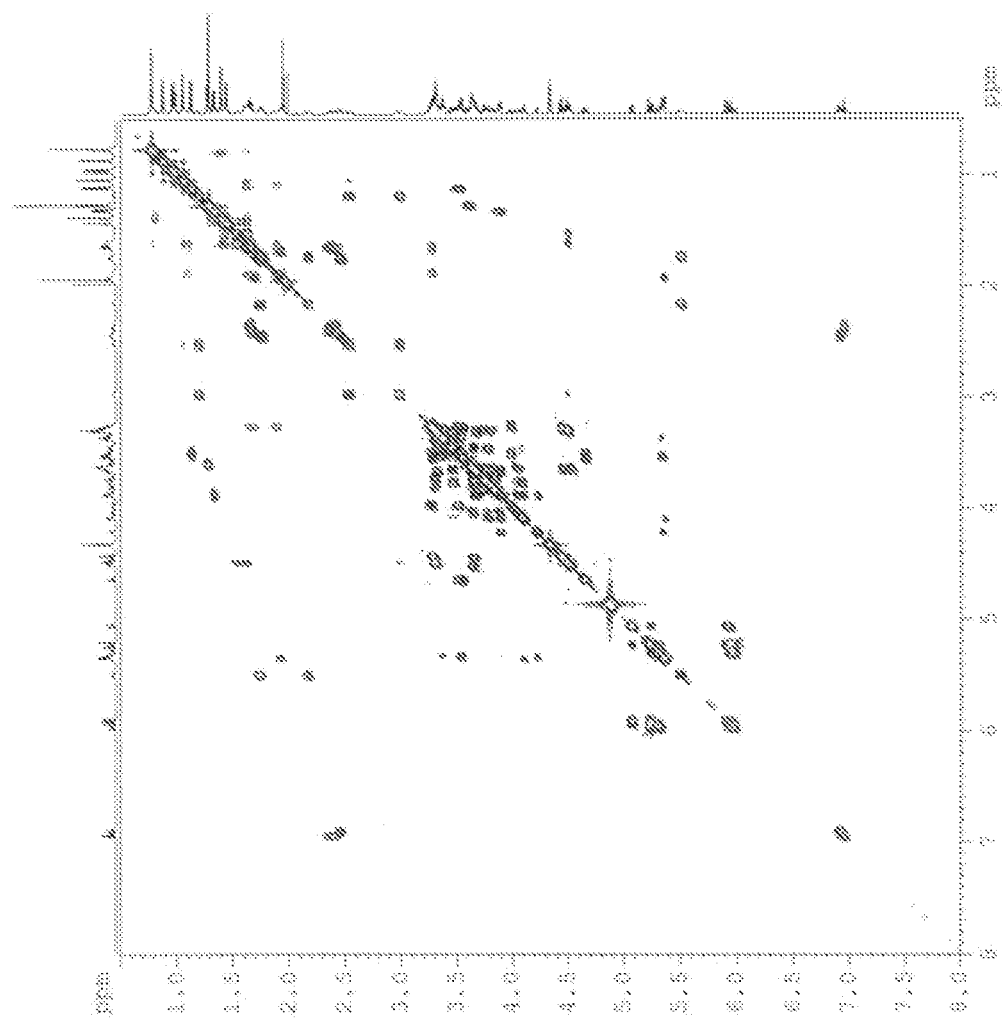
Figure 11A:
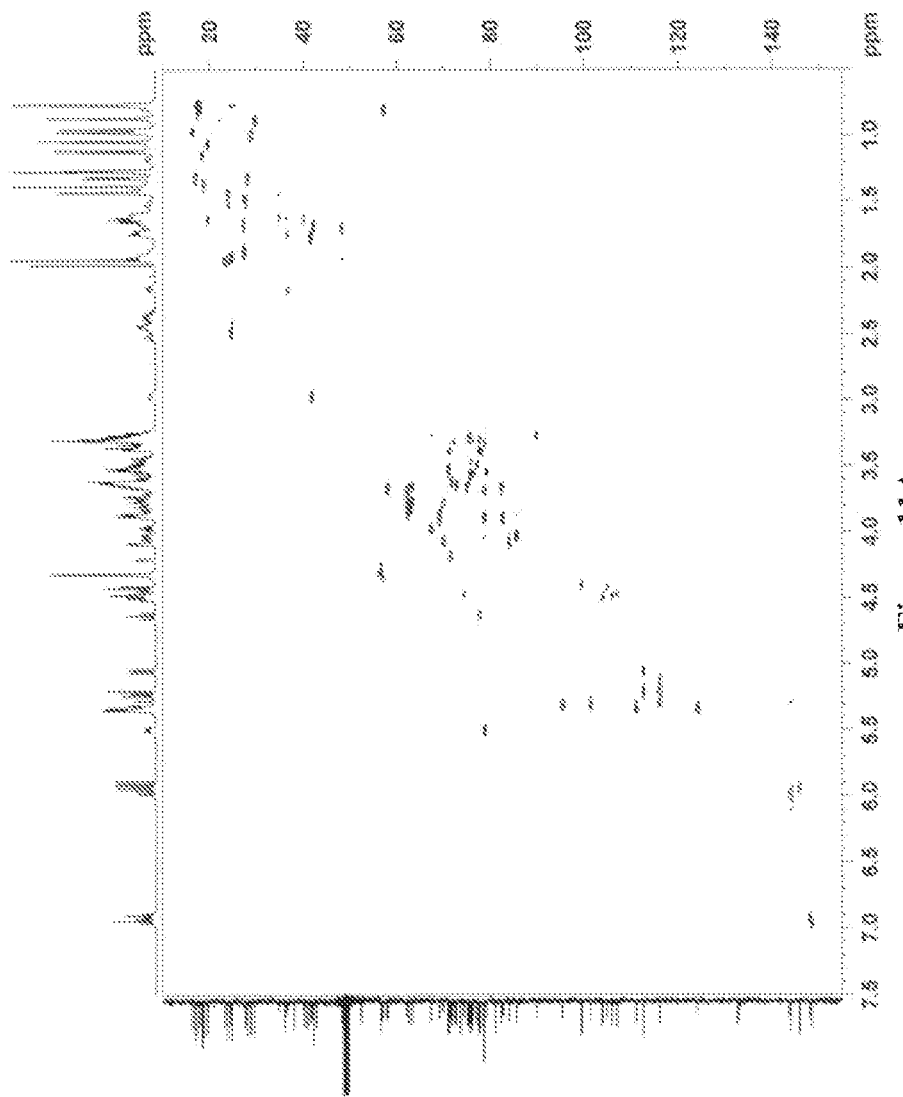
Figure 12A:
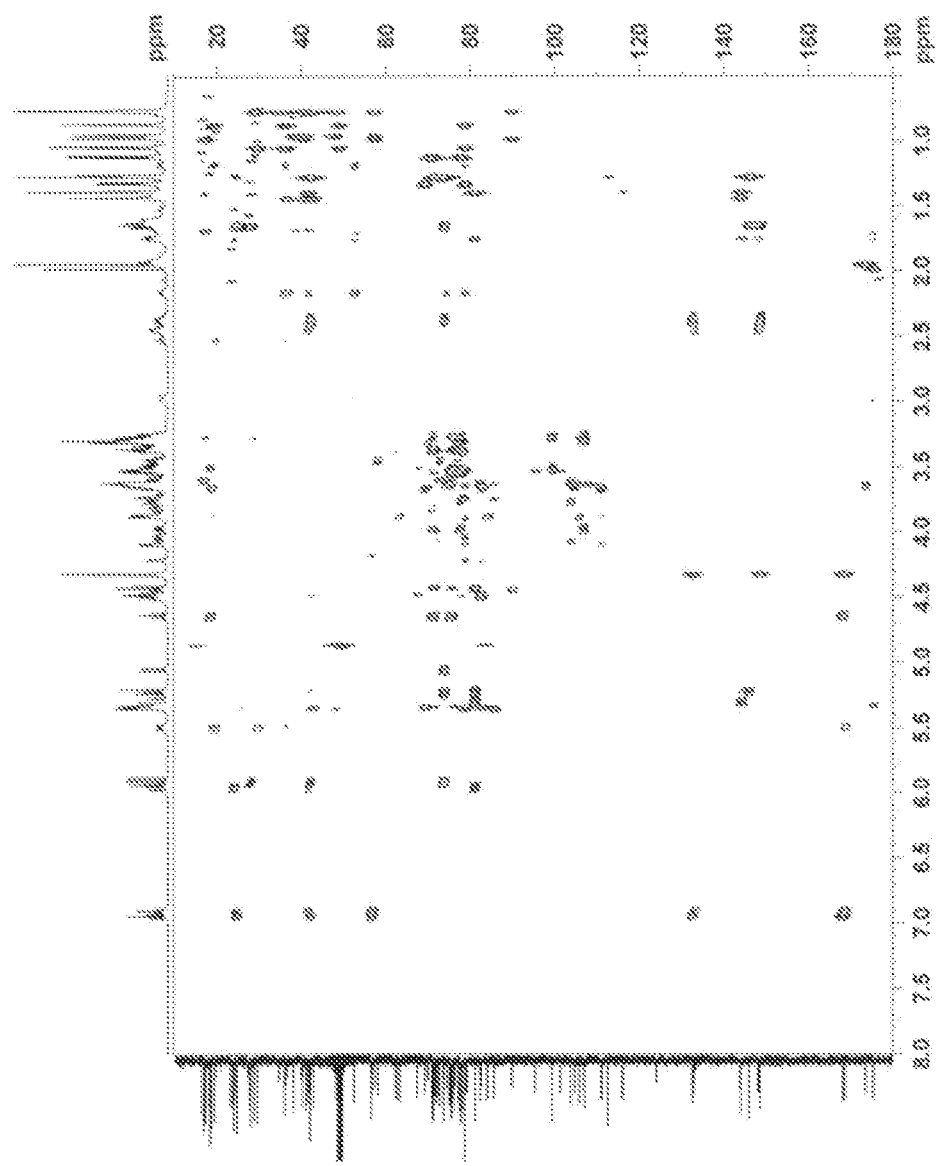
FIG. 12A-12E are HMBC spectra (500 MHz, CD$_3$OD) of Avicin D.
Figure 12B:
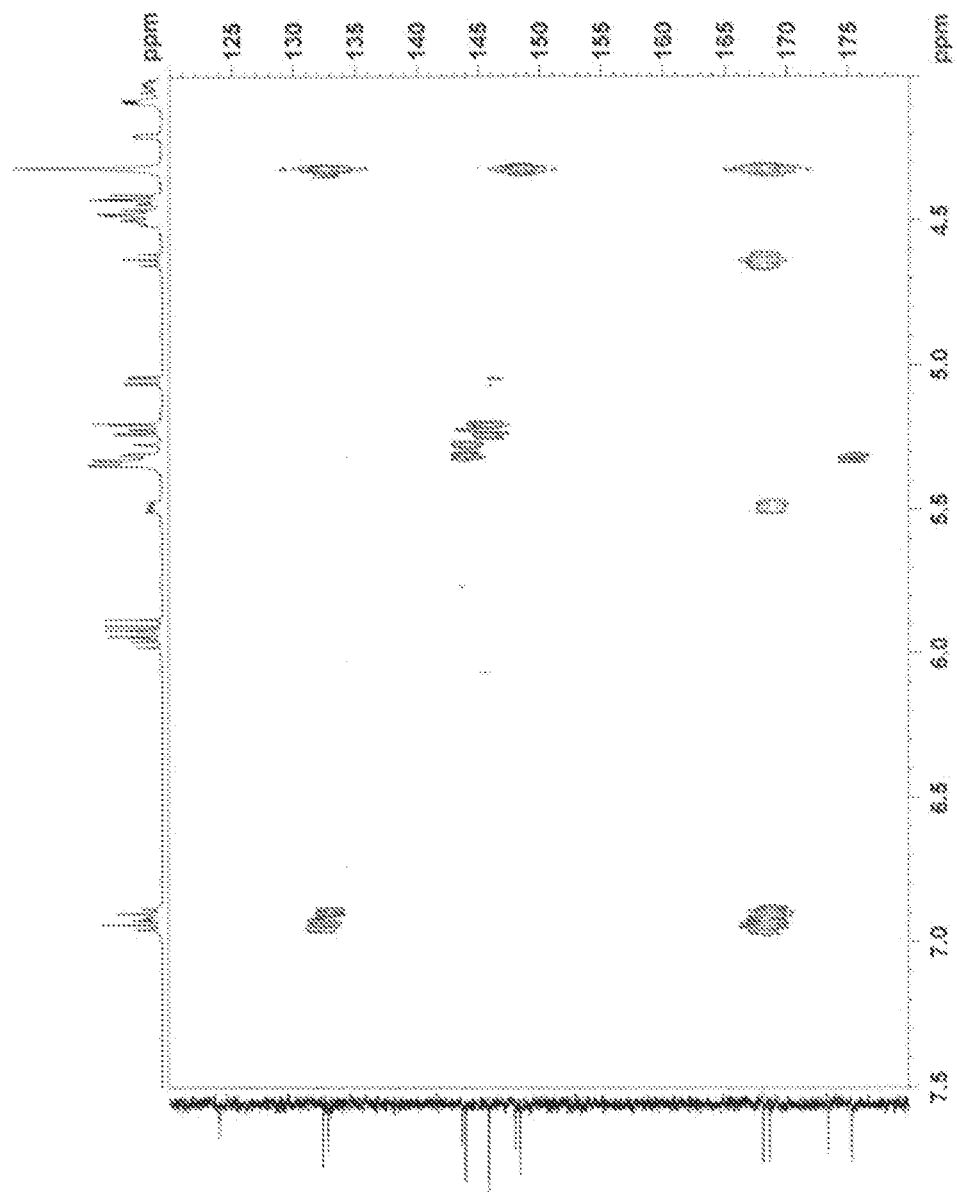
Figure 12C:
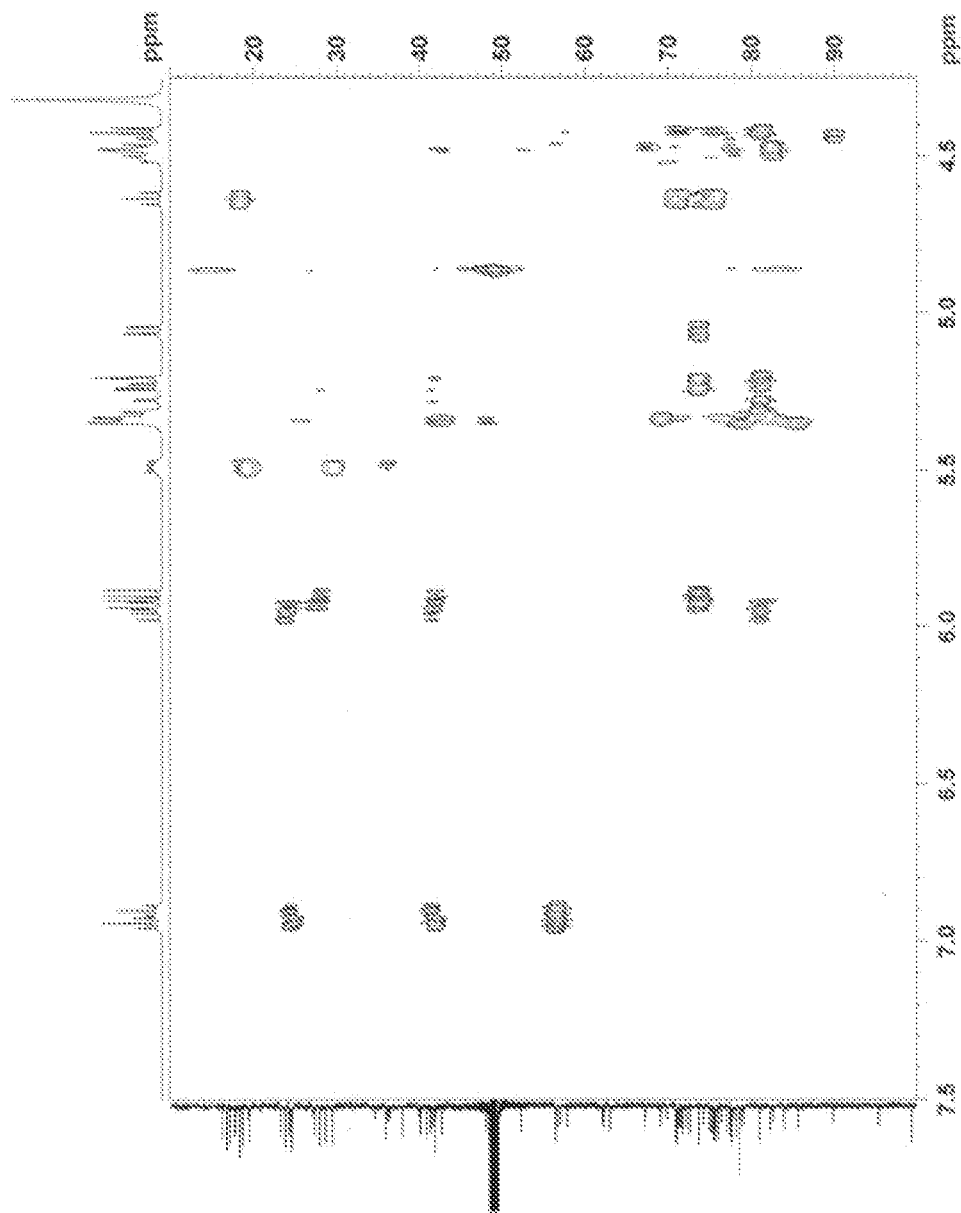
Figure 12D:
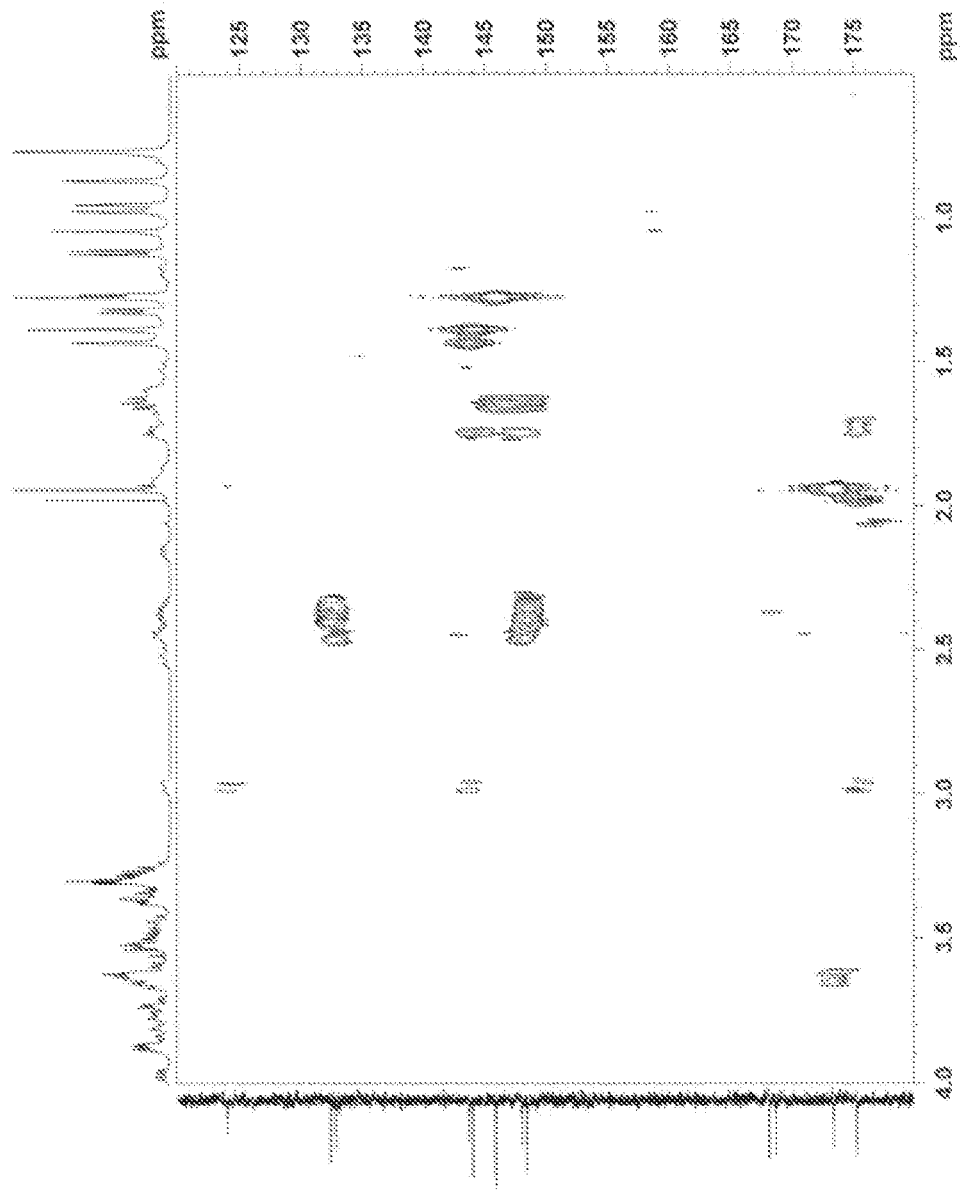
Figure 12E:
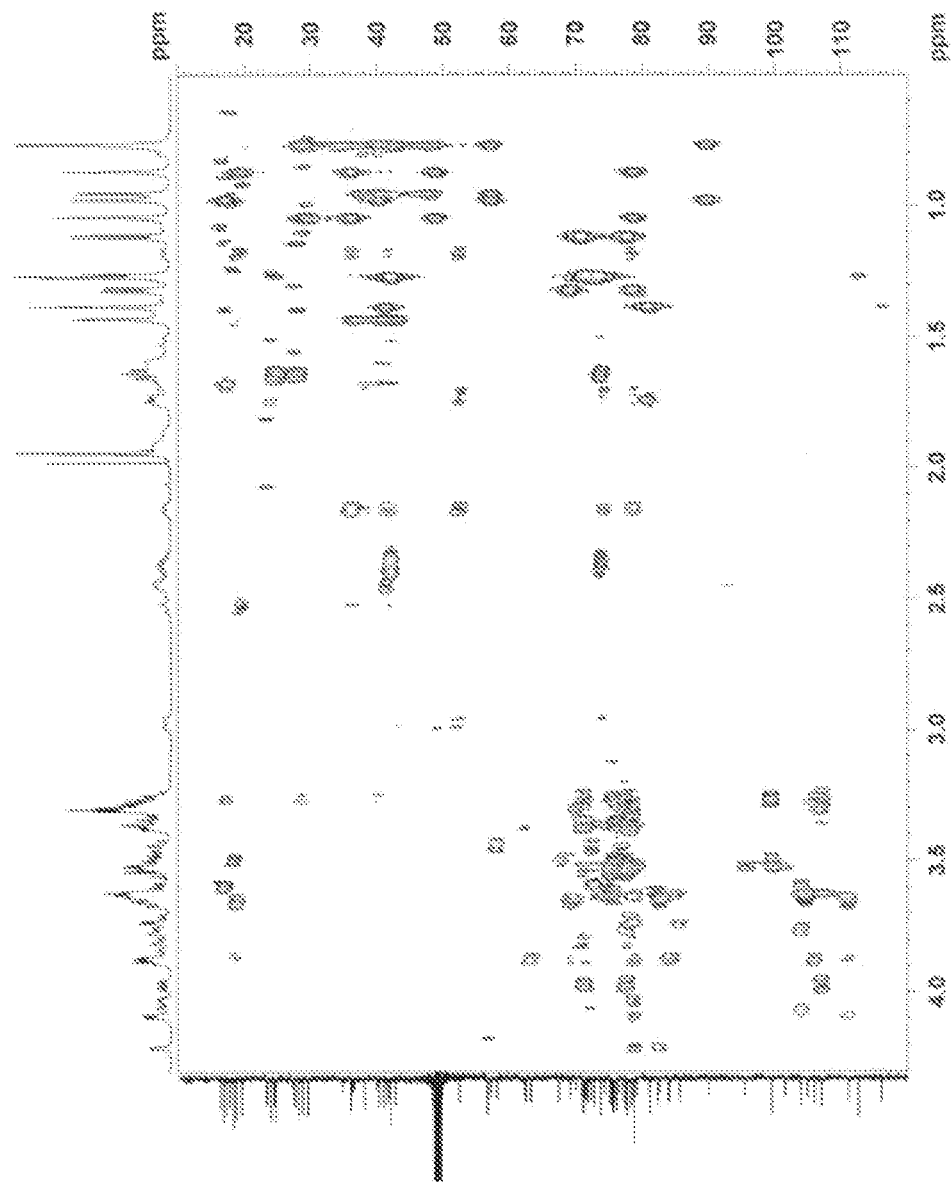
Figure 13A:
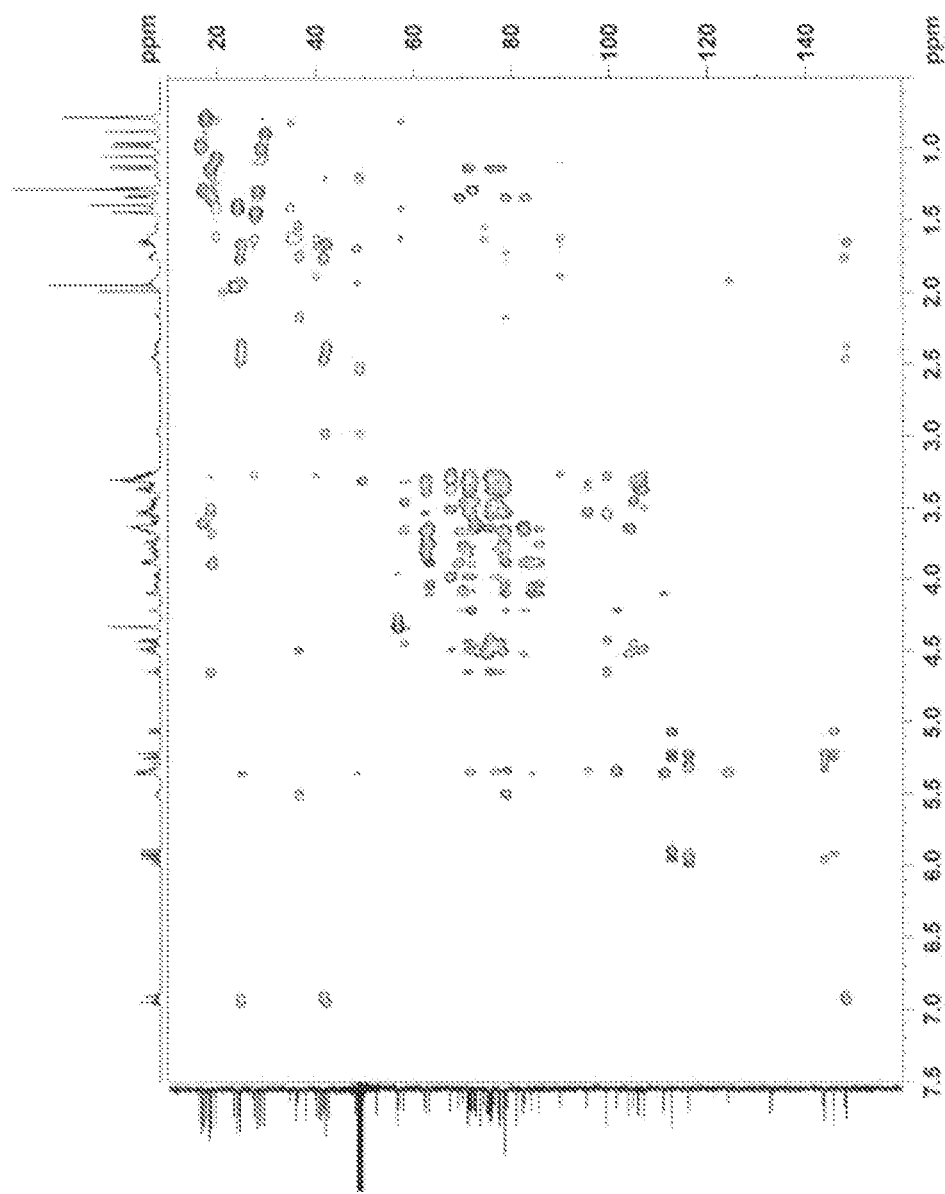
FIGS. 13A-13B are HSQC-TOCSY spectra (500 MHz, CD$_3$OD) of Avicin D.
Figure 13B:
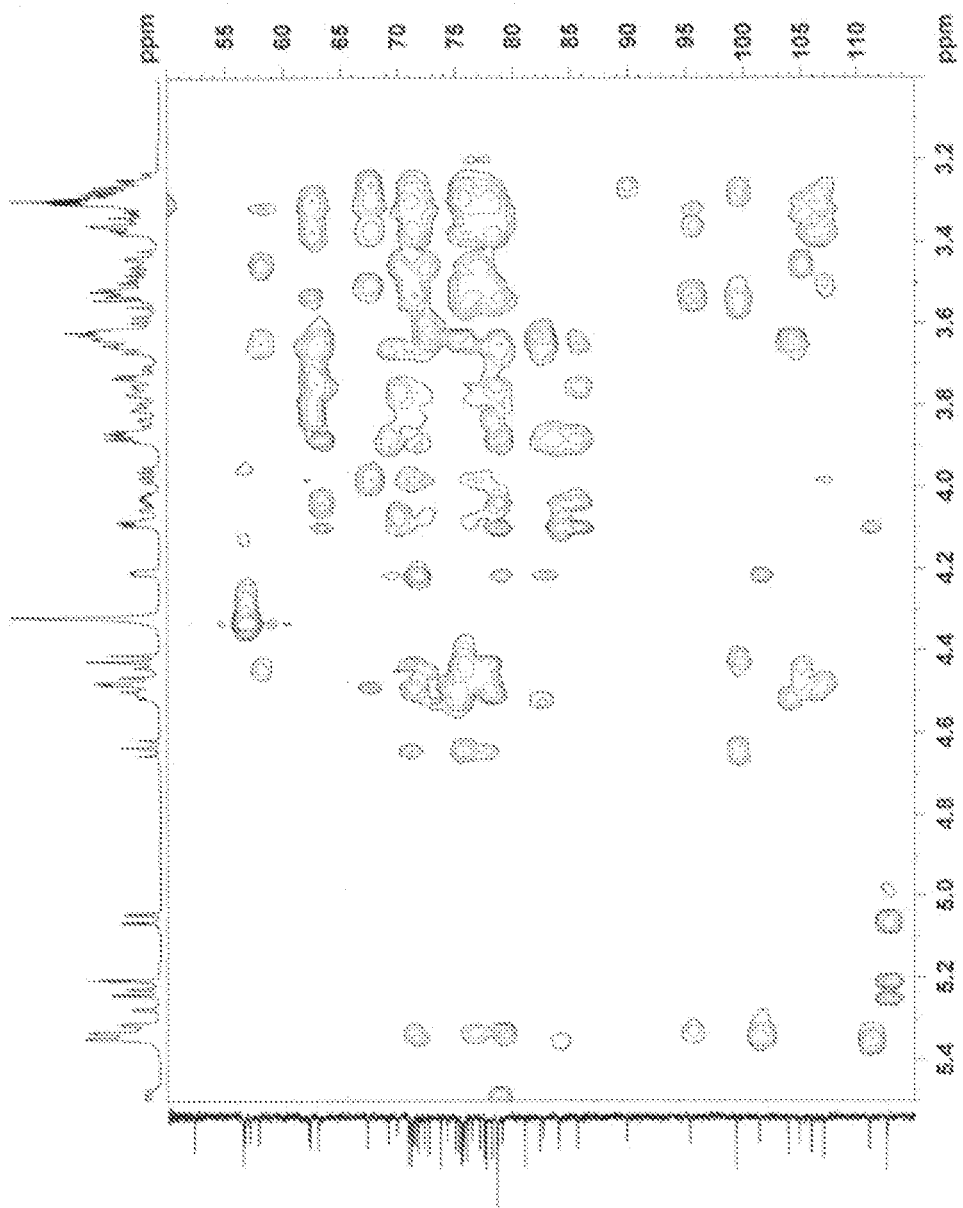
Figure 14A:
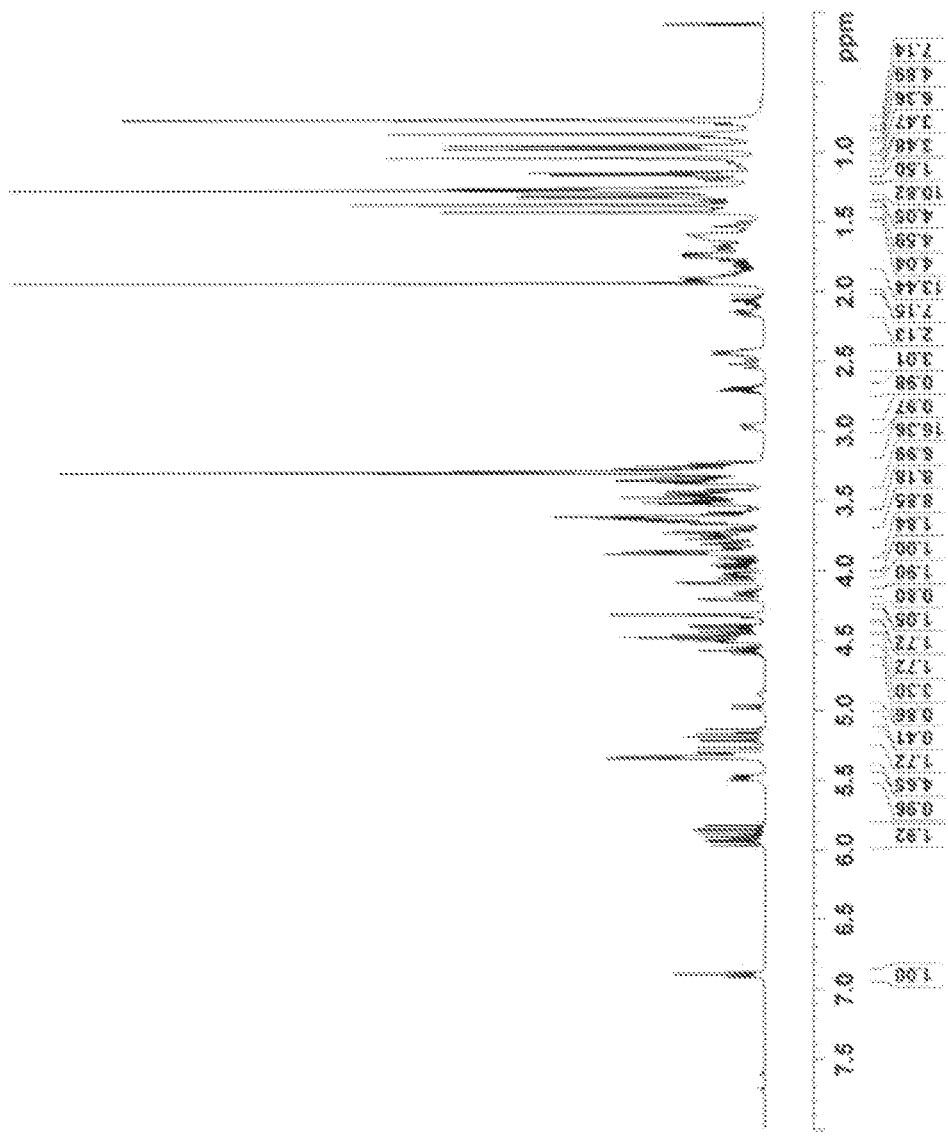
FIGS. 14A-14D are $^1$H NMR spectra (500 MHz, CD$_3$OD) of Compound 8.
Figure 14B:
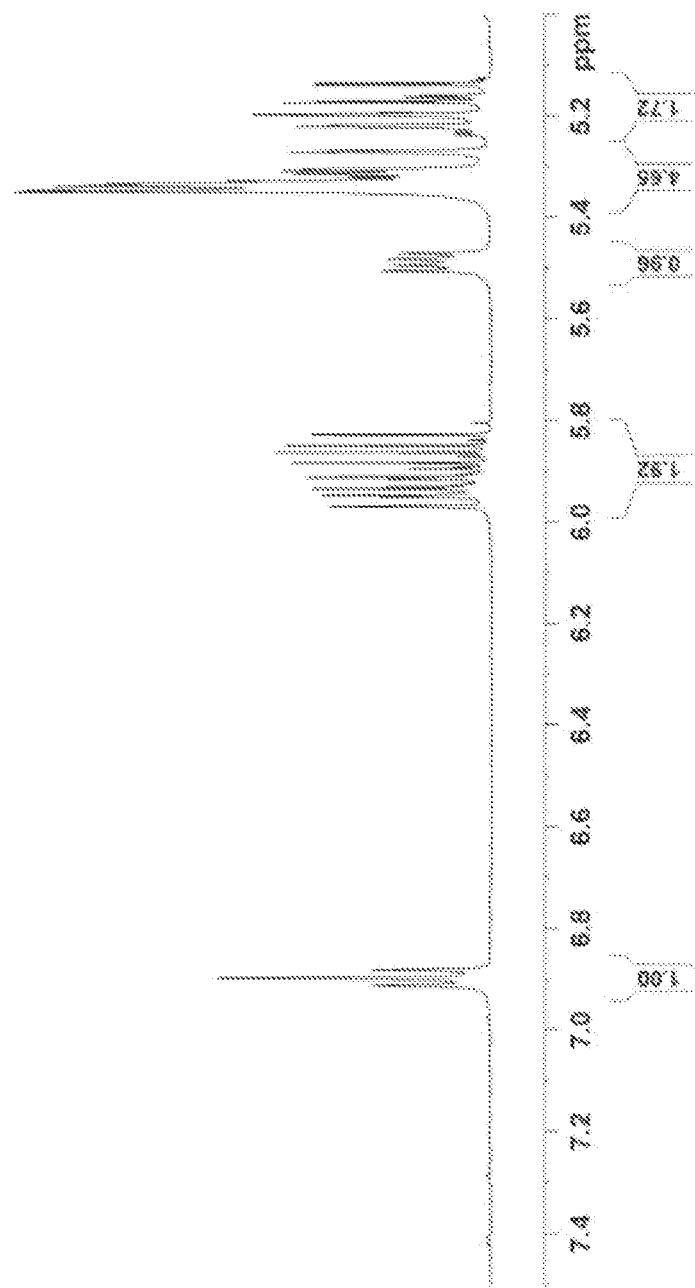
Figure 14C:
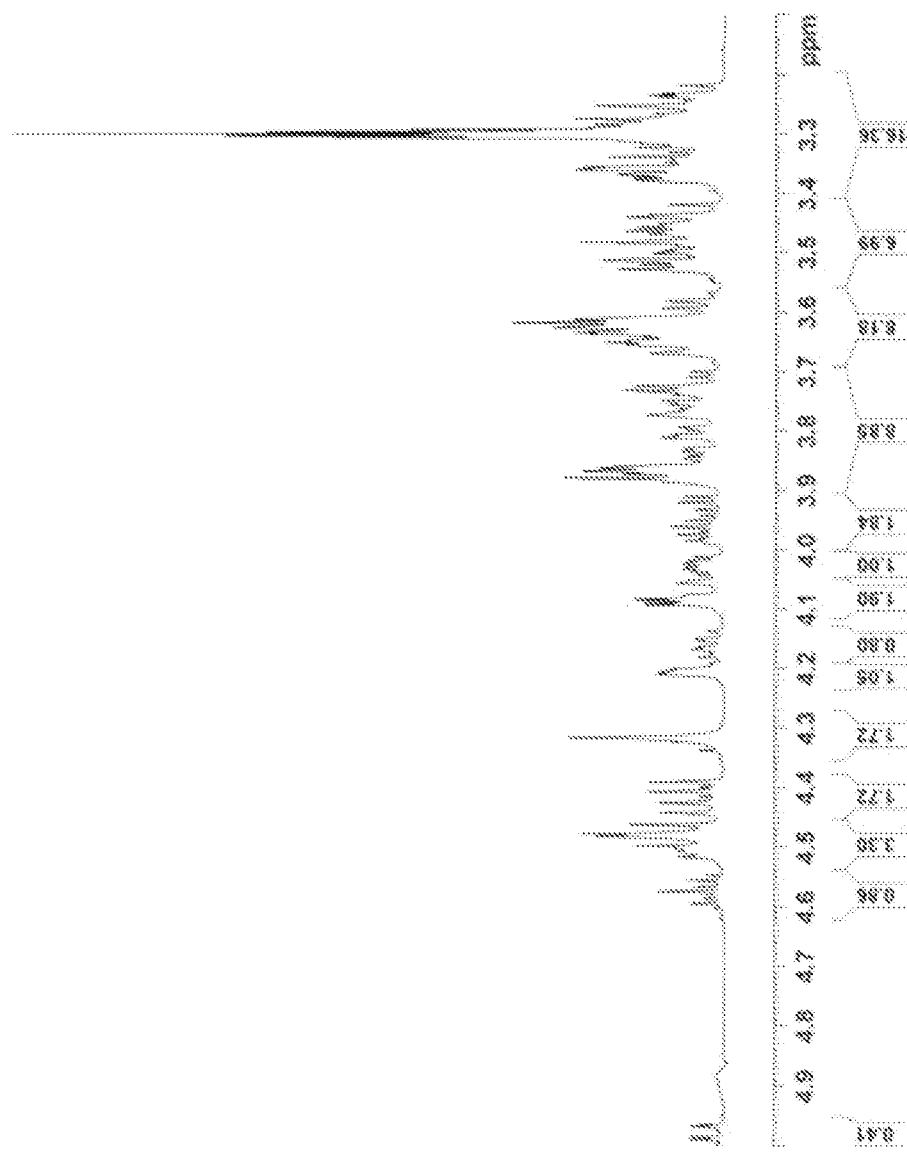
Figure 14D:
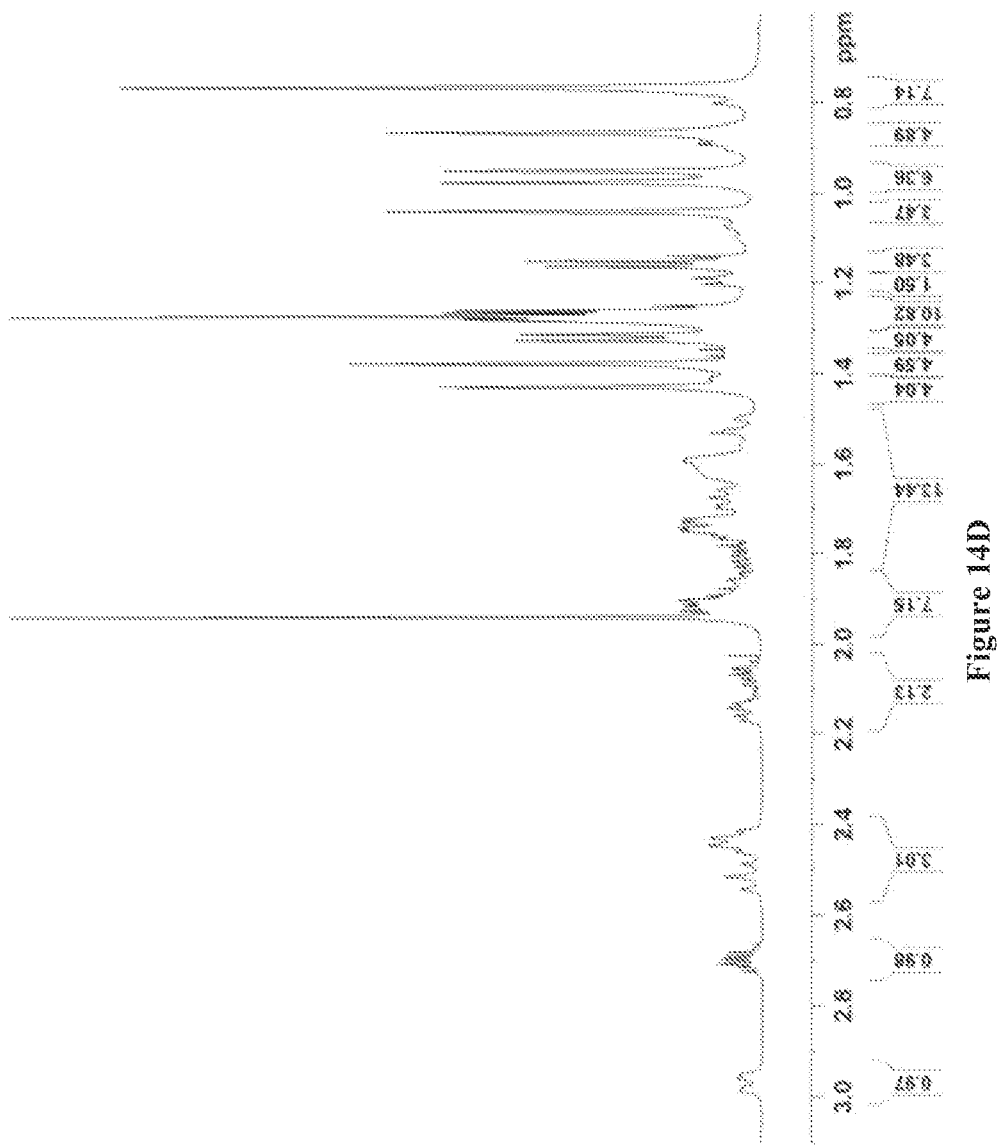
Figure 15A:
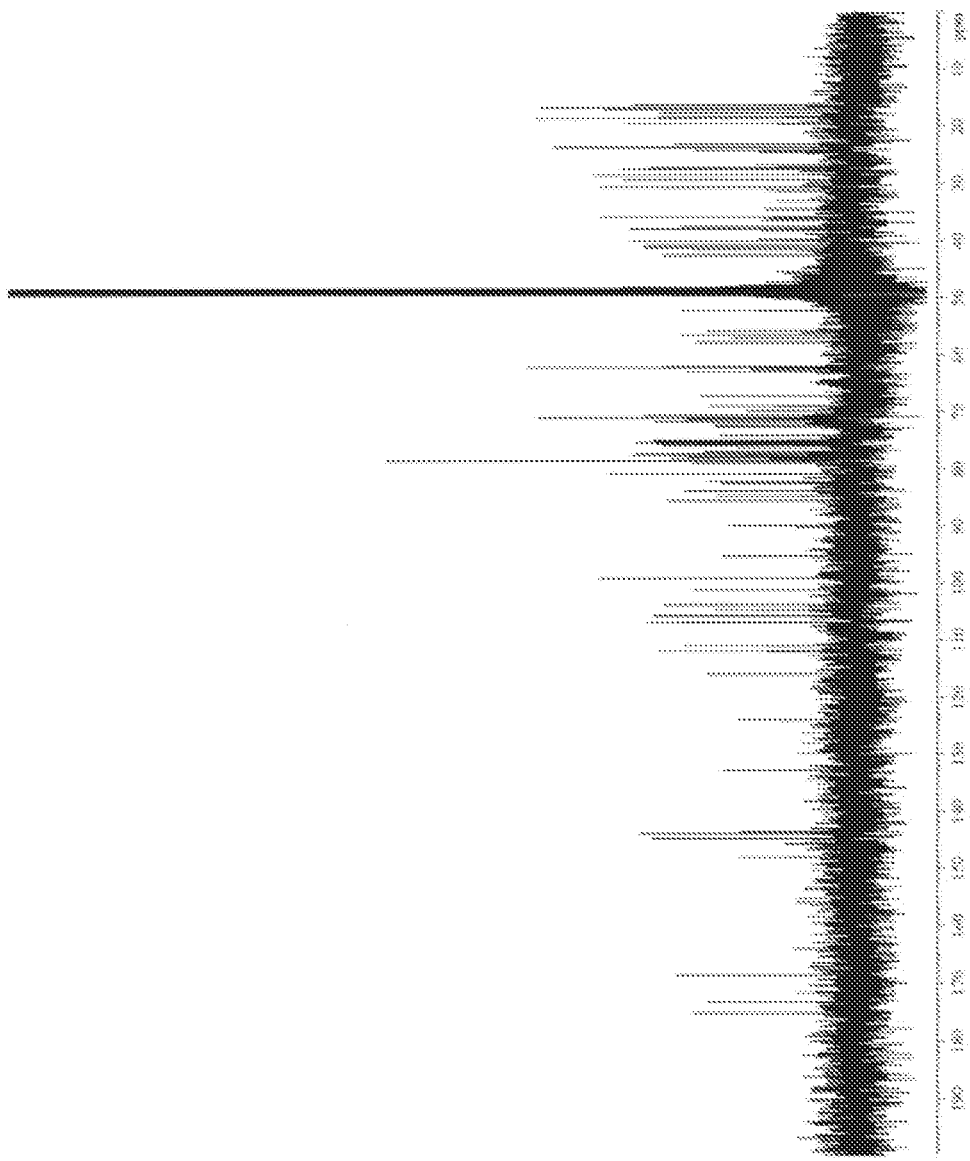
Figure 15C:
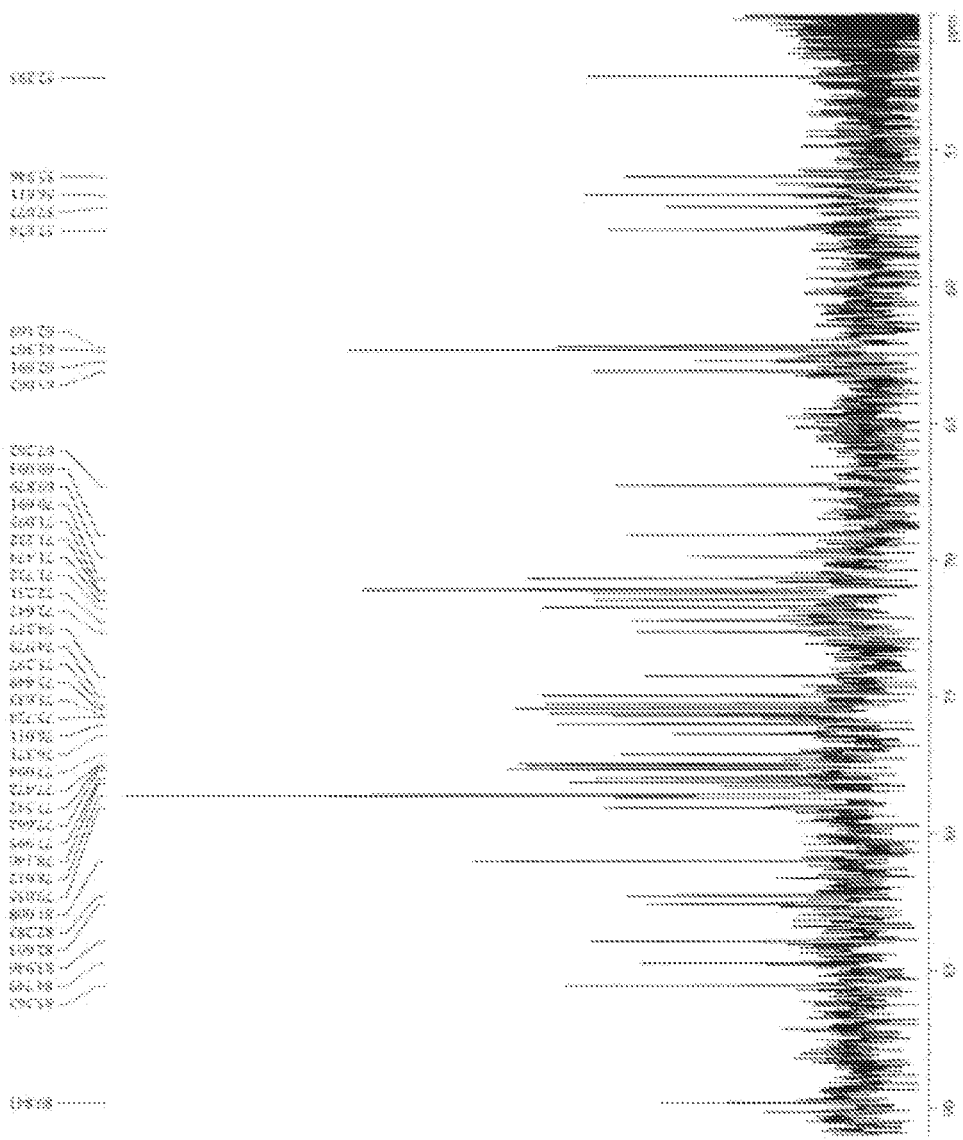
Figure 15D:
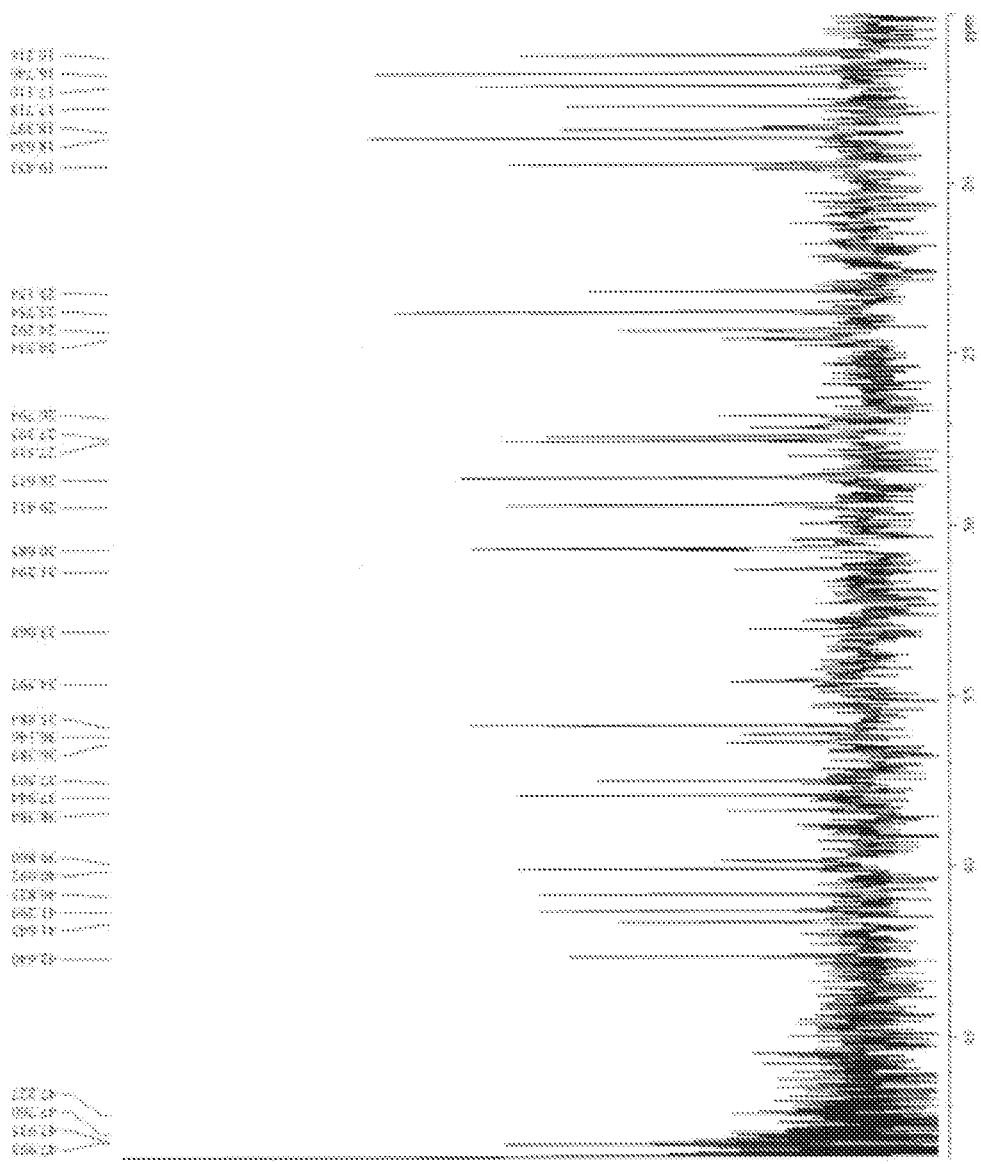

Compound 8 [ALB-151440] corresponds to the formula shown in FIG. 5 and the following chemical name:

(3S,4R,5S,6S)-6-(((3S,E)-8-((3S,4aR,5R,6aS,6bR,10S,12aR)-10-((2R,3S,4R,5S)-3-acetamido-6-(((2R,3S,4S,5R)-4,5-dihydroxy-6-methyl-3-((2S,3S,4S,5R)-3,4,5-trihydroxytetrahydro-2H-pyran-2-yloxy)tetrahydro-2H-pyran-2-yloxy)methyl)-4,5-dihydroxytetrahydro-2H-pyran-2-yloxy)-4a-(((2S,3S,4S,5S)-3-((2S,3R,4S,5S)-5-((2S,3S,5S)-3,4-dihydroxy-5-(hydroxymethyl)tetrahydrofuran-2-yloxy)-3-hydroxy-6-methyl-4-((2S,3S,4S,5S)-3,4,5-trihydroxy-6-(hydroxymethyl)tetrahydro-2H-pyran-2-yloxy)tetrahydro-2H-pyran-2-yloxy)-4,5-dihydroxy-6-(hydroxymethyl)tetrahydro-2H-pyran-2-yloxy)carbonyl)-5-hydroxy-2,2,6a,6b,9,9,12a-heptamethyl-1,2,3,4,4a,5,6,6a,6b,7,8,8a,9,10,11,12,12a,12b,13,14b-icosahydropicen-3-yloxy)-7-(hydroxymethyl)-3-methyl-8-oxoocta-1,6-dien-3-yloxy)-4,5-dihydroxy-2-methyltetrahydro-2H-pyran-3-yl 2-(3-hydroxy-3-methylpent-4-enyl)oxetane-3-carboxylate.

This compound was synthesized as follows:

A solution of Avicin D (1.0 g, 0.48 mmol) in 50 mM phosphate buffer (pH 7.4, 75 mL) and acetonitrile (340 mL) was heated at 55° C. for 17 h. The mixture was concentrated under reduced pressure to remove acetonitrile. Particulate matter was removed by centrifugation (3500 rpm, 15 min) and the supernatant was loaded onto a pre-conditioned Alltech C18 SPE cartridge (10 g). The cartridge was washed with water (100 mL) and then methanol (150 mL). The methanol elute was concentrated under reduced pressure to ca. 40 mL volume and the oxetane derivative was purified by preparative HPLC.

Column—Waters SunFire C18 OBD (150×50 mm, 5 μm)

Column temperature—Ambient

Solvents—A (water+0.1% formic acid) B (acetonitrile+0.1% formic acid)

Gradient—Linear (20% B to 45% B within 25 min).

Flowrate—100 mL/min and λ 220 nm

Pure fractions were combined and the acetonitrile was removed by evaporation under reduced pressure. Solvent exchange (water to methanol) and volume reduction was achieved by solid phase extraction (SPE) using C18 resin. The methanol elute was reduced to ca. 10 mL volume by evaporation under reduced pressure then water (50 mL) was added and the solvent was removed by lyophilization to afford Compound 8 (mixture of cis/trans isomers—at the oxetane, 84.9 mg, 8.5%) as a white solid.

Figure 23:
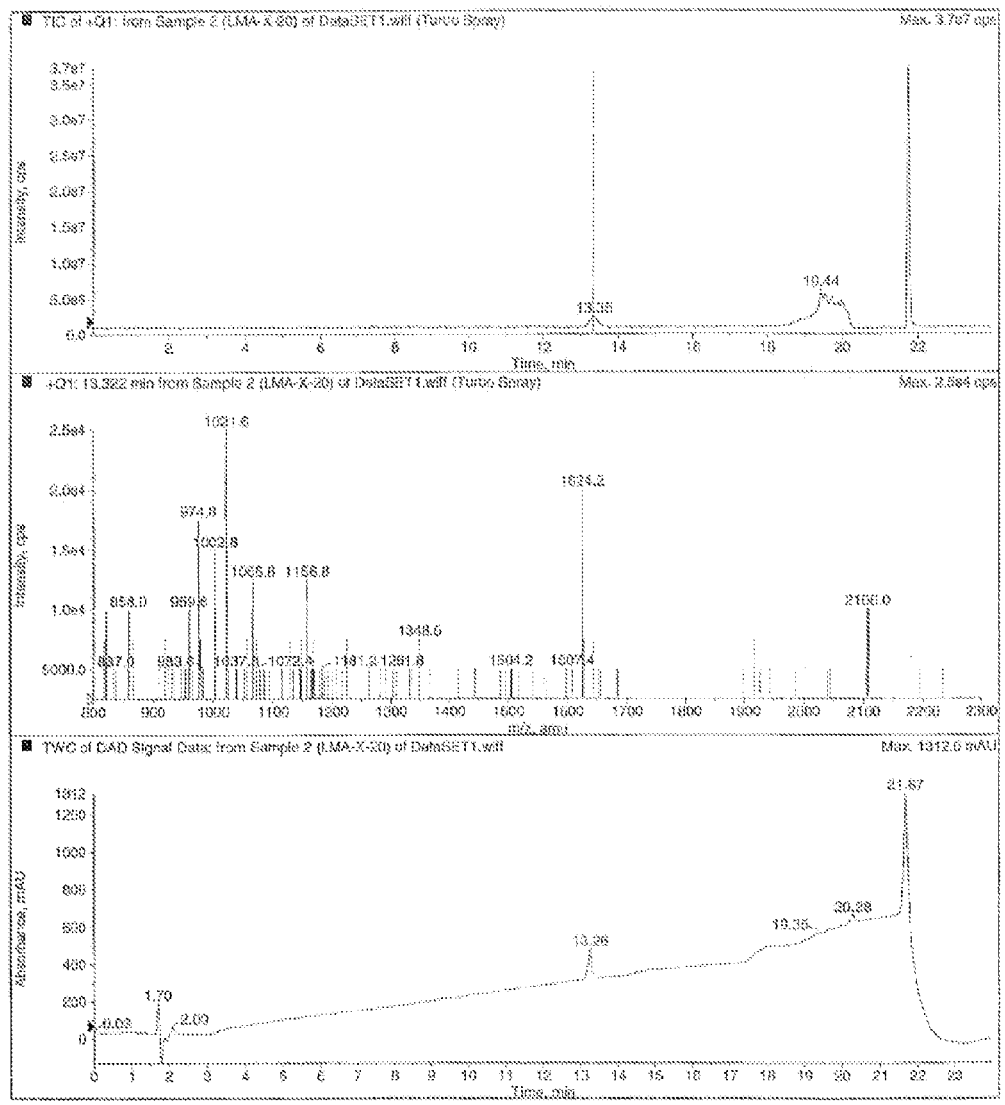
FIG. 23 is the mass spectrum of Compound 8 showing the molecular ion of 2106 corresponding to Compound 8 plus a sodium ion.
Figure 24:
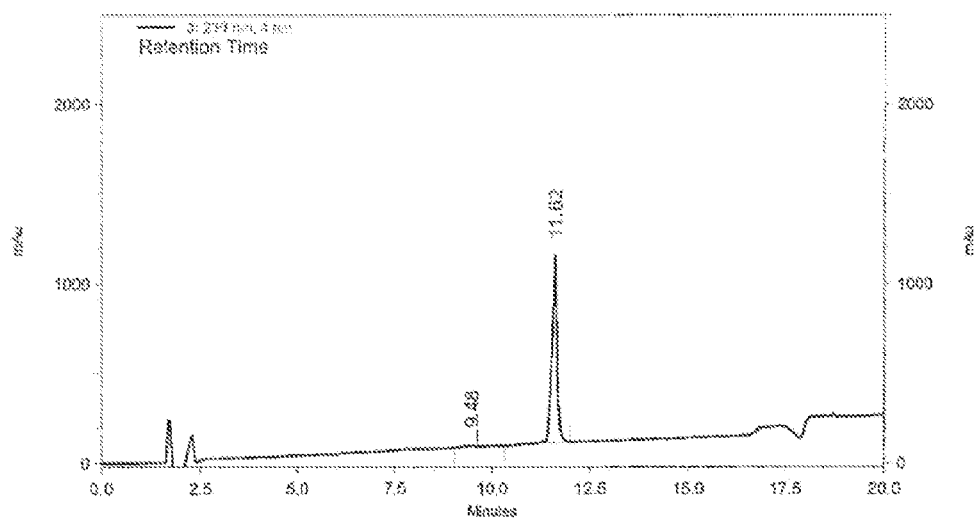
FIG. 24 is the HPLC trace of Compound 8 using a 230 nm diode array detector showing greater than 99% compound purity.
Figure 25:
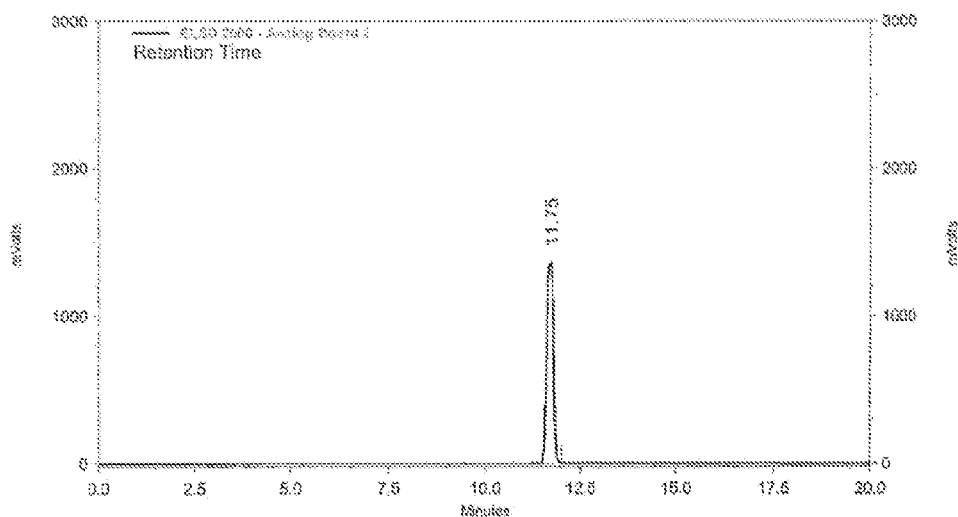
FIG. 25 is the HPLC trace Compound 8 using an ELS detector showing greater than 99% compound purity.

Compound 8 was characterized using $^1$H and $^{13}$C NMR including several 2-D NMR experiments (FIGS. 7-22), LCMS (FIG. 23), and HPLC (FIGS. 24 and 25).

LCMS
Column—SunFire C18 (150×4.6 mm, 3.5 μm particles)
Temperature—Ambient
Flow Rate—1.0 mL/min
Gradient

| Time (min) | Water (%) (0.1% formic acid) | Acetonitrile (%) (0.1% formic acid) |
| --- | --- | --- |
| 0 | 90 | 10 |
| 15 | 40 | 60 |
| 16 | 5 | 95 |
| 19 | 5 | 95 |
| 19.1 | 90 | 10 |
| 24 | 90 | 10 |

Detection—230 nm, MS with turbo ion spray ionization
HPLC
Column—SunFire C18 (150×4.6 mm, 3.5 μm particles)
Temperature—Ambient
Flow Rate—1.0 mL/min
Gradient

| Time (min) | Water (%) (0.1% formic acid) | Acetonitrile (%) (0.1% formic acid) |
| --- | --- | --- |
| 0 | 90 | 10 |
| 15 | 40 | 60 |
| 16 | 5 | 95 |
| 19 | 5 | 95 |
| 19.1 | 90 | 10 |
| 24 | 90 | 10 |

Figure 26:
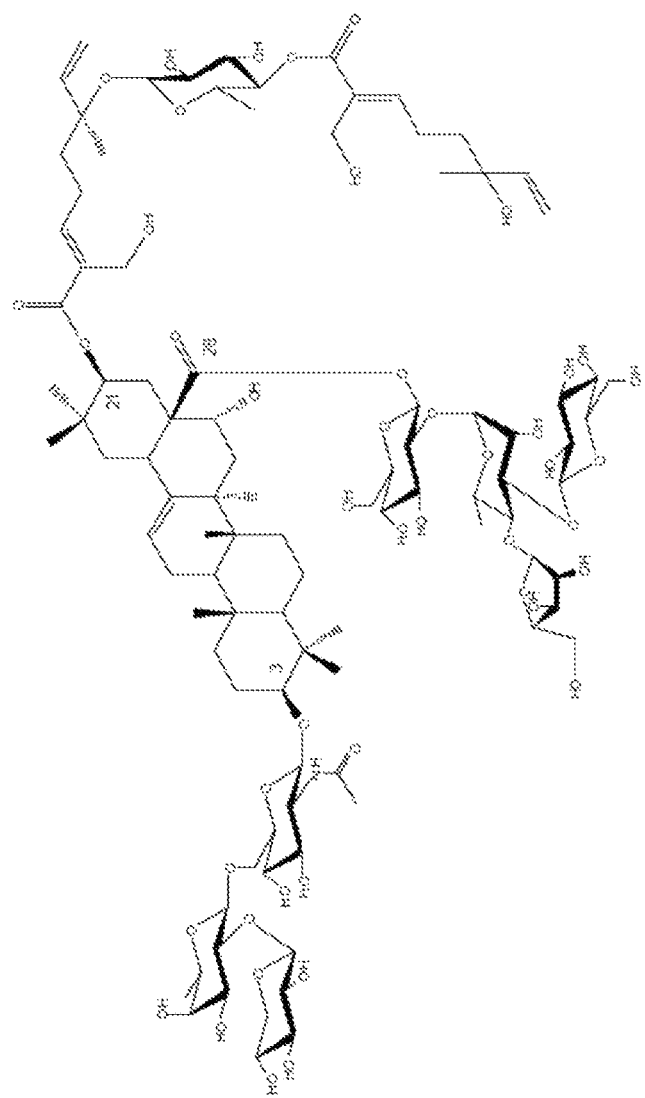
FIG. 26 shows the structure of Avicin D showing all bonds and stereochemistry in the sugar rings.

Detection—Photodiode array from 190 nm-370 nm (extraction at 230 nm); ELSD, 120° C., 3.0 L/min nitrogen NMR Analysis of Avicin D and Compound A sample of Avicin D (16.7 mg) was dissolved in 0.5 mL of CD$_3$OD and used to acquire NMR data. A series of NMR experiments including $^1$H NMR (FIG. 7), $^{13}$C NMR (FIG. 8), Dept-135 (FIG. 9), $^1$H-$^1$H COSY (FIG. 10), HSQC (FIG. 11), HMBC (FIG. 12), and HSQC-TOCSY (FIG. 13) were performed to allow assignment of the Avicin D sample and provide a reference for structural characterization of the metabolite. The spectra were acquired on a Bruker 500 MHz Avance DRX spectrometer and referenced to the residual solvent signal ($\delta_H$ 3.30, $\delta_C$ 49.0 for CD$_3$OD). A complete NMR assignment of Avicin D (shown in FIG. 26) was undertaken for comparison with the literature data and is discussed in detail below.

Figure 21B:
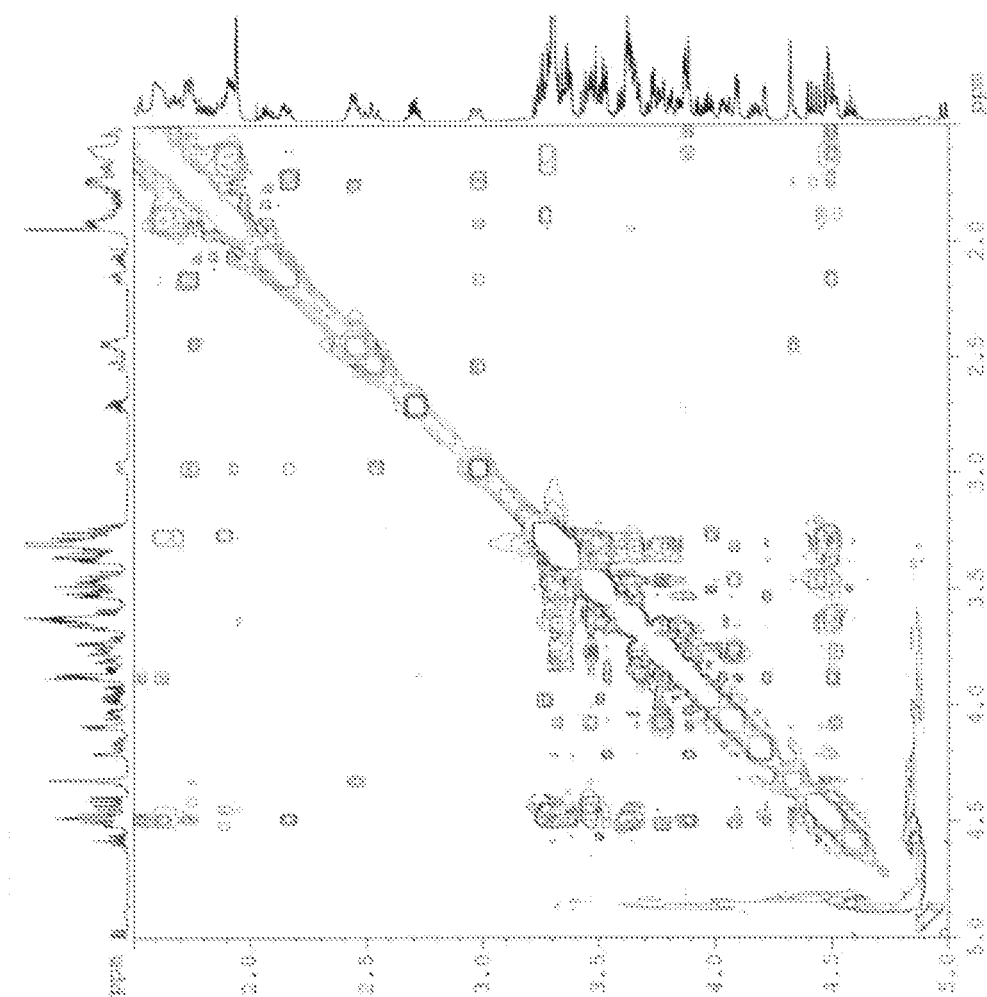
Figure 22:
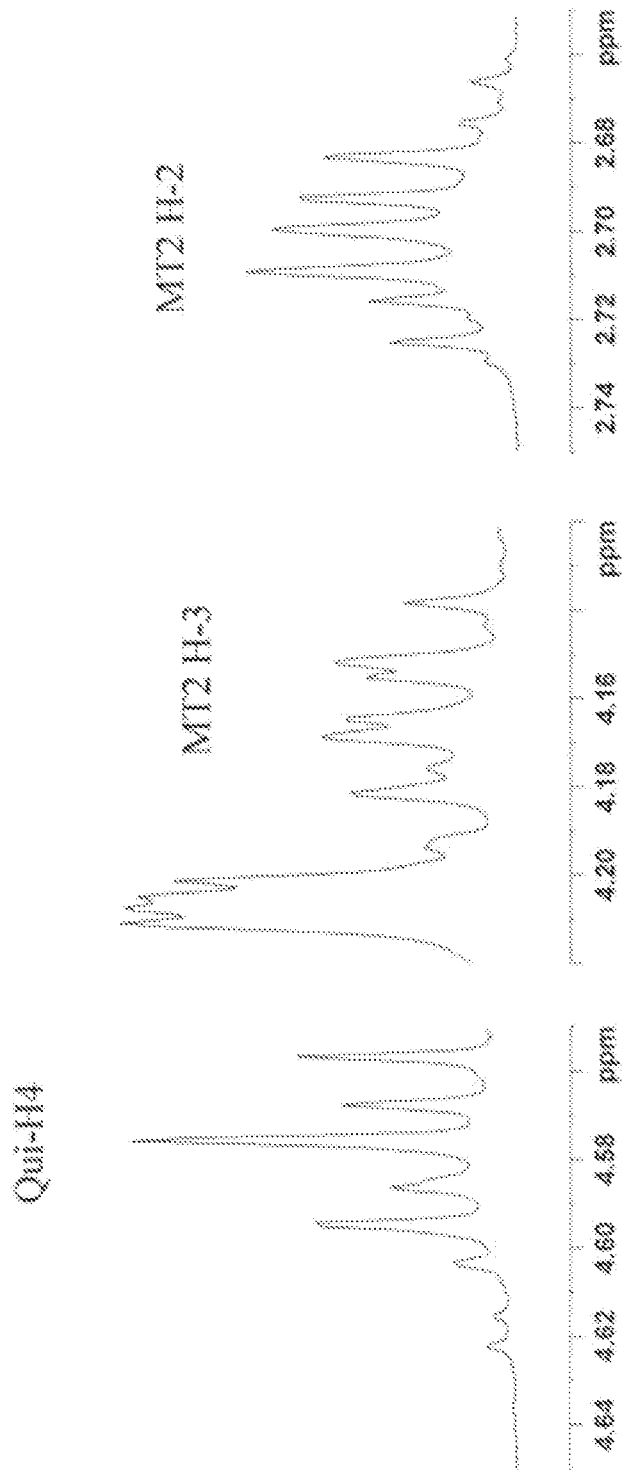
FIG. 22 is an expansion of the $^1$H NMR spectrum of Compound 8, showing the multiplets for the MT2 H-2 and H-3 protons and H-4 of the Qui residue.

A similar set of NMR experiments including $^1$H NMR (FIG. 14), $^{13}$C NMR (FIG. 15), Dept-135 (FIG. 16), $^1$H-$^1$H COSY (FIG. 17), HSQC (FIG. 18), and HMBC (FIG. 19), and HSQC-TOCSY (FIG. 20) were acquired using a 5.9 mg sample of the metabolite, Compound 8 in 0.5 mL CD$_3$OD. In addition, a 2-D NOESY spectrum was also acquired for the metabolite to assist in determination of the relative configuration of the metabolite (FIG. 21). These spectra were also acquired on a Bruker 500 MHz Avance DRX spectrometer and referenced to the residual solvent signal ($\delta_H$ 3.30, $\delta_C$ 49.0 for CD$_3$OD). A complete NMR assignment of the metabolite was undertaken using the data acquired for Avicin D, as well as literature data, as a reference and is discussed in detail below.

Figure 27:
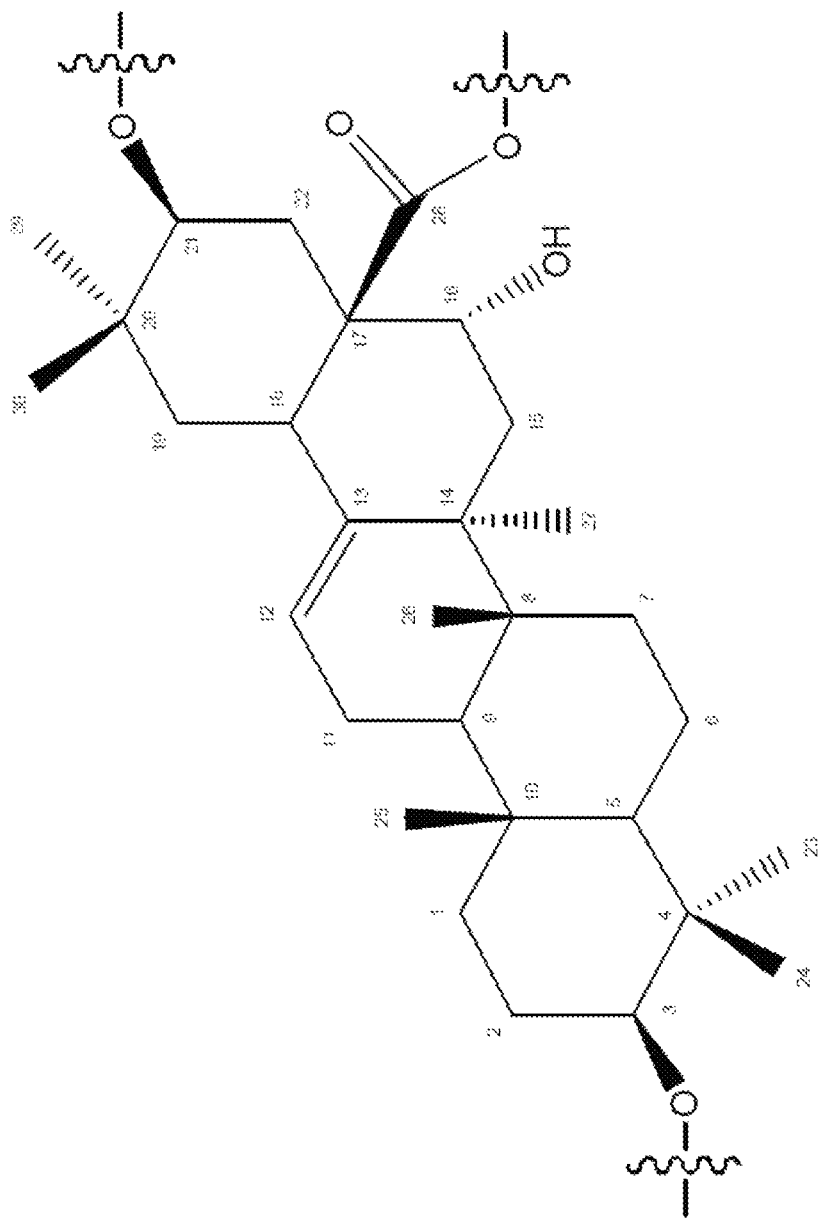
FIG. 27 shows the molecular formula of the aglycone region of Avicin D.
Figure 29:
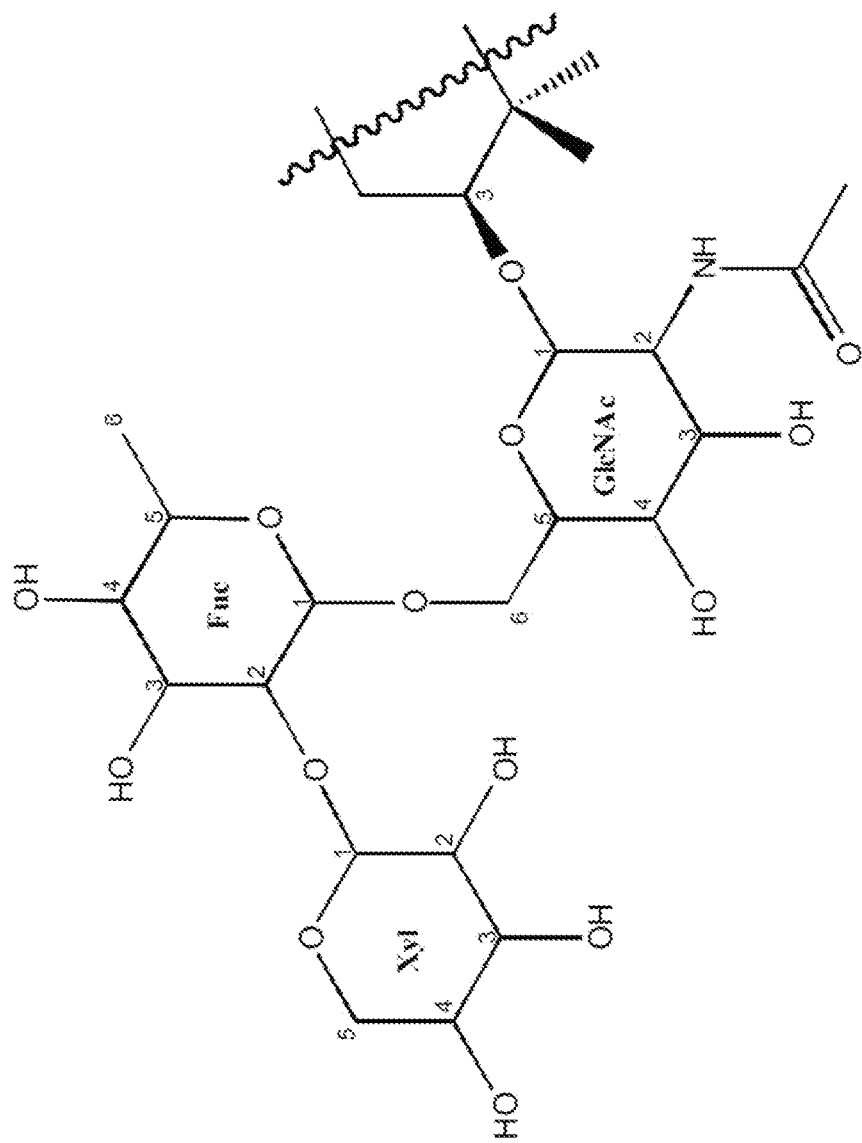
FIG. 29 shows the molecular formula of C-3 glycoside region of Avicin D.
Figure 31:
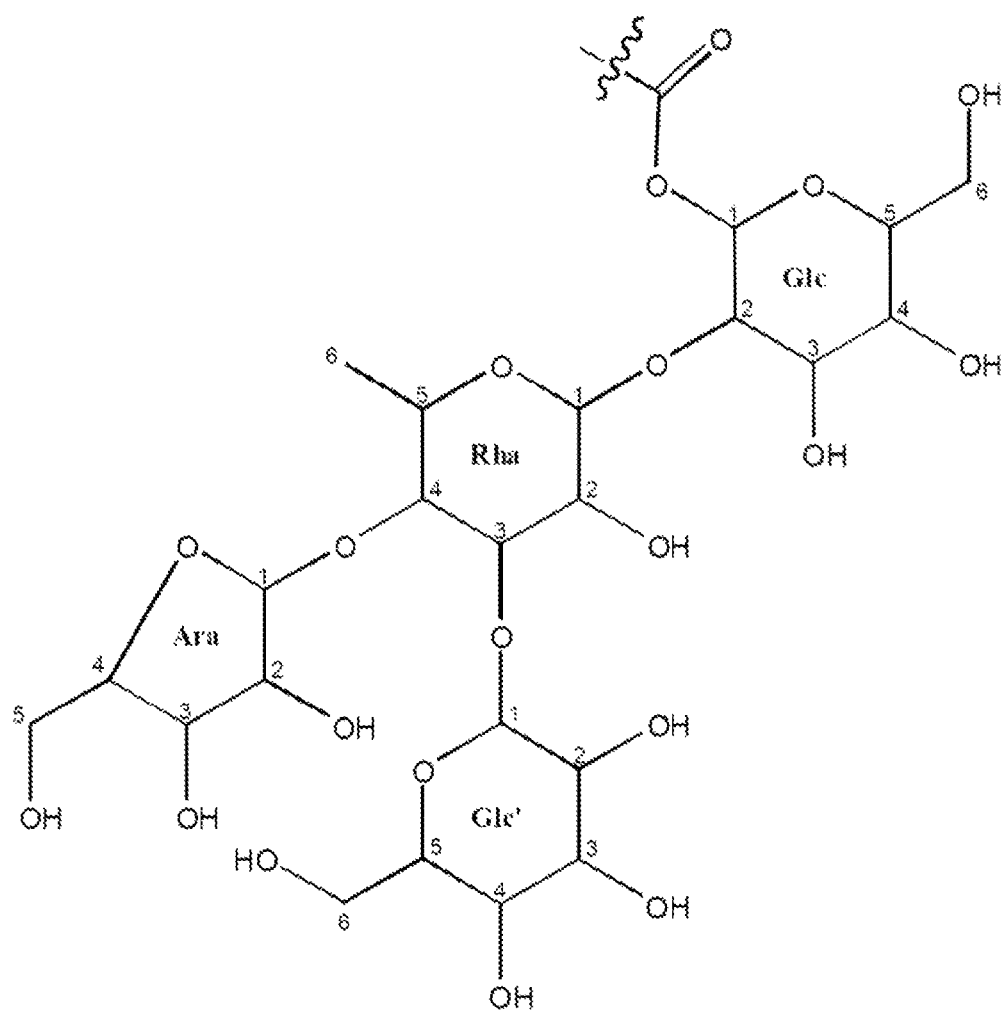
FIG. 31 shows the molecular formula of the C-28 glycoside region of Avicin D.
Figure 33:
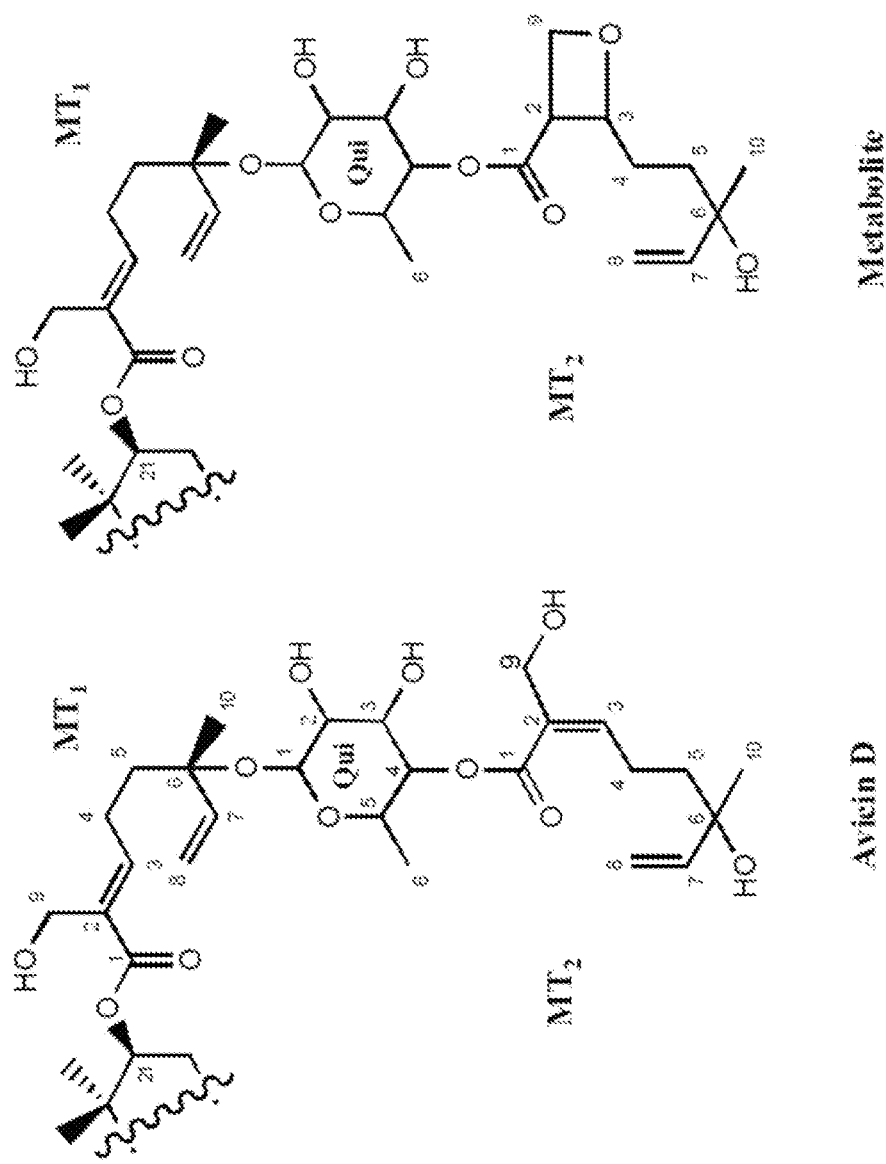
FIG. 33 shows the molecular formula of the C-21 monoterpene-glycoside region of Avicin D.

A preliminary comparison of the NMR data for Avicin D and the metabolite suggested that a change had occurred in one of the monoterpene moieties in the C-21 fragment of Avicin D. This was especially apparent in the downfield region of the 1H spectra which showed a reduction in complexity for the metabolite (compare FIGS. 7B and 14B). A complete assignment was undertaken for both the Avicin D and metabolite samples to determine the nature of the change in the monoterpene moiety and also to determine if another change had occurred elsewhere in the molecule. Due to the complexity of these structures, the structural analysis was undertaken separately for four fragments: the aglycone region (shown in FIG. 27), the C-3 glycoside region (shown in FIG. 29), the C-28 glycoside region (shown in FIG. 31), and the monoterpene-glycoside region at C-21 (shown in FIG. 33).

Figure 28:
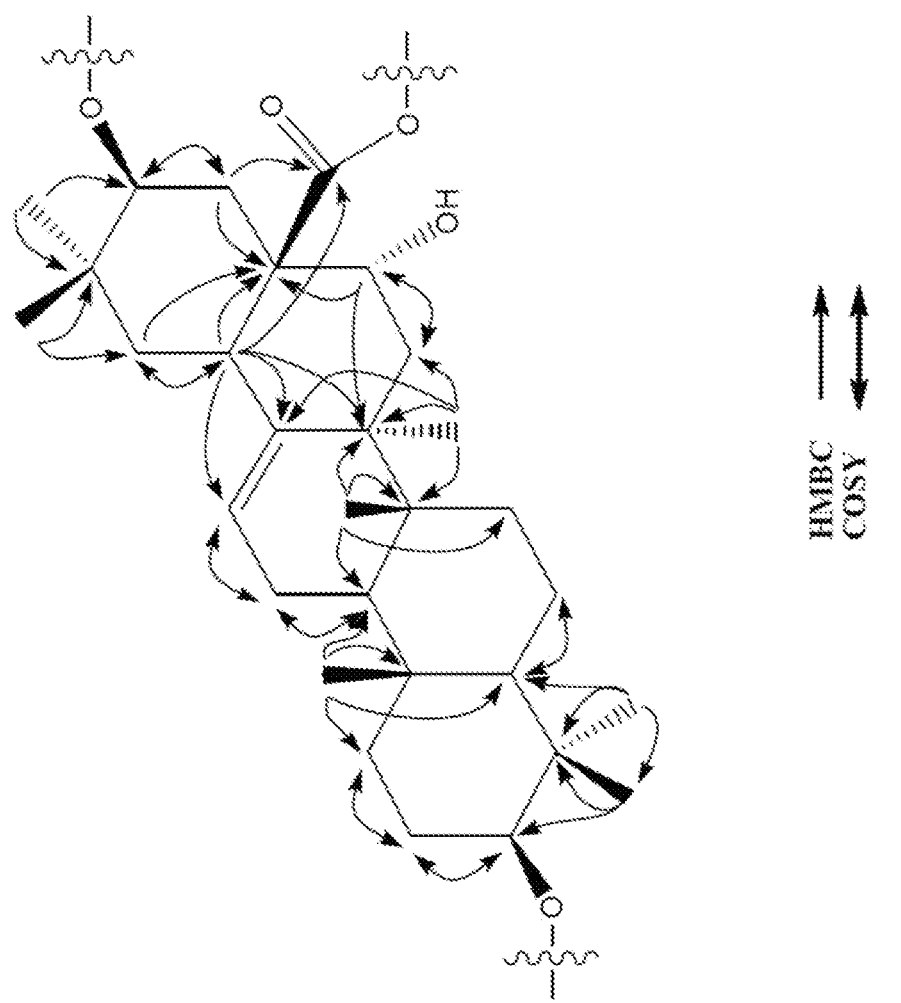
FIG. 28 shows the molecular formula of the aglycone region of Avicin D with the HMBC and COSY couplings overlaid.

The metabolite sample showed four carbonyl carbons in its $^{13}C$ spectra. One of the carbonyls was assigned to the GlcNAc residue of the C-3 glycoside region and two were assigned to the monoterpene glycoside fragment leaving the remaining carbonyl (175.3 ppm) to be assigned as C-28 which served as a starting point for the assignment of the aglycone fragment. The isolated multiplet at 2.97 ppm in the $^1H$ NMR spectrum showed an HMBC correlation to C-28 and the HSQC and Dept data indicated that is was part of a CH group with a carbon chemical shift of 41.6 ppm allowing it to be assigned as C-18. A second proton at 1.73 ppm ($CH_2$, $\delta_C$ 36.4) also showed an HMBC correlation to C-28 and so was assigned to C-22. COSY correlations between the H-22 protons (1.73 and 2.15 ppm) and the proton observed at 5.49 ppm in the $^1H$ NMR spectrum allowed assignment of H-21 (CH, $\delta_C$ 78.7 determined from the HSQC and Dept data). Likewise, COSY correlations between H-18 and protons at 1.19 and 2.52 ppm allowed assignment of the $CH_2$ group at C-19. An examination of the HMBC data indicated that the methyl singlets at 0.87 and 1.04 ppm showed HMBC correlations to C-19 and C-21 allowing assignment of the methyl groups at C-29 and C-30, respectively. Both methyl groups also showed HMBC correlations to a quaternary carbon at 35.9 ppm which was assigned as C-20. Assignment of C-17 ($\delta_C$ 52.3) was in turn made on the basis of HMBC correlations from H-18, H-19, and H-22. One additional proton at 4.47 ppm (CH, $\delta_C$ 74.3) showed an HMBC correlation to C-17 allowing it to be assigned to C-16. COSY correlations between H-16 and the protons at 1.53 and 1.62 ppm allowed assignment of C-15 ($CH_2$, 36.1 ppm). The C-12, C-13 unsaturation was assigned on the basis of HMBC correlations from H-18 to an olefinic quaternary carbon ($\delta_C$ 143.7) and olefinic methine ($\delta_H$ 5.35, $\delta_C$ 124.0) which were assigned as C-13 and C-12, respectively. The olefinic methine proton at 5.35 ppm showed a COSY correlation to the multiplet at 1.92 ppm (H-11, $CH_2$, $\delta_C$ 24.5) which in turn showed a COSY correlation to the multiplet at 1.68 ppm (H-9, CH, $\delta_C$ 48.1). The methyl singlet at 1.43 ppm showed HMBC correlations to C-13 and C-15 allowing it to be assigned to C-27 ($\delta_C$ 27.4). This methyl group also showed HMBC correlations to the quaternary carbons at 40.8 and 42.6 ppm. Both H-16 and H-18 showed HMBC correlations to the carbon at 42.6 ppm allowing it to be assigned as C-14 which in turn allowed the carbon at 40.8 ppm to be assigned as C-8. One of the overlapped methyl singlets at 0.77 ppm showed HMBC correlations to C-8, C-9, and C-14 as well as a methylene carbon at 34.6 ppm. The methyl group was assigned to C-26 and the methylene was assigned as C-7. The methyl singlet at 0.95 ppm ($\delta_C$ 16.2) showed an HMBC correlation to C-9 allowing it to be assigned to C-25. This methyl group also showed HMBC correlations to a quaternary carbon ($\delta_C$ 37.9), methine ($\delta_H$ 0.80, $\delta_C$ 57.1), and methylene group ($\delta_H$ 1.09/1.62, $\delta_C$ 39.9) which were assigned as C-10, C-5, and C-1, respectively. The $CH_2$ group at C-6 was assigned on the basis of COSY correlations between H-5 and the H-6 protons (1.38 and 1.62 ppm). The H-1 protons showed COSY correlations to the H-2 protons (1.66 and 1.88 ppm) which in turn showed COSY correlations to H-3 with C-2 ($\delta_C$ 27.1) and C-3 ($\delta_C$ 89.8) then assigned from the HSQC data. The second of the overlapped methyl singlets at 0.77 ppm and the singlet at 0.98 ppm showed HMBC correlations to C-3 and C-5 as well as a carbon at 40.1 ppm which was assigned as C-4. The methyl singlet at 0.98 ppm showed an HMBC correlation to the carbon at 17.1 ppm which was assigned as C-24 allowing the carbon at 17.7 ppm to be assigned as C-26. A summary of the $^1H$ and $^{13}C$ chemical shifts for Compound 8 are provided in Table 1 and the key HMBC and COSY correlations used to assign the aglycone region are presented in the diagram found in FIG. 28.

The aglycone region of the Avicin D standard was assigned in the same manner as described above for the metabolite. The $^1H$ and $^{13}C$ chemical shift assignments determined for Avicin D are summarized in Table 1 along with literature data for Avicin D (Jayatilake et al. 2003) and Gummiferoside A (Cao et al. 2007). Literature data for Gummiferoside A were included because they included the most detailed assignment of the $^1H$ chemical shifts for the aglycone region of a related compound available in the literature. The assignment of the aglycone region for Compound 8 and the Avicin D standard were nearly identical indicating that no change had occurred in the aglycone region of the metabolite. In addition, the data for both samples were very similar to those reported in the literature for the aglycone region of both Avicin D and Gummiferoside A. The only deviation was the $^{13}C$ chemical shift of C-28 reported in the literature for Avicin D. The reported value was slightly different from that observed at AMRI-BRC for either Avicin D or the metabolite, and also different from that reported for Gummiferoside A. The $^{13}C$ chemical shift of C-28 for Avicin G reported in the same paper was 175.3 ppm suggesting that the value reported for Avicin D was a typographical error. The remaining differences are all within the expected margin of experimental error.

TABLE 1

$^1H$ and $^{13}C$ Chemical Shift Assignments for the Aglycone Region of Avicin D and Metabolite, Compound 8 Samples.

| Position | Compound 8 | | Avicin D (AMRI-BRC) | | Avicin D (Jayatilake et al.)[a] | | Gummiferaoside A (Cao et al.)[b] | |
|---|---|---|---|---|---|---|---|---|
| | $^{13}C$ | $^1H$ | $^{13}C$ | $^1H$ | $^{13}C$ | $^1H$ | $^{13}C$ | $^1H$ |
| 1 | 39.9 | 1.09 m | 39.9 | 1.07 m | 39.9 | | 39.9 | 1.62 m |
| | | 1.62 m | | 1.62 m | | | | |
| 2 | 27.1 | 1.66 m | 27.1 | 1.66 m | 27.2 | | 27.4 | 1.70 m |
| | | 1.88 m | | 1.88 m | | | | 1.85 m |
| 3 | 89.8 | 3.27 m | 89.8 | 3.25 m | 89.9 | 3.25 m | 90.3 | 3.33 m |
| 4 | 40.1 | — | 40.1 | — | 40.1 | | 40.6 | — |
| 5 | 57.1 | 0.80 m | 57.0 | 0.80 m | 57.1 | | 57.1 | 0.78 m |

TABLE 1-continued

¹H and ¹³C Chemical Shift Assignments for the Aglycone Region of Avicin D and Metabolite, Compound 8 Samples.

| | Compound 8 | | Avicin D (AMRI-BRC) | | Avicin D (Jayatilake et al.)[a] | | Gummiferaoside A (Cao et al.)[b] | |
|---|---|---|---|---|---|---|---|---|
| Position | ¹³C | ¹H | ¹³C | ¹H | ¹³C | ¹H | ¹³C | ¹H |
| 6 | 19.6 | 1.38 m | 19.5 | 1.40 m | 19.5 | | 18.3 | 1.28 m |
| | | 1.62 m | | 1.62 m | | | | 1.50 m |
| 7 | 34.6 | 1.41 m | 34.6 | 1.42 m | 34.6 | | 34.3 | 1.36 m |
| | | 1.59 m | | 1.59 m | | | | |
| 8 | 40.8 | — | 40.8 | — | 40.8 | | 40.8 | — |
| 9 | 48.1 | 1.68 m | 48.1 | 1.69 m | 48.1 | | 48.0 | 1.68 m |
| 10 | 37.9 | — | 37.9 | — | 37.9 | | 37.9 | — |
| 11 | 24.5 | 1.92 m | 24.5 | 1.92 m | 24.5 | | 24.6 | 1.92 m |
| 12 | 124.0 | 5.35 m | 124.0 | 5.35 m | 124.0 | 5.34 | 124.0 | 5.34 m |
| 13 | 143.7 | — | 143.6 | — | 143.7 | | 143.7 | — |
| 14 | 42.6 | — | 42.6 | — | 42.6 | | 42.6 | — |
| 15 | 36.1 | 1.53 m | 36.1 | 1.52 t (13.3) | 36.2 | | 35.9 | 1.50 m |
| | | 1.62 m | | 1.60 m | | | | |
| 16 | 74.3 | 4.47 m | 74.2 | 4.49 m | 74.3 | 4.48 m | 74.1 | 4.45 dd (5.0, 5.0) |
| 17 | 52.3 | — | 52.3 | — | 52.3 | | 52.3 | — |
| 18 | 41.6 | 2.97 dd (4.4, 14.4) | 41.6 | 2.97 dd (4.4, 13.7) | 41.6 | | 41.5 | 2.96 dd (5.5, 10.5) |
| 19 | 48.7 | 1.19 m | 48.7 | 1.18 dd (4.4, 13.3) | 48.7 | | 48.0 | 1.18 dd (5.5, 12.0) |
| | | 2.52 t (13.7) | | 2.52 t (13.7) | | | | 2.50 dd (10.5, 12.0) |
| 20 | 35.9 | — | 35.9 | — | 35.9 | | 36.3 | — |
| 21 | 78.7 | 5.49 dd (5.6, 11.1) | 78.6 | 5.49 dd (5.6, 11.1) | 78.6 | 5.48 dd (5.5, 11.0) | 78.6 | 5.43 dd (5.5, 10.8) |
| 22 | 36.4 | 1.73 m | 36.4 | 1.72 m | 36.1 | | 36.1 | 1.67 m |
| | | 2.15 dd (5.6, 13.3) | | 2.15 dd (5.6, 13.7) | | | | 2.07 dd (5.5, 12.0) |
| 23 | 28.6 | 0.98 s | 28.6 | 0.98 s | 28.6 | 0.98 s | 28.4 | 1.09 s |
| 24 | 17.1 | 0.77 s | 17.1 | 0.77 s | 17.1 | 0.76 s | 16.9 | 0.86 s |
| 25 | 16.2 | 0.95 s | 16.2 | 0.95 s | 16.2 | 0.95 s | 16.2 | 0.96 s |
| 26 | 17.7 | 0.77 s | 17.7 | 0.77 s | 17.7 | 0.76 s | 17.6 | 0.75 s |
| 27 | 27.4 | 1.43 s | 27.4 | 1.43 s | 27.4 | 1.43 s | 27.4 | 1.42 s |
| 28 | 175.3 | — | 175.3 | — | 173.6 | | 175.4 | — |
| 29 | 29.4 | 0.87 s | 29.4 | 0.87 s | 29.4 | 0.86 s | 29.4 | 0.85 s |
| 30 | 19.4 | 1.04 s | 19.4 | 1.04 s | 19.4 | 1.04 s | 19.4 | 1.03 s |

Figure 30:
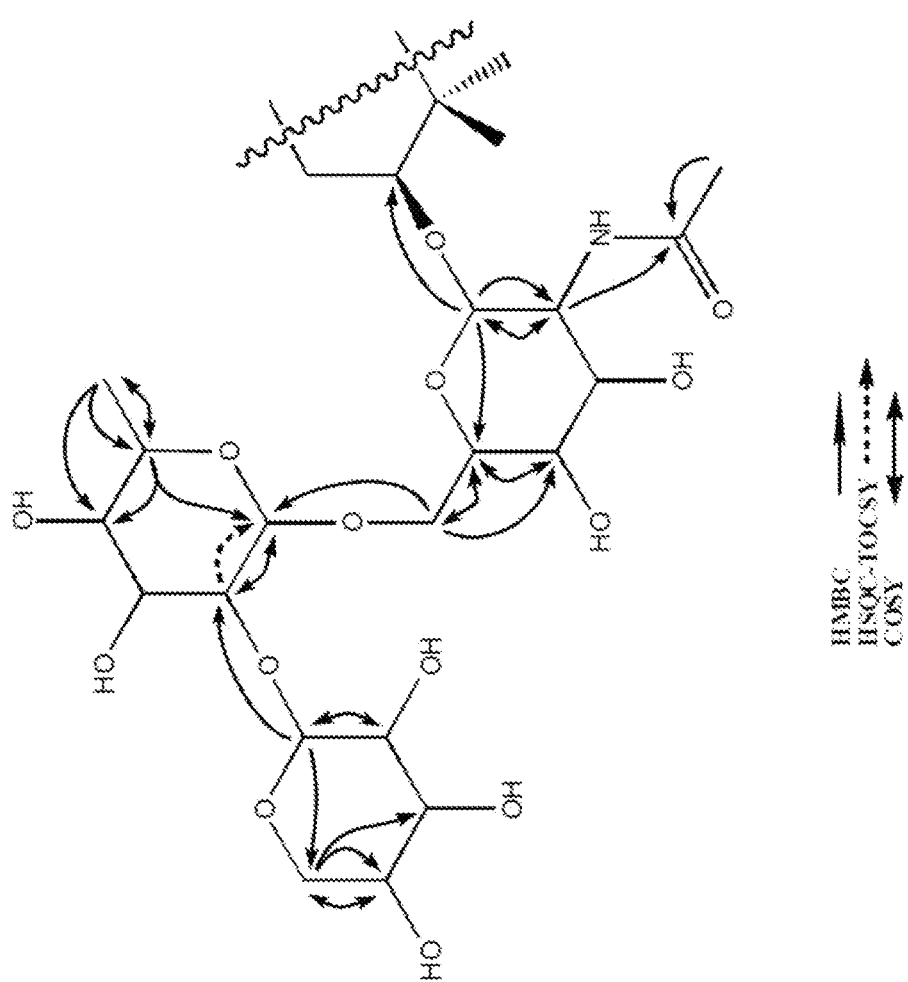
FIG. 30 shows the molecular formula of the C-3 glycoside region of Avicin D with the HMBC, HSQC-TOCSY, and COSY couplings overlaid.

An analysis of the HSQC data for the metabolite indicated the presence of 8 anomeric positions ($\delta_C$ 95.3-111.1, $\delta_H$ 4.40-5.35), the same number found in Avicin D, suggesting that 8 sugar residues were retained in the metabolite. The anomeric proton at 4.44 ppm ($\delta_C$ 104.8) showed an HMBC correlation to C-3 (89.8 ppm) of the aglycone indicating that it was the anomeric proton of the sugar residue present at C-3. This proton also showed an HMBC correlation to the carbon at 57.9 ppm (CH, $\delta_H$ 3.64) and a COSY correlation to a proton at 3.64 ppm allowing assignment of position 2 of this sugar residue. Both H-2 and the methyl singlet at 1.94 ppm showed HMBC correlations to the carbonyl at 173.4 ppm indicating the presence of an acetamide at position 2 and indicating that the GlcNAc residue present at C-3 in Avicin D is also present at this position in the metabolite. An HMBC correlation from H-1 to the carbon at 77.1 ppm (CH, $\delta_H$ 3.46) allowed assignment of C-5. COSY correlations from H-5 to protons at 4.07 and 3.32 allowed assignment of one of the H-6 protons and H-4, respectively. The other H-6 proton (3.77 ppm) was assigned from the COSY data. The H-6 protons showed an HMBC correlation to a carbon at 72.2 ppm (CH, $\delta_H$ 3.32) allowing assignment of C-4 and an HSQC correlation to the carbon at 69.9 ppm allowing assignment of C-6. Analysis of COSY and HSQC-TOCSY data provided tentative ¹H and ¹³C chemical shift assignments at C-3. A summary of the key COSY and HMBC correlations used to assign the GlcNAc residue of the metabolite are summarized in the diagram shown in FIG. 30.

The ¹H and ¹³C chemical shifts for the GlcNAc residue present at C-3 in Avicin D were assigned in a similar fashion and are summarized in Table 2 along with those of the metabolite. The chemical shift data for Avicin D and the metabolite are identical confirming that both have a GlcNAc residue attached at C-3 of the aglycone. Table 2 also provides the literature assignments for the sugar residues present at C-3 of the aglycone for Avicin D (Jayatilake et al. 2003) and Elliptioside A (Beutler et al. 1997). Elliptioside A was used to provide comparison data rather than Elliptioside E, which is a closer analog, because the data reported for Elliptioside A were more complete and Elliptiosides A and E have an identical glycoside structure at C-3. The ¹H and ¹³C chemical shifts for the GlcNAc residue of both the metabolite and Avicin D samples analyzed at AMRI-BRC are very similar to those reported for Avicin D and Elliptioside A.

TABLE 2

¹H and ¹³C Chemical Shift Assignments for the C-3 Glycoside Region of Avicin D and Metabolite, Compound 8 Samples.

| | Compound 8 | | Avicin D (AMRI-BRC) | | Avicin D (Jayatilake et al.) | | Elliptioside A (Beutler et al.) | |
|---|---|---|---|---|---|---|---|---|
| Position | ¹³C | ¹H | ¹³C | ¹H | ¹³C | ¹H | ¹³C | ¹H |
| GlcNAc-1 | 104.8 | 4.44 d (8.5) | 104.8 | 4.44 d (8.2) | 104.8 | 4.43d (8.7) | 104.6 | 4.47 d (7.8) |
| GlcNAc-2 | 57.9 | 3.64 m | 57.9 | 3.64 m | 57.9 | | 57.5 | |
| GlcNAc-3 | 75.7 | 3.44 m | 75.7 | 3.43 m | 76.4 | | 76.7 | 3.47 m |
| GlcNAc-4 | 72.2 | 3.32 m | 72.2 | 3.29 m | 71.1 | | 70.9 | 3.47 m |

TABLE 2-continued $^1$H and $^{13}$C Chemical Shift Assignments for the C-3 Glycoside Region of Avicin D and Metabolite, Compound 8 Samples.

| Position | Compound 8 | | Avicin D (AMRI-BRC) | | Avicin D (Jayatilake et al.) | | Elliptioside A (Beutler et al.) | |
|---|---|---|---|---|---|---|---|---|
| | $^{13}$C | $^1$H | $^{13}$C | $^1$H | $^{13}$C | $^1$H | $^{13}$C | $^1$H |
| GlcNAc-5 | 77.1 | 3.46 m | 77.1 | 3.45 m | 77.7 | | 76.6 | 3.55 m |
| GlcNAc-6 | 69.9 | 3.77 m | 69.9 | 3.76 m | 69.9 | | 69.6 | |
| | | 4.07 dd (1.5, 11.5) | | 4.07 dd (1.5, 11.5) | | | | |
| GlcNAc—C=O | 173.4 | — | 173.4 | — | 173.3 | — | 174.0 | — |
| GlcNAc—Me | 23.2 | 1.94 s | 23.2 | 1.94 s | 23.2 | 1.94 s | 23.2 | 1.97 s |
| Fuc-1 | 103.8 | 4.51 m | 103.8 | 4.51 m | 103.8 | 4.48 m | 103.5 | 4.51 d (8.2) |
| Fuc-2 | 82.3 | 3.62 m | 82.3 | 3.62 m | 82.3 | | 82.0 | 3.66 m |
| Fuc-3 | 75.0 | 3.63 m | 75.0 | 3.62 m | 74.9 | | 72.5 | 3.66 m |
| Fuc-4 | 72.6 | 3.66 m | 72.6 | 3.66 m | 72.7 | | 74.8 | 3.68 d |
| Fuc-5 | 71.7 | 3.59 q (6.7) | 71.7 | 3.59 q (6.7) | 71.7 | | 71.6 | 3.41 d (9.2) |
| Fuc-6 | 16.7 | 1.26 d (6.3) | 16.8 | 1.27 d (6.3) | 16.7 | 1.26 d (6.8) | 27.6 | 1.26 d (6.8) |
| Xyl-1 | 106.9 | 4.47 d (7.4) | 106.9 | 4.47 d (7.8) | 106.9 | 4.49 d (7.7) | 106.5 | 4.53 d (7.8) |
| Xyl-2 | 76.0 | 3.30 m | 76.0 | 3.30 m | 75.5 | | 75.9 | 3.40 t (8.9) |
| Xyl-3 | 77.5 | 3.36 m | 77.5 | 3.33 m | 77.1 | | 70.8 | 3.54 m |
| Xyl-4 | 71.1 | 3.50 m | 71.1 | 3.49 m | 71.1 | | 77.5 | 3.28 m |
| Xyl-5 | 67.3 | 3.26 m | 67.3 | 3.25 m | 67.3 | | 67.0 | 3.98 dd (5.3, 11.7) |
| | | 3.97 dd (5.6, 11.5) | | 3.97 dd (5.6, 11.5) | | | | |

The GlcNAc H-6 protons of the metabolite showed an HMBC correlation to the anomeric proton at 4.51 ppm ($\delta_C$ 103.8) confirming the presence of a sugar residue at this position in the metabolite. The H-5 proton of this sugar residue was assigned on the basis of an HMBC correlation to the anomeric carbon as well as the observation of COSY and HMBC correlations to a methyl group ($\delta_H$ 1.26, $\delta$C 16.7) at C-6 suggesting that the fucose residue present at this position in Avicin D was retained in the metabolite. HMBC correlations from H-5 and H-6 allowed assignment of C-4 (72.6 ppm) with H-4 (3.66 ppm) assigned from the HSQC data. The proton at 3.62 ppm (H-2) showed correlations in the HSQC-TOCSY spectrum to C-1 and a carbon at 82.3 ppm (CH, $\delta_H$ 3.62) which was assigned as C-2. A tentative assignment of the 3-position of this residue was made from a careful inspection of the COSY and HSQC-TOCSY data.

Assignment of the fucose residue for the Avicin D sample was similar to that made for the metabolite and the resulting $^1$H and $^{13}$C chemical shifts are provided in Table 2 along with the literature data for Avicin D and Elliptioside A. The chemical shifts observed for the metabolite are very similar to those observed for the Avicin D sample analyzed at AMRI-BRC and also reported for Avicin D in the literature and confirm that a fucose residue is present at C-6 of the GlcNAc residue in the metabolite. The data reported for Elliptioside A are in general agreement, although a couple of the assignments of fucose residue in Elliptioside A appear to be incorrect. The $^{13}$C chemical shifts of Fuc-3 and Fuc-4 as reported for Elliptioside A appear to be reversed. Also, the $^{13}$C chemical shift of the Fuc-6 methyl group appears to be switched with that of MT2-10 which will be discussed more later.

An HMBC correlation from the anomeric proton at 4.47 ppm ($\delta_C$ 106.9) to C-2 of the fucose residue confirmed the presence of a sugar residue at Fuc-2 in the metabolite. A COSY correlation from the anomeric proton to a proton at 3.30 ppm allowed assignment of H-2 (CH, $\delta_C$ 76.0 ppm). The anomeric proton at 4.47 ppm also showed an HMBC correlation to the methylene group at 67.3 ppm which was observed to have proton chemical shifts of 3.26 and 3.97 ppm in the HSQC spectrum and were assigned as the methylene group at position 5 of this sugar residue. The H-5 protons showed HMBC correlations to carbons at 71.1 and 77.5 ppm which were found to have attached protons at 3.50 and 3.36 ppm, respectively, by examination of the HSQC data. The carbon at 71.1 ppm was assigned as C-4 on the basis of COSY correlations between the H-5 protons and H-4 (3.50 ppm) leaving the carbon at 77.5 ppm to be assigned as C-3.

A similar assignment of this residue was made for the Avicin D sample and the resulting $^1$H and $^{13}$C chemical shifts for both the Avicin D and metabolite samples are provided in Table 2 along with the literature data for Avicin D and Elliptioside A. The chemical shifts observed for the metabolite are very similar to those observed for the Avicin D sample analyzed at AMRI-BRC. The data are also very similar to those reported in the literature for the xylose residue present in both Avicin D and Elliptioside A and confirm the presence of a xylose at the Fuc-2 position in the metabolite. The $^{13}$C chemical shifts of Xyl-3 and Xyl-4 reported for Elliptioside A once again appear to be reversed.

A complete assignment of the C-3 glycoside region of the Avicin D and metabolite samples, together with a comparison of the data reported in the literature for this region has indicated that the C-3 glycoside fragment is unchanged in the metabolite.

Assignment of four of the remaining five unassigned sugar residues to the C-28 region of the aglycone, including their connectivities was straightforward; however, an unambiguous assignment of all $^1$H and $^{13}$C chemical shifts for this region was made difficult by the degree of overlap present in the data. The anomeric proton at 5.32 ppm ($\delta_C$ 95.3) showed an HMBC correlation to C-28 (175.3 ppm) of the aglycone fragment of the metabolite indicating that it was the anomeric proton of the sugar residue present at C-28 of the aglycone fragment. This proton also showed a COSY correlation to a proton at 3.52 ppm allowing assignment of H-2 for this sugar residue. H-2 in turn showed HMBC correlations to anomeric carbons at 95.3 and 101.3 ppm indicating that a second sugar residue was present at C-2 of the sugar residue present at C-28 of the aglycone. The $^{13}$C chemical shift for C-2 ($\delta_C$ 76.4) was determined by a combination of an HSQC correlation with H-2 and the observation of an HMBC correlation from the anomeric proton of the rhamnose residue ($\delta_H$ 5.33, assigned below) to C-2. H-2 also showed an HSQC-TOCSY correlation with C-4 (71.2 ppm). One of the oxymethylene groups ($\delta_H$ 3.66, 3.78, $\delta_C$ 62.2) showed COSY correlations to a proton at 3.31 ppm and HSQC-TOCSY correlations to a carbon at 78.6 ppm (CH, $\delta_H$ 3.31) allowing assignment of positions 5 and 6. The H-6 protons also showed an HMBC correlation to C-4. The HSQC spectrum indicated a $^1$H chemical shift of 3.37 ppm for H-4 which was confirmed by observation of a correlation from H-4 to C-6 in the HSQC-TOCSY data. The $^1$H and $^{13}$C chemical shifts for position three of this residue were assigned on the basis of the remaining carbons after assignment of the other sugar residues (as was position 3 of the second glucose residue assigned below).

The $^1$H and $^{13}$C chemical shifts for the Glc residue present at C-28 of the aglycone in Avicin D were assigned in a similar fashion and are summarized in Table 3 along with those of the metabolite. The chemical shift data for Avicin D and the metabolite are very similar confirming that both have a Glc residue attached at C-28 of the aglycone. Table 3 also provides the literature assignments for the glucose residue present at C-28 for Avicin D (Jayatilake et al. 2003) and Elliptioside A (Beutler et al. 1997). As above, Elliptioside A was used to provide comparison data rather than Elliptioside E because the data reported for Elliptioside A were more complete and the glycoside present at C-28 of the aglycone is the same for both. The $^1$H and $^{13}$C chemical shifts assigned for the Glc residue of both the metabolite and Avicin D samples analyzed at AMRI-BRC were similar to those reported for Avicin D and Elliptioside A although a few minor differences in assignment are notable. There was a slight difference in the reported and observed $^{13}$C chemical shifts of C-2 and C-4. Also, the assignments of C-3 and C-4 reported for Elliptioside A appear to be reversed.

correlation to the carbon at 71.5 ppm allowing assignment of H-2 and C-2 of this sugar residue. The anomeric proton also showed an HMBC correlation to a carbon at 82.6 ppm which was assigned as C-3. The $^1$H chemical shift of H-3 ($\delta_H$ 3.88) was determined from the HSQC data as well as a COSY correlation with H-2. A COSY correlation from H-3 to the proton at 3.66 ppm allowed assignment of H-4. HMBC and HSQC-TOCSY correlations from H-2 to a carbon at 78.6 ppm allowed assignment of C-4. The methyl doublet at 1.32 ppm showed a COSY correlation to a proton at 3.86 ppm allowing assignment of H-5 and H-6. The methyl protons also showed HMBC correlations to C-4 and a carbon at 69.1 which was assigned as C-5. Finally, C-6 ($\delta_C$ 18.6) was assigned from the HSQC data.

An analogous assignment was made for this residue in the Avicin D sample and is reported in Table 3 along with the literature assignment for Avicin D and Elliptioside A. The chemical shifts observed for the metabolite are very similar to those observed for the Avicin D sample analyzed at AMRI-BRC. The data are also very similar to those reported in the literature for the residue at this position in both Avicin D and Elliptioside A and confirm the presence of a rhamnose at the Glc-2 position in the metabolite. There are minor differences in the $^{13}$C chemical shift assignments which are within the expected experimental error. The observed and reported chemical shifts of the anomeric proton are very similar but the

TABLE 3

$^1$H and $^{13}$C Chemical Shift Assignments for the C-28 Glycoside Region of Avicin D and Metabolite, Compound 8 Samples.

| Position | Compound 8 $^{13}$C | Compound 8 $^1$H | Avicin D (AMRI-BRC) $^{13}$C | Avicin D (AMRI-BRC) $^1$H | Avicin D (Jayatilake et al.) $^{13}$C | Avicin D (Jayatilake et al.) $^1$H | Elliptioside A (Beutler et al.) $^{13}$C | Elliptioside A (Beutler et al.) $^1$H |
|---|---|---|---|---|---|---|---|---|
| Glc-1 | 95.3 | 5.32 m | 95.3 | 5.32 m | 95.3 | 5.33 d (7.7) | 95.2 | 5.33 d (7.8) |
| Glc-2 | 76.4 | 3.52 m | 76.4 | 3.52 m | 81.0 | | 82.1 | 3.90 dd (3.9, 6.7) |
| Glc-3 | 78.0 | 3.37 m | 78.1 | 3.36 m | 78.6 | | 71.4 | 4.23 d (5.4) |
| Glc-4 | 71.2 | 3.37 m | 71.1 | 3.36 m | 71.5 | | 78.3 | 3.55 m |
| Glc-5 | 78.6 | 3.31 m | 78.6 | 3.30 m | 75.6 | | 75.3 | |
| Glc-6 | 62.2 | 3.66 m 3.78 m | 62.2 | 3.64 m 3.79 dd (2.2, 10.4) | 62.3 | | 62.0 | 3.82 m |
| Rha-1 | 101.3 | 5.33 m | 101.3 | 5.32 m | 101.3 | 5.33 d (7.7) | 101.3 | 5.33 d (7.8) |
| Rha-2 | 71.5 | 4.21 dd (1.9, 3.0) | 71.5 | 4.21 dd (1.9, 3.0) | 71.2 | | 70.9 | 3.55 m |
| Rha-3 | 82.6 | 3.88 m | 82.6 | 3.88 m | 82.6 | | 82.1 | |
| Rha-4 | 78.6 | 3.66 m | 78.6 | 3.66 m | 78.2 | | 78.2 | |
| Rha-5 | 69.1 | 3.86 m | 69.1 | 3.87 m | 69.1 | | 69.2 | 3.79 d (9.9) |
| Rha-6 | 18.6 | 1.32 d (6.3) | 18.6 | 1.33 d (6.3) | 18.6 | 1.32 d (6.4) | 18.6 | |
| Glc'-1 | 105.8 | 4.49 d (7.8) | 105.8 | 4.49 d (7.8) | 105.8 | 4.46 (d (7.3) | 105.5 | 4.52 d (7.4) |
| Glc'-2 | 75.3 | 3.29 m | 75.3 | 3.27 m | 75.5 | | 75.0 | 3.35 m |
| Glc'-3 | 79.1 | 3.52 m | 79.0 | 3.52 m | 77.6 | | 77.8 | |
| Glc'-4 | 71.1 | 3.37 m | 71.2 | 3.36 m | 72.2 | | 71.8 | |
| Glc'-5 | 77.7 | 3.29 m | 77.7 | 3.27 m | 77.5 | | 77.2 | |
| Glc'-6 | 62.3 | 3.74 m 3.84 m | 62.3 | 3.72 dd (4.4, 11.8) 3.82 dd (2.2, 11.8) | 62.2 | | 62.0 | 3.76 dd (2.8, 12.0) |
| Ara-1 | 111.0 | 5.35 m | 111.0 | 5.35 m | 111.0 | 5.34 d (2.1) | 110.5 | 5.35 d (2.1) |
| Ara-2 | 83.9 | 4.09 dd (1.9, 3.7) | 83.9 | 4.09 dd (1.9, 3.7) | 85.6 | | 85.1 | 4.04 m |
| Ara-3 | 78.6 | 3.88 m | 78.6 | 3.88 m | 79.1 | | 78.7 | 3.63 m |
| Ara-4 | 85.6 | 4.04 ddd (3.3, 5.2, 6.3) | 85.5 | 4.03 ddd (3.3, 5.2, 6.3) | 83.9 | | 83.7 | 4.09 dd (2.1, 3.6) |
| Ara-5 | 63.1 | 3.62 m 3.74 m | 63.1 | 3.62 m 3.75 m | 63.1 | | 62.6 | 3.63 m 3.73 dd (5.0, 12.0) |

Figure 32:
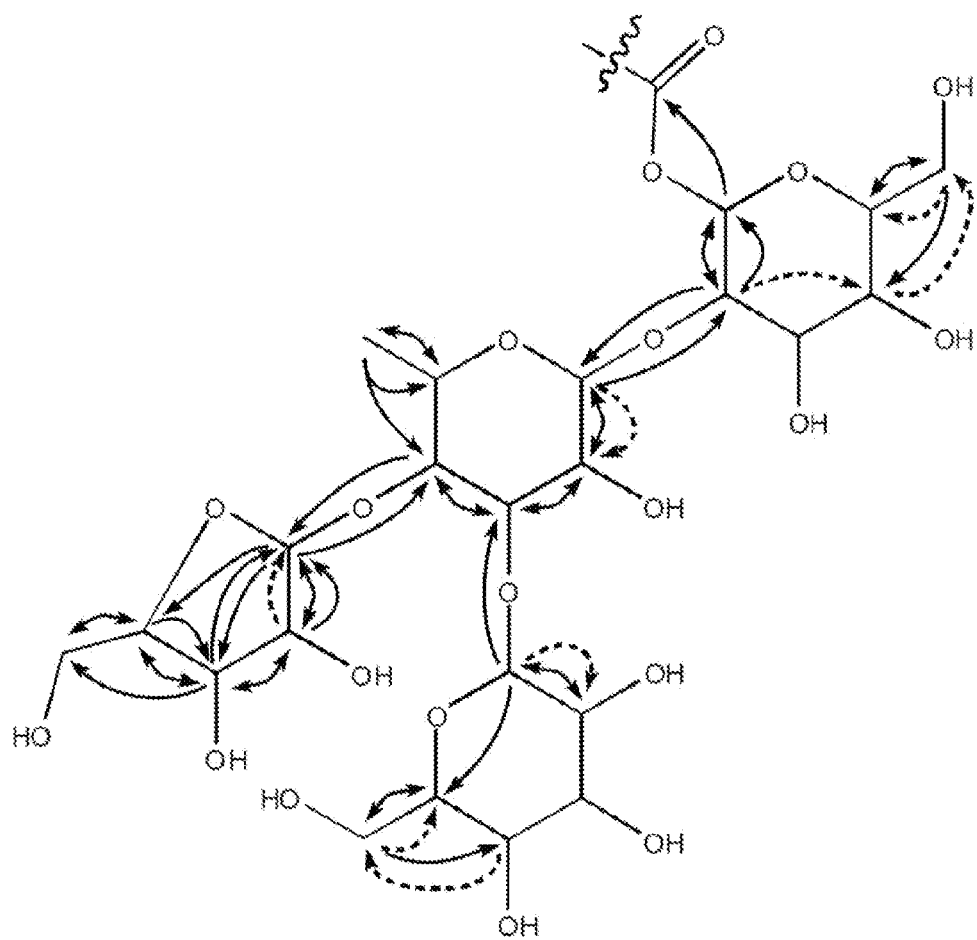
FIG. 32 shows the molecular formula of the C-28 glycoside region of Avicin D with the HMBC, HSQC-TOCSY, and COSY couplings overlaid.

A correlation diagram of the C-28 glycoside region is shown in FIG. 32. An HMBC correlation from the anomeric proton at 5.33 ppm ($\delta_C$ 101.3) to C-2 of the glucose residue indicated the presence of a sugar residue at Glc-2 which is also present in Avicin D. The reciprocal correlation from the Glc H-2 proton to the anomeric carbon at 101.3 ppm was also observed. The anomeric proton (5.33 ppm) showed a COSY correlation to the proton at 4.21 ppm and an HSQC-TOCSY $^1$H chemical shift assignments for H-2 and H-5 of the rhamnose residue reported for Elliptioside A appear to be erroneous.

The anomeric proton of a third sugar residue ($\delta_H$ 4.49, $\delta_C$ 105.8) showed an HMBC correlation with C-3 of the rhamnose residue indicating the presence of a sugar residue at this position as is observed for Avicin D. The anomeric proton showed a COSY correlation with proton at 3.29 ppm and an HSQC-TOCSY correlation with a carbon at 75.3 ppm allowing assignment of H-2 and C-2 for this residue, respectively. Positions 4-6 of this residue were assigned in the same manner as the Glc residue at C-28 of the aglycone. One of the oxymethylene groups ($\delta_H$ 3.74, 3.84, $\delta_C$ 62.3) showed COSY correlations to a proton at 3.29 ppm and HSQC-TOCSY correlations to a carbon at 77.7 ppm allowing assignment of positions 5 and 6. The H-6 protons also showed an HMBC correlation to C-4 (71.1 ppm). The HSQC spectrum indicated a $^1$H chemical shift of 3.37 ppm for H-4 which was confirmed by observation of a correlation from H-4 to C-6 in the HSQC-TOCSY data. The $^1$H and $^{13}$C chemical shifts for position three of this residue were assigned on the basis of the remaining carbons after assignment of the other sugar residues.

Assignment of the $^1$H and $^{13}$C chemical shifts for this residue in Avicin D were made in aparallel fashion and a comparison between the data for the metabolite and Avicin D standard confirmed the presence of a Glc residue at Rha-3 (Table 3). The literature assignments for this residue in Avicin D (Jayatilake et al. 2003) and Elliptioside A (Beutler et al. 1997) are very close to those determined at AMRI-BRC and the minor differences observed are within the expected level of experimental error.

The anomeric proton of a fourth sugar residue ($\delta_H$ 5.35, $\delta_C$ 111.0) showed an HMBC correlation with C-4 of the rhamnose indicating the presence of a sugar residue at this position in the metabolite. The anomeric proton showed a COSY correlation with a proton at 4.09 ppm and an HSQC-TOCSY correlation with a carbon at 83.9 ppm allowing assignment of H-2 and C-2 for this residue, respectively. An HMBC correlation was also observed between H-1 and C-1 within this residue. H-2 showed a COSY correlation to a proton at 3.88 ppm which in turn showed a COSY correlation to a proton at 4.04 that also showed a COSY correlation to protons at 3.62 and 3.74 ppm and allowed assignment of H-3 through H-5. Reciprocal HMBC correlations between H-3 and C-1 and H-1 and C-3 allowed assignment of C-3 ($\delta_C$ 78.6). H-3 also showed a correlation to a carbon at 63.1, which together with the HSQC data allowed assignment of C-5 (63.1 ppm). The $^{13}$C chemical shift of C-4 (85.6 ppm) was determined from the HSQC data. An HMBC correlation between H-1 and C-4 confirmed the assignment of C-4.

The $^1$H and $^{13}$C chemical shifts for this residue determined for Avicin D were identical to those of the metabolite and confirmed that this sugar residue is an arabinose in the metabolite (Table 3). The literature assignments for this residue in Avicin D (Jayatilake et al. 2003) and Elliptioside A (Beutler et al. 1997) are similar to those observed at AMRI-BRC although the assignments for positions 2 and 4 of the arabinose appear to be reversed in both cases. An HMBC correlation between H-1 and the carbon at 85.6 ppm could allow this carbon to be assigned as either C-2 or C-4; however, the remainder of the data clearly indicated that the carbon at 85.6 ppm must be assigned as C-4.

A complete assignment of the C-28 glycoside region of the Avicin D and metabolite samples, together with a comparison of the data reported in the literature for this region has indicated that the C-28 glycoside fragment is unchanged in the metabolite.

C-21 Monoterpene-Glycoside Region

An analysis of the monoterpene-glycoside region at C-21 of the aglycone fragment indicated that there is a clear structural difference between the Avicin D sample and the metabolite. A complete analysis, as described in detail below, indicated that the $MT_1$ and quinovose moieties were identical between the two samples with the difference located in the outer monoterpene, $MT_2$, shown in FIG. 33.

The H-21 proton (5.49 ppm) of the aglycone moiety of the metabolite showed an HMBC correlation to the carbonyl at 168.7 which was assigned as C-1 of the inner monoterpene, $MT_1$. The methylene protons at 4.32 ppm also showed an HMBC correlation to C-1 allowing them to be assigned as the H-9 protons ($CH_2$, $\delta_C$ 56.6). The olefinic proton at 6.90 ppm showed HMBC correlations to C-1 and also a carbon at 132.9 ppm allowing assignment of H-3 (6.90 ppm) and C-2 (132.9 ppm). A COSY correlation was also observed between H-3 and the methylene protons at 2.44 ppm which in turn showed a COSY correlation to the methylene protons at 1.75 ppm and allowed assignment of the H-4 and H-5 protons, respectively. The $^{13}$C chemical shifts for C-3 through C-5 were then determined from the HSQC data and the assignments were confirmed by observation of HMBC correlations from H-3 to C-4 and C-5. The H-5 protons, the methyl protons at 1.38 ppm, and the olefinic proton at 5.94 ppm all showed HMBC correlations to a quaternary carbon at 81.0 ppm which was assigned as C-6. The methyl protons (1.38 ppm) were assigned as H-10 and the olefinic proton (5.94 ppm) as H-7. This assignment was confirmed by the observation of HMBC correlations from the methyl singlet (1.38 ppm) to both C-5 and a carbon at 144.0 ppm which was assigned as C-7 in addition to the correlation with C-6 mentioned above. H-7 showed COSY correlations with protons at 5.21 and 5.29 ppm allowing assignment of the H-8 protons and C-8 ($\delta_C$ 116.0) was in turn assigned from the HSQC data.

The $^1$H and $^{13}$C chemical shifts for $MT_1$ in Avicin D were assigned in a similar fashion and are summarized in Table 4 along with those of the metabolite. The chemical shift data for Avicin D and the metabolite are identical confirming that both have the same monoterpene present at C-21 of the aglycone. Table 4 also provides the literature assignments for $MT_1$ for both Avicin D (Jayatilake et al. 2003) and Elliptioside E (Beutler et al. 1997). The $^1$H and $^{13}$C chemical shifts for the $MT_1$ fragment of both the metabolite and Avicin D samples analyzed at AMRI-BRC are very similar to those reported in the literature for Avicin D and Elliptioside E. The only significant deviation between the Avicin D data acquired at AMRI-BRC and those reported in the literature is that the $^{13}$C chemical shift assignments of C-1 and C-2 for $MT_1$ and $MT_2$ in Avicin D (and also Elliptioside E) reported in the literature appear to be reversed. Elliptioside E shows small differences in chemical shift (H-7, H-10, and C-5) that are attributed to differences in stereochemistry at C-6 (Jayatilake et al. 2003) for the Elliptiosides.

TABLE 4

$^1$H and $^{13}$C Chemical Shift Assignments for the C-21 Monoterpene-Glycoside Region of Avicin D and Metabolite, Compound 8 Samples.

| Position | Compound 8 $^{13}$C | Compound 8 $^1$H | Avicin D (AMRI-BRC) $^{13}$C | Avicin D (AMRI-BRC) $^1$H | Avicin D (Jayatilake et al.)[a] $^{13}$C | Avicin D (Jayatilake et al.)[a] $^1$H | Elliptioside E (Beutler et al.)[b,c] $^{13}$C | Elliptioside E (Beutler et al.)[b,c] $^1$H |
|---|---|---|---|---|---|---|---|---|
| MT$_1$-1 | 168.7 | — | 168.7 | — | 168.2 | | 169.0 | |
| MT$_1$-2 | 132.9 | — | 132.9 | — | 132.5 | | 132.5 | |
| MT$_1$-3 | 148.0 | 6.90 t (7.8) | 148.0 | 6.90 t (7.8) | 148.0 | 6.89 t (7.5) | 148.6 | 6.92 t (7.6) |
| MT$_1$-4 | 24.3 | 2.44 m | 24.3 | 2.44 m | 24.3 | | 24.1 | |
| MT$_1$-5 | 41.3 | 1.75 m | 41.3 | 1.75 m | 41.3 | | 39.5 | |
| MT$_1$-6 | 81.0 | — | 81.0 | — | 81.0 | | 81.2 | |
| MT$_1$-7 | 144.0 | 5.94 dd (10.7, 17.4) | 144.0 | 5.95 dd (10.7, 17.4) | 144.0 | 5.94 dd (10.7, 17.8) | 143.7 | 6.01 dd (11.4, 17.4) |
| MT$_1$-8 | 116.0 | 5.21 dd (1.1, 11.1) 5.29 dd (1.1, 17.8) | 116.0 | 5.22 dd (1.1, 9.6) 5.30 dd (1.1, 17.4) | 116.0 | 5.22 5.27 | 116.0 | |
| MT$_1$-9 | 56.6 | 4.32 s | 56.6 | 4.31 s | 56.6 | 4.32 s | 56.5 | |
| MT$_1$-10 | 23.8 | 1.38 s | 23.8 | 1.38 s | 23.8 | 1.38 s | 24.0 | 1.35 s |
| Qui-1 | 99.3 | 4.40 d (7.8) | 99.3 | 4.42 d (7.8) | 99.4 | 4.42 d (7.8) | 98.9 | 4.41 d (7.9) |
| Qui-2 | 75.4 | 3.25 m | 75.5 | 3.27 m | 76.0 | | 75.3 | |
| Qui-3 | 75.6 | 3.50 m | 75.6 | 3.54 t (9.6) | 75.3 | | 75.1 | |
| Qui-4 | 77.5 | 4.58 t (9.6) | 77.6 | 4.64 t (9.6) | 76.4 | 4.61 t (9.5) | 76.7 | 4.64 t (9.5) |
| Qui-5 | 70.7 | 3.47 m | 70.9 | 3.49 m | 70.9 | | 70.8 | |
| Qui-6 | 18.4 | 1.16 d (5.9) | 18.3 | 1.12 d (6.3) | 18.3 | 1.11 d (6.4) | 18.2 | 1.11 d (6.2) |
| MT$_2$-1 | 173.4 | — | 168.2 | — | 168.7 | | 168.5 | |
| MT$_2$-2 | 55.9 | 2.71 m | 132.5 | — | 132.9 | | 131.9 | |
| MT$_2$-3 | 78.1 | 4.17 m | 148.5 | 6.94 t (7.8) | 148.5 | 6.79 dt (1.5, 7.8) | 145.5 | 6.97 t (7.8) |
| MT$_2$-4 | 30.7 | 1.84 m 2.08 m | 24.5 | 2.37 m | 24.5 | | 24.5 | |
| MT$_2$-5 | 37.5 | 1.77 m 1.91 m | 41.9 | 1.64 m | 41.9 | | 41.7 | |
| MT$_2$-6 | 84.7 | — | 73.6 | — | 73.6 | | 73.9 | |
| MT$_2$-7 | 144.8 | 5.86 dd (10.7, 17.4) | 145.9 | 5.91 dd (10.7, 17.4) | 145.9 | 5.91 dd (10.7, 17.8) | 149.3 | 5.91 dd (10.8, 17.4) |
| MT$_2$-8 | 112.0 | 4.98 dd (1.9, 10.7) 5.16 dd (1.9, 17.4) | 112.5 | 5.05 dd (1.5, 10.7) 5.22 dd (1.5, 17.4) | 112.5 | 5.04 5.19 | 112.9 | 5.07 d (10.8) |
| MT$_2$-9 | 62.7 | 3.86 m 3.93 dd (4.8, 10.7) | 56.5 | 4.32 s | 56.5 | 4.31 s | 56.3 | |
| MT$_2$-10 | 27.5 | 1.27 s | 27.9 | 1.27 s | 27.9 | 1.27 s | 16.8 | 1.28 s |

Figure 34:
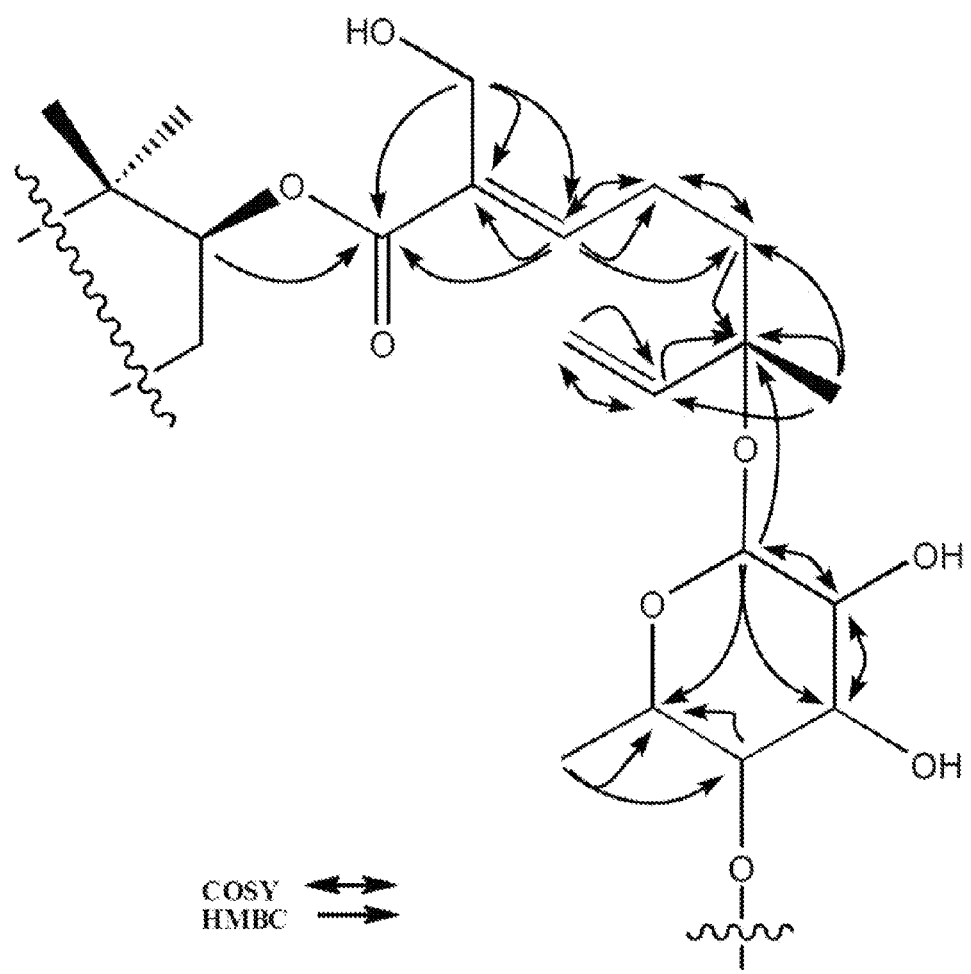
FIG. 34 shows the portion of the C-21 monoterpene-glycoside region closes to the aglycone core of Avicin D ($MT_1$) with the HMBC and COSY couplings overlaid.

A correlation diagram for MT$_1$ can be found in FIG. 34. An HMBC correlation from the remaining unassigned anomeric proton at 4.40 ppm ($\delta_C$ 99.3) of the metabolite to C-6 of MT$_1$ indicated the presence of a sugar residue at this position as is observed for Avicin D. A COSY correlation from the anomeric proton to a proton at 3.25 ppm allowed assignment of H-2 (CH, $\delta_C$ 75.4). H-2 in turn showed a COSY correlation to a proton at 3.50 ppm allowing assignment of H-3. The anomeric proton showed HMBC correlations to the carbons at 75.6 and 70.7 ppm. The methyl protons at 1.16 ppm also showed an HMBC correlation to the carbon at 70.7 ppm allowing it to be assigned as C-5 which in turn allowed the carbon at 75.6 ppm to be assigned as C-3. The methyl protons (1.16 ppm, H-6) showed a COSY correlation to the proton at 3.47 ppm allowing assignment of H-5 which was confirmed observation of an HSQC correlation with C-5. The isolated multiplet at 4.58 ppm showed HMBC correlations to C-5 and C-6 which indicated that it must be H-4 and was confirmed by observation of an HMBC correlation from the H-6 methyl protons.

Figure 35:
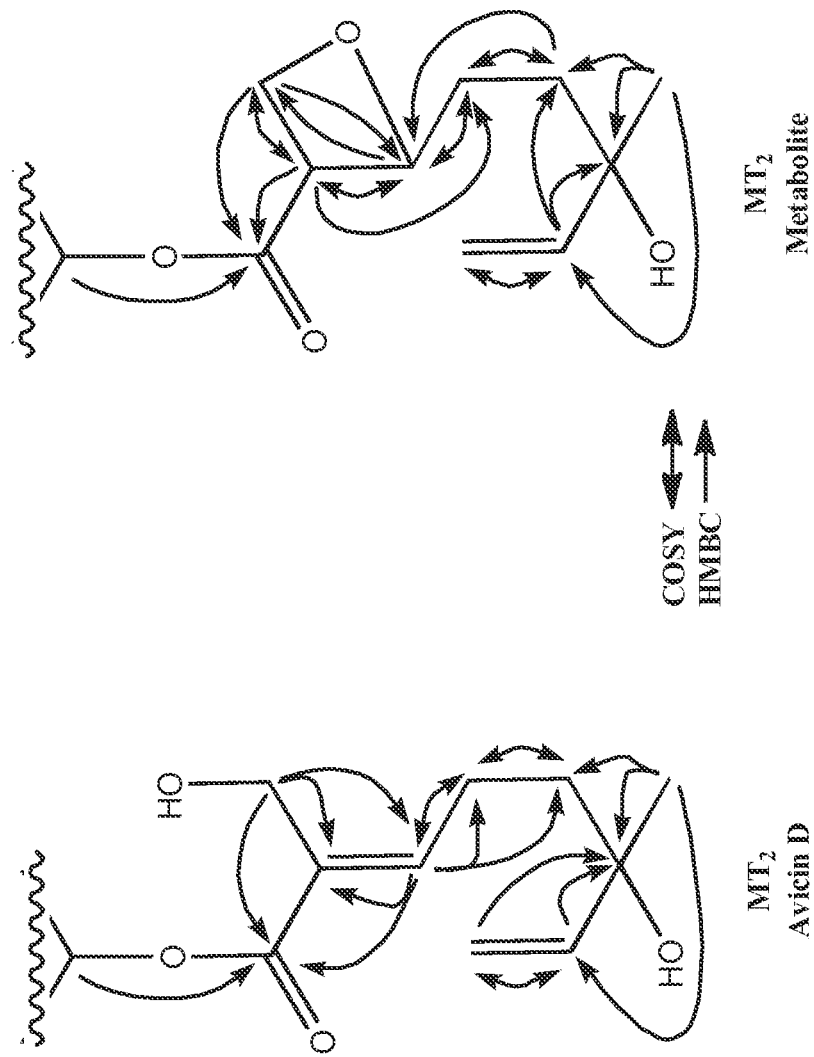
FIG. 35 shows the portion of the C-21 monoterpene-glycoside region furthest away from the aglycone core ($MT_2$) and containing the reactive portion of the molecule with the COSY and HMBC couplings overlaid.

Assignment of this residue for the Avicin D sample was similar to that for the metabolite and the resulting $^1$H and $^{13}$C chemical shifts are provided in Table 4 together with the data for this residue from the literature. The chemical shifts observed for the metabolite are very similar to those observed for the Avicin D sample analyzed at AMRI-BRC and also to those reported for Avicin D in the literature and confirm that a quinovose residue is present at C-6 of the MT$_1$ fragment in the metabolite. The only significant differences were observed in the $^1$H chemical shifts for H-4 and H-6 which were slightly different in the metabolite which are the result of structural changes in MT$_2$ (see FIG. 35).

Assignment of the MT$_2$ fragment for the Avicin D sample was similar to that carried out for MT$_1$ as described above. The H-4 proton (4.64 ppm) of the quinovose residue of Avicin D showed an HMBC correlation to the carbonyl at 168.2 which was assigned as C-1 of the outer monoterpene, MT$_2$. The methylene protons at 4.32 ppm also showed an HMBC correlation to C-1 allowing them to be assigned as the MT$_2$ H-9 protons (CH$_2$, $\delta_C$ 56.6). The olefinic proton at 6.94 ppm showed HMBC correlations to C-1 and also a carbon at 132.5 ppm allowing assignment of H-3 (6.94 ppm) and C-2 (132.5 ppm). A COSY correlation was also observed between H-3 and the methylene protons at 2.37 ppm which in turn showed a COSY correlation to the methylene protons at 1.64 ppm and allowed assignment of the H-4 and H-5 protons, respectively. The $^{13}$C chemical shifts for C-3 through C-5 were then determined from the HSQC data and the assignments were confirmed by observation of HMBC correlations from H-3 to C-4 and C-5. The methyl protons at 1.27 ppm and the olefinic proton at 5.91 ppm both showed HMBC correlations to a quaternary carbon at 73.6 ppm which was assigned as C-6. The methyl protons (1.27 ppm) were assigned as H-10 and the olefinic proton (5.91 ppm) as H-7. This assignment was confirmed by the observation of HMBC correlations from the methyl protons to both C-5 and a carbon at 145.9 ppm which was assigned as C-7 in addition to the correlation with C-6 mentioned above. H-7 showed COSY correlations with protons at 5.05 and 5.22 ppm allowing assignment of the H-8 protons and C-8 ($\delta_C$ 112.5) was in turn assigned from the HSQC data.

The chemical shift data acquired for the $MT_2$ fragment of Avicin D at AMRI-BRC were very similar to those reported in the literature data for Avicin D and Elliptioside E (Table 4). The only significant difference between the data acquired for Avicin D at AMRI-BRC were the 13C chemical shifts for C-1 and C-2 which appear to be switched with those of $MT_1$ as mentioned above. Also, the $^{13}$C chemical shifts for $MT_2$ C-3 and C-7 are slightly different for Elliptioside E relative to Avicin D which is again likely due to differences in stereochemistry between the Avicins and the Elliptiosides.

Assignment of the $MT_2$ fragment for the metabolite indicated that it was clearly different in structure from that of Avicin D. An HMBC correlation from H-4 of the quinovose residue to the carbonyl at 173.4 ppm allowed assignment of C-1 of the $MT_2$ fragment. Both the methine proton at 2.71 ppm and the methylene protons at 3.86 and 3.93 ppm showed HMBC correlations to C-1. In addition, the methine proton at 2.71 ppm showed COSY correlations with the methylene protons at 3.86 and 3.93 ppm and also with a second methine proton at 4.17 ppm. The HSQC spectrum provided the $^{13}$C chemical shifts for the two methines ($\delta_H$ 2.71/$\delta_C$ 55.9 and $\delta_H$ 4.17/$\delta_C$ 78.1) and the methylene group ($\delta_C$ 62.7). The methine proton at 4.17 ppm showed an HMBC correlation to the methylene carbon at 62.7 ppm. The reciprocal HMBC correlation between the methylene protons and the methine carbon (78.1 ppm) was also observed. These data suggested that the double bond present between C-2 and C-3 in $MT_2$ of Avicin D has been replaced by a four membered oxetane ring formed with the hydroxyl group at C-9 which was confirmed by the assignment of the remainder of the $MT_2$ fragment. The methine proton at 2.71 ppm (H-2) showed an HMBC correlation to a carbon at 30.7 ppm which was assigned as C-4 and the methine proton at 4.17 ppm (H-3) showed a COSY correlation with methylene protons at 1.84 and 2.08 ppm which were assigned as the H-4 protons. The H-4 protons in turn showed COSY correlations with protons at 1.77 and 1.91 ppm which were assigned as H-5 and showed an HMBC correlation with C-3. The methyl group at 1.27 ppm showed HMBC correlations to C-5 and also a quaternary carbon at 84.7 ppm assigned as C-6 and an olefinic carbon at 144.8 ppm assigned as C-7. The HSQC data indicated that the olefinic proton at 5.86 must then be H-7 which showed HMBC correlations with C-5 and C-6 confirming the assignment. COSY correlations between H-7 and the protons at 4.98 and 5.16 ppm allowed assignment of the H-8 protons and C-8 ($\delta_C$ 112.0) was in turn assigned from the HSQC data to complete the assignment of MT2 for the metabolite.

Figure 16A:
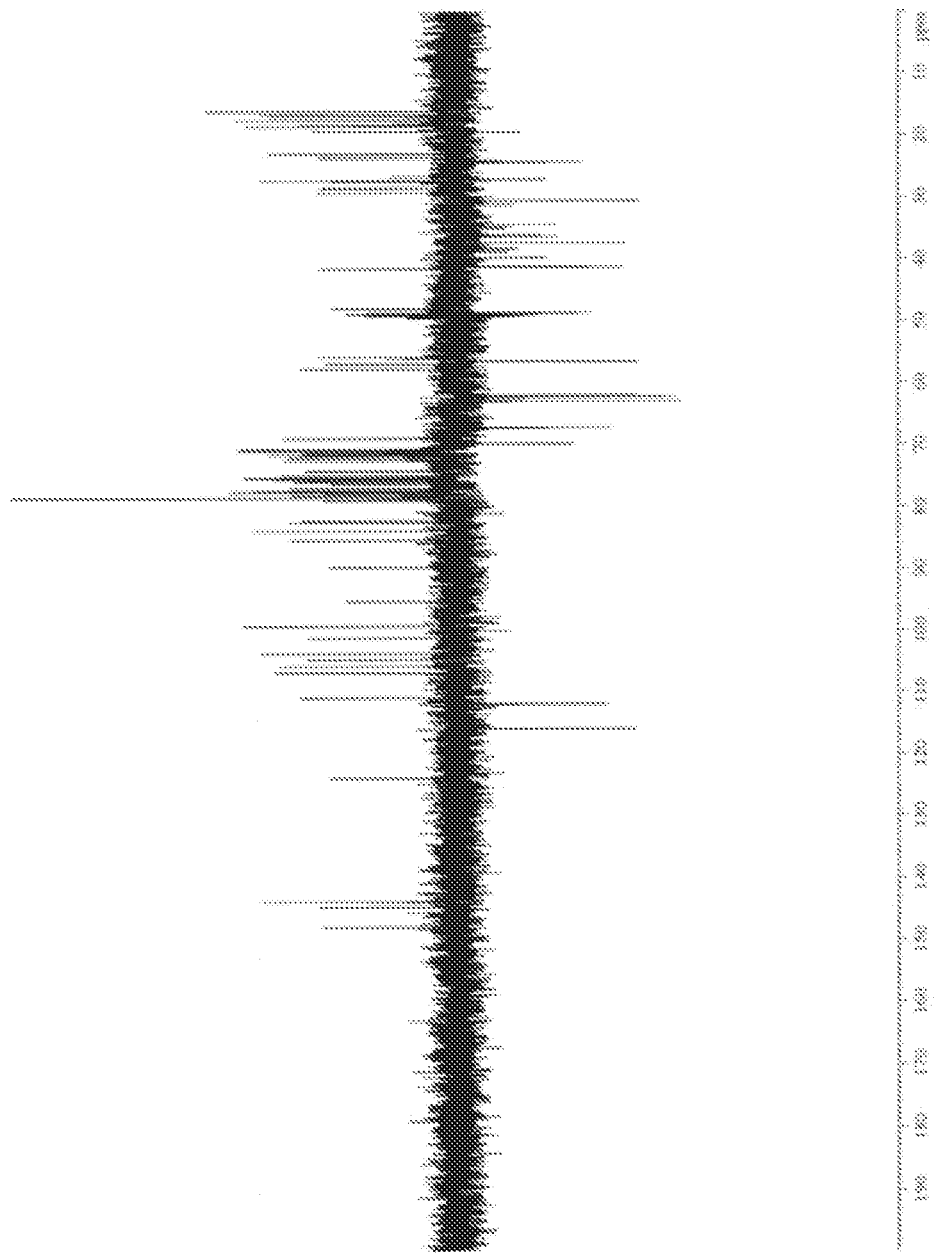
Figure 16C:
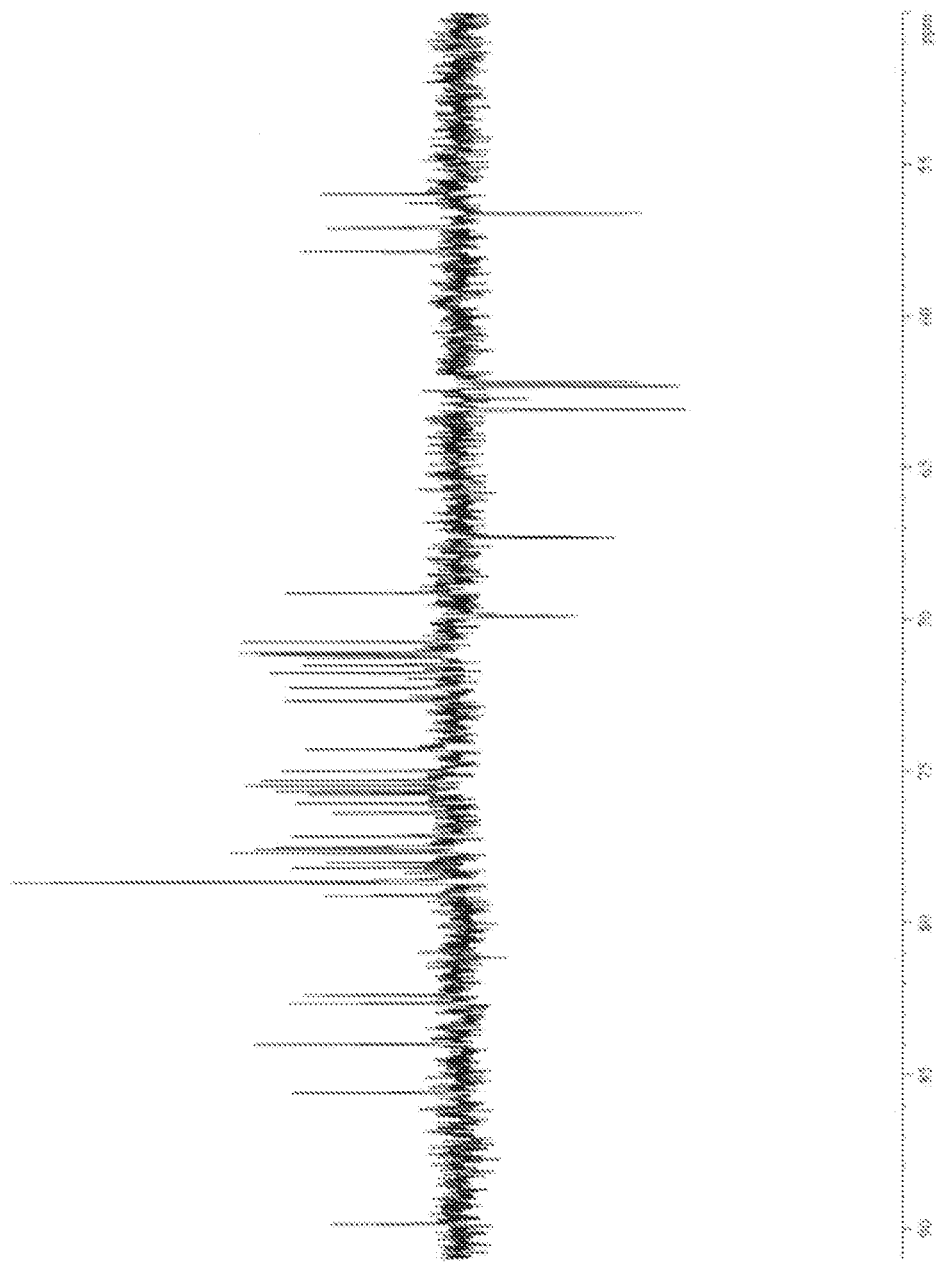
Figure 16D:
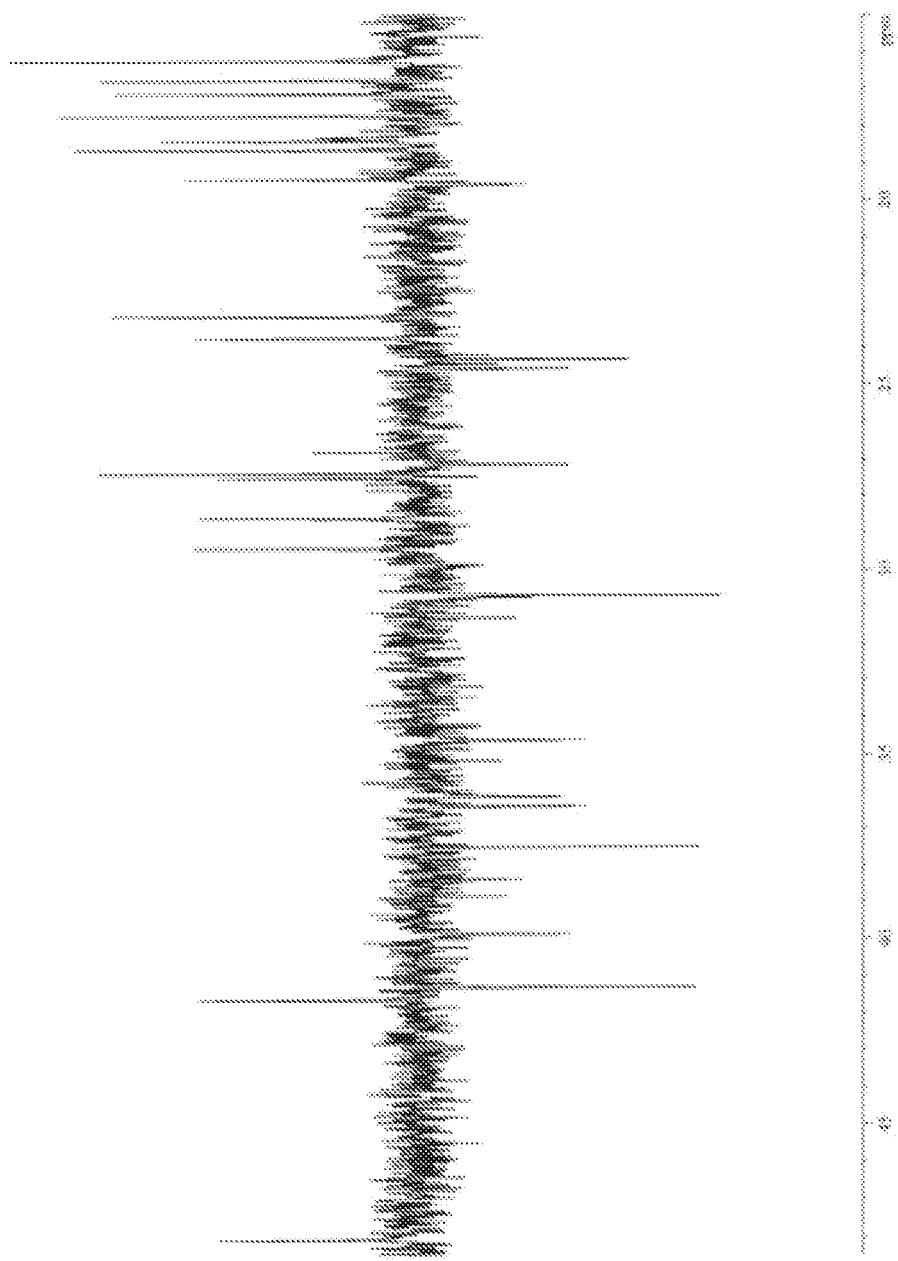
Figure 17A:
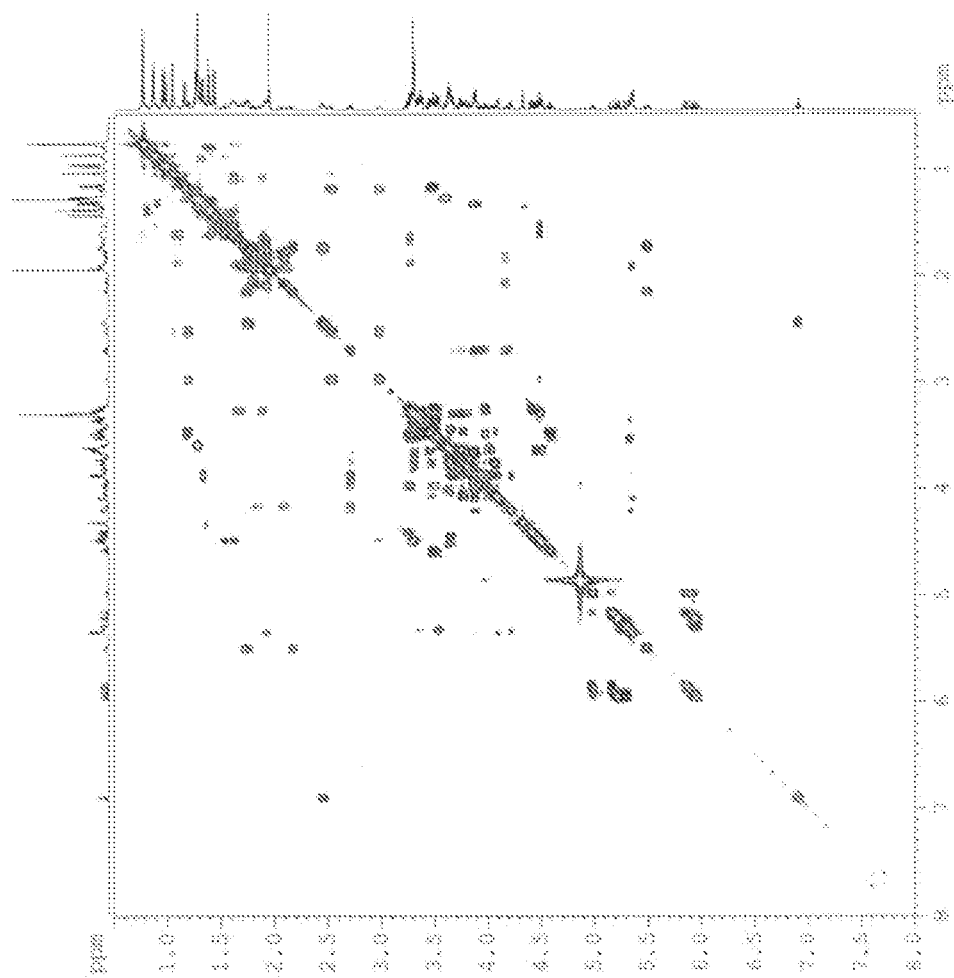
FIGS. 17A-17B are the $^1$H-$^1$H COSY spectra (500 MHz, CD$_3$OD) of Compound 8.
Figure 17B:
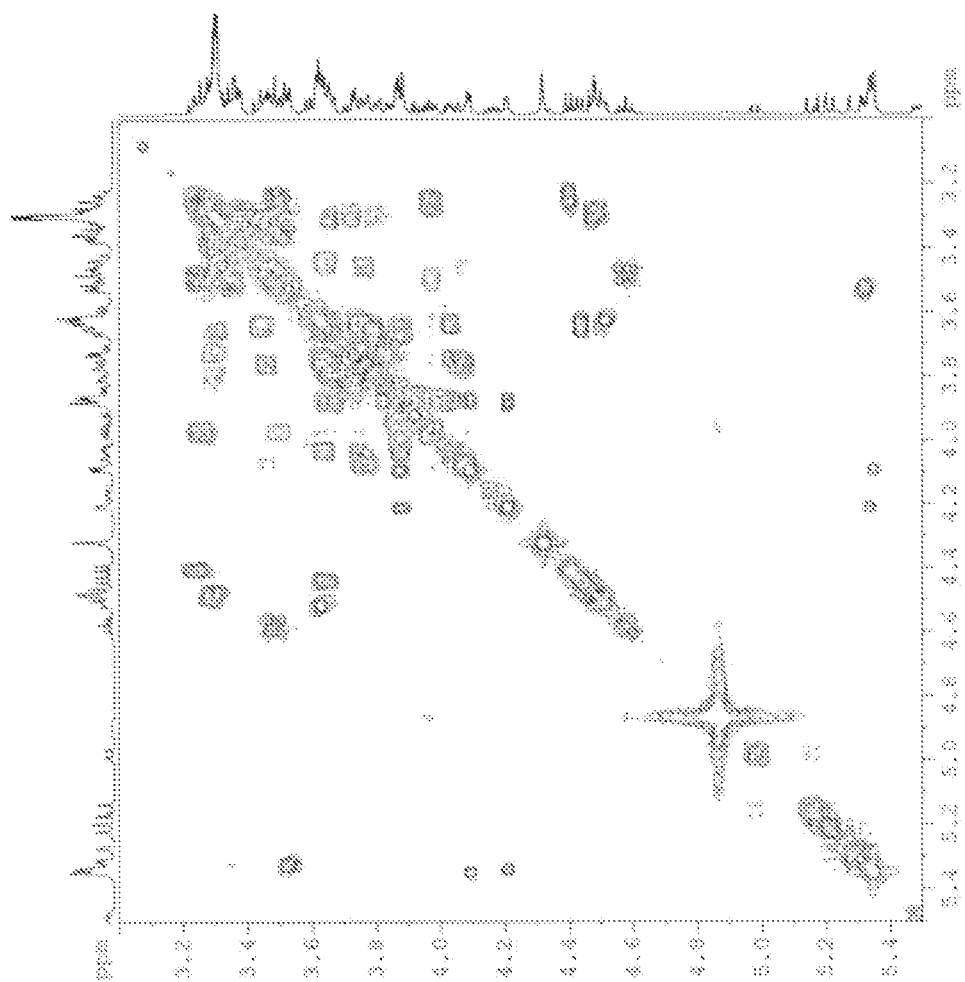
Figure 18A:
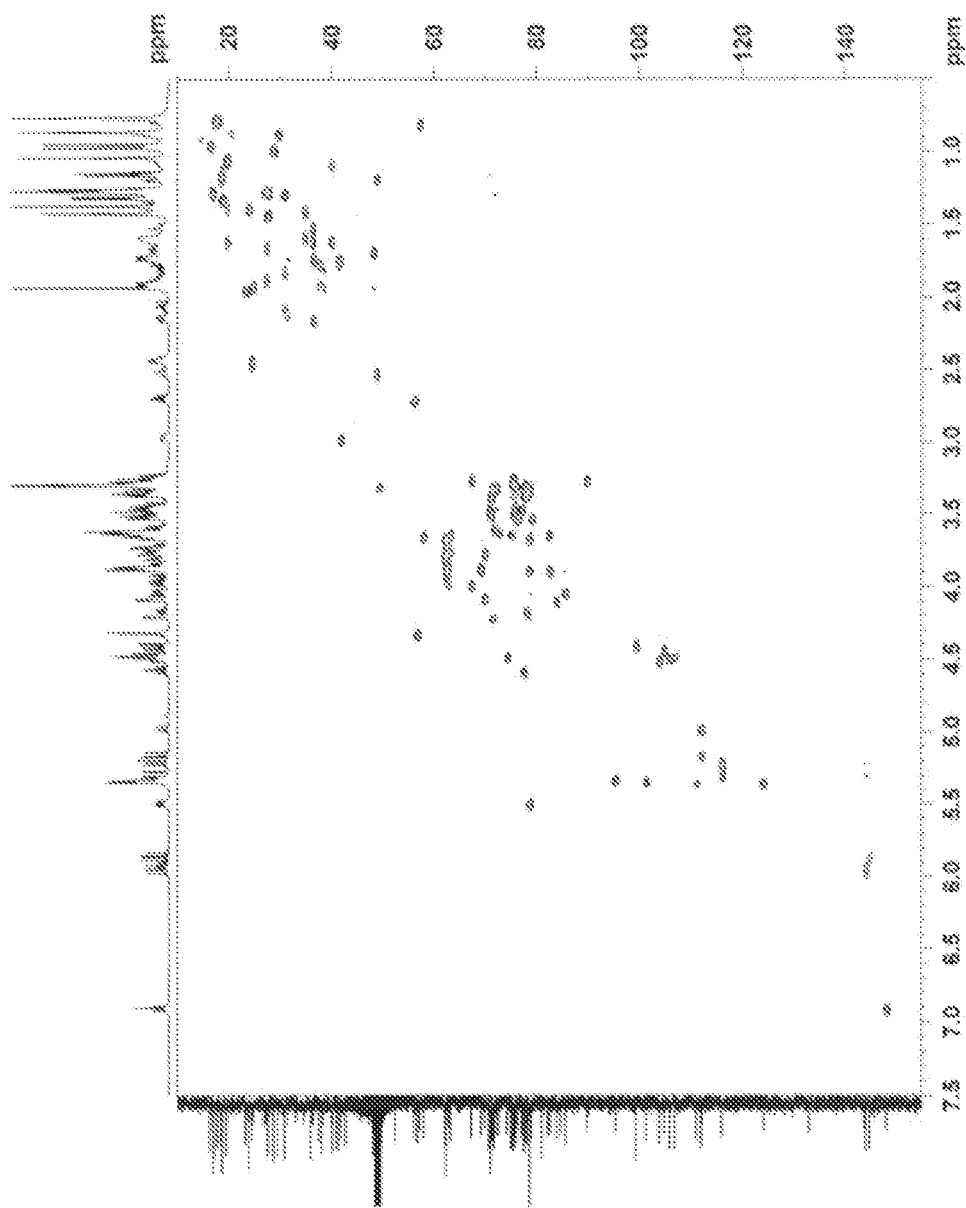
FIGS. 18A-18C are HSQC spectra (500 MHz, CD$_3$OD) of Compound 8.
Figure 18B:
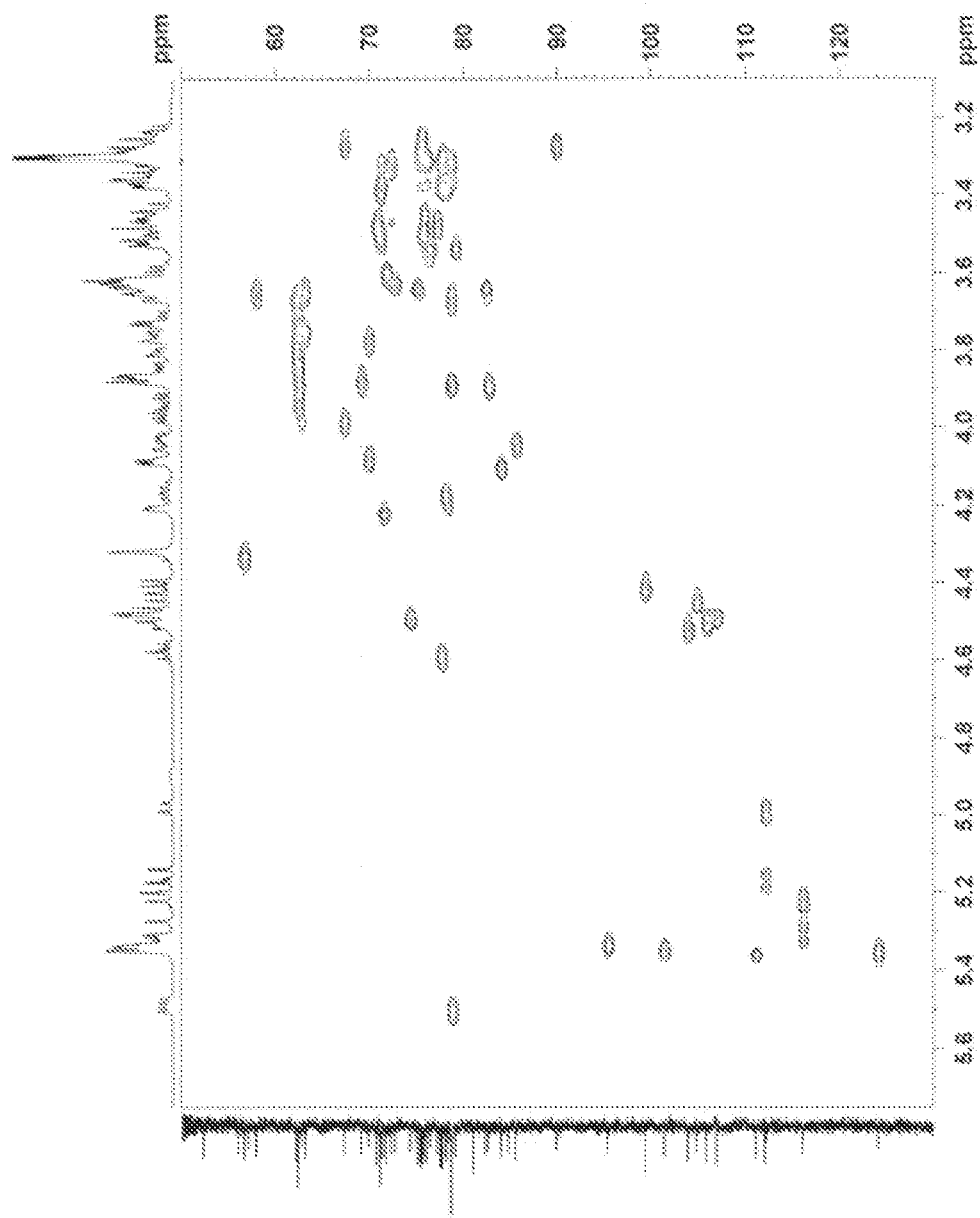
Figure 18C:
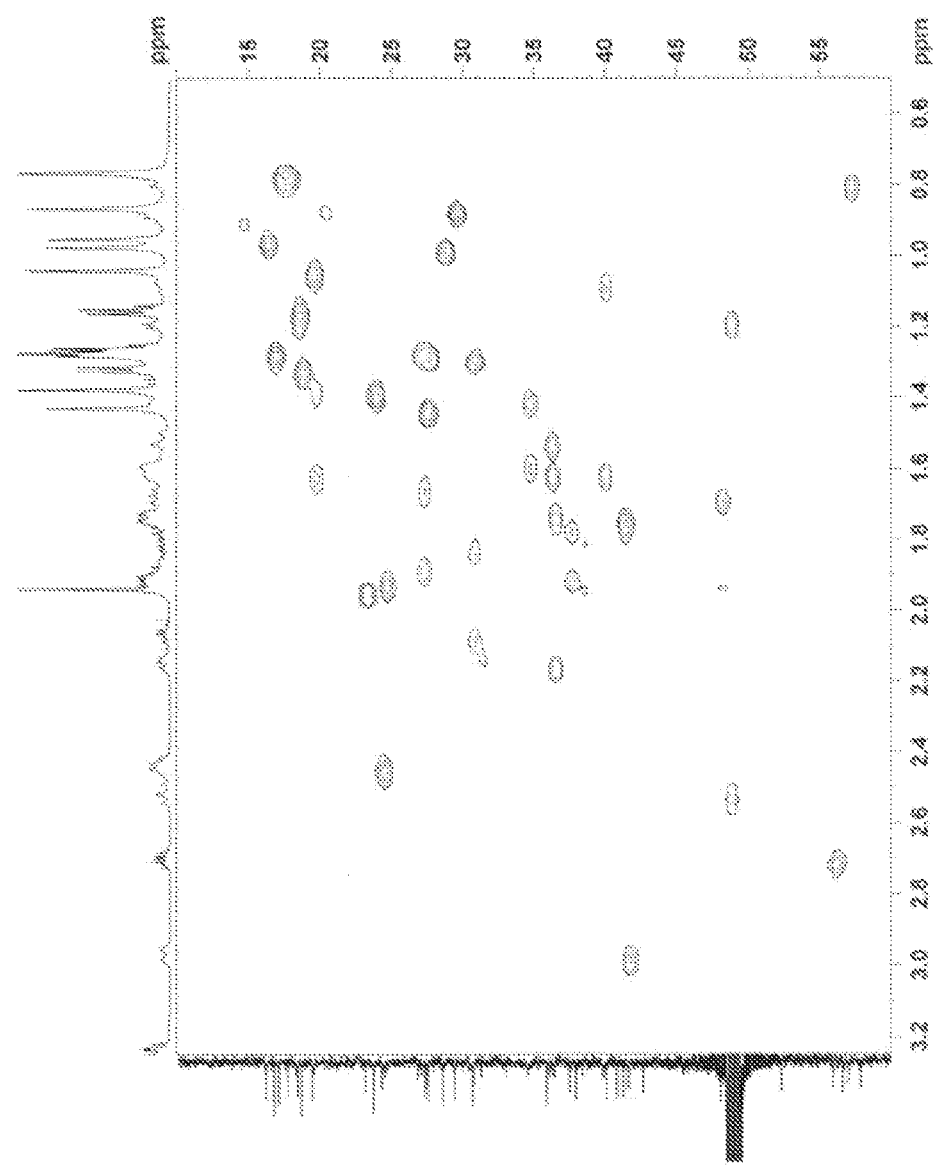
Figure 19B:
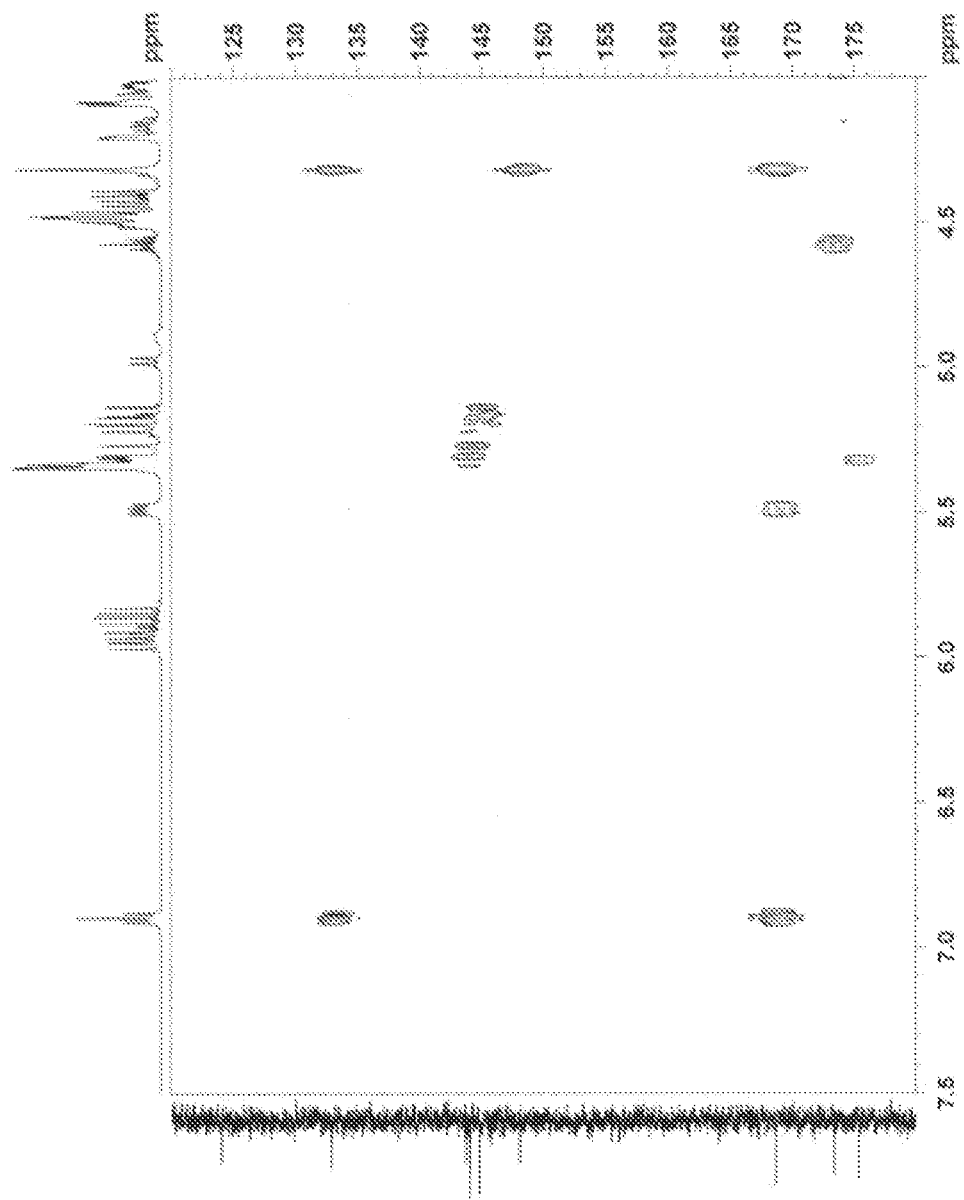
Figure 19C:
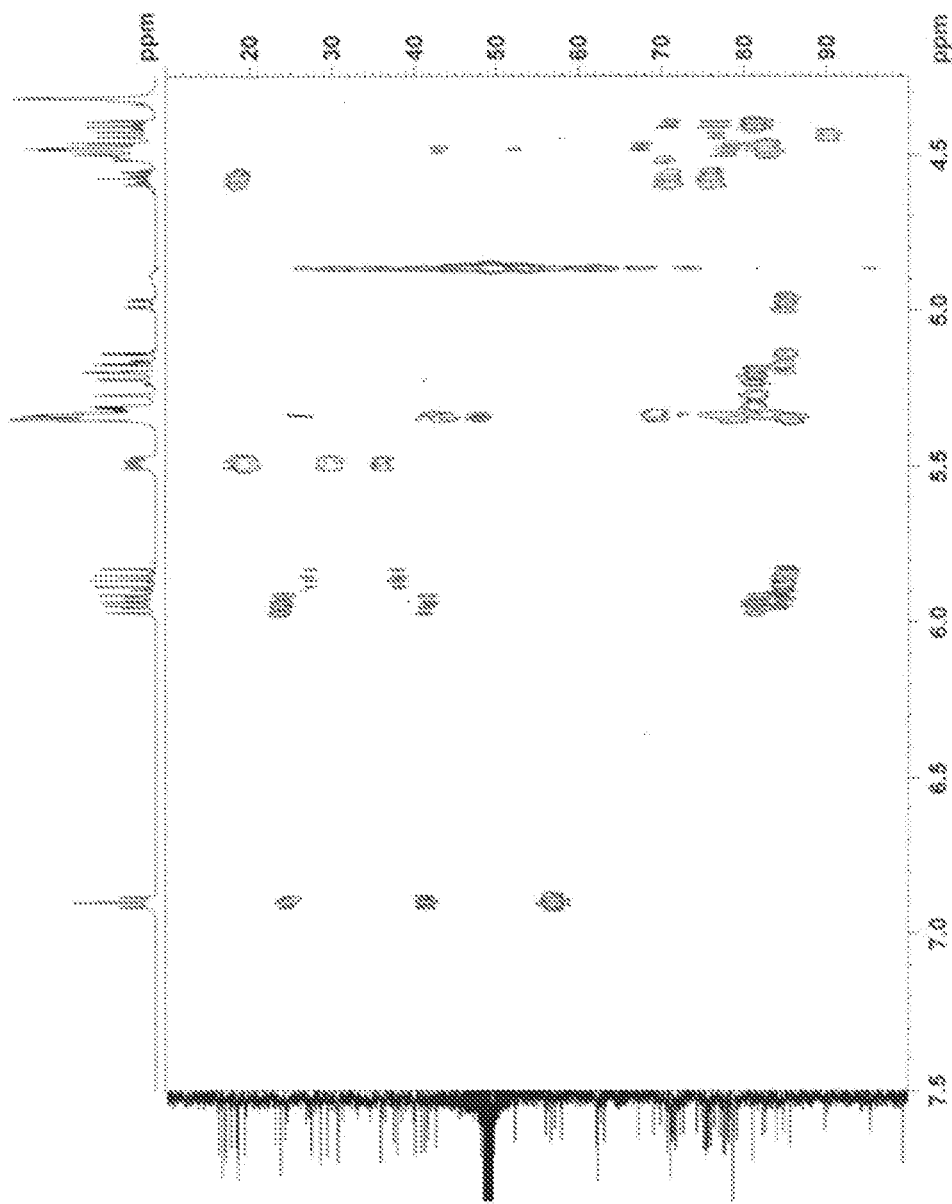
Figure 19D:
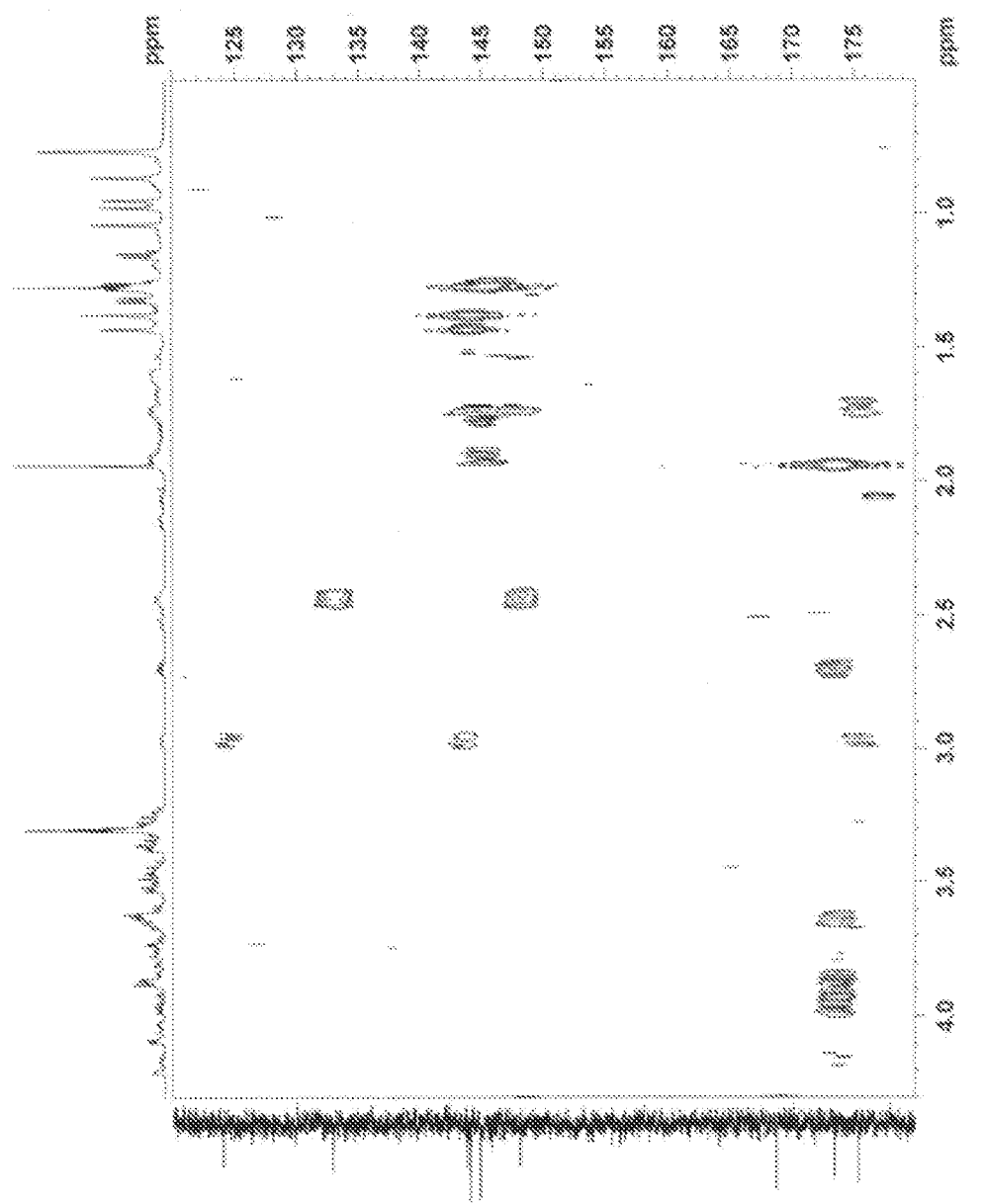
Figure 19E:
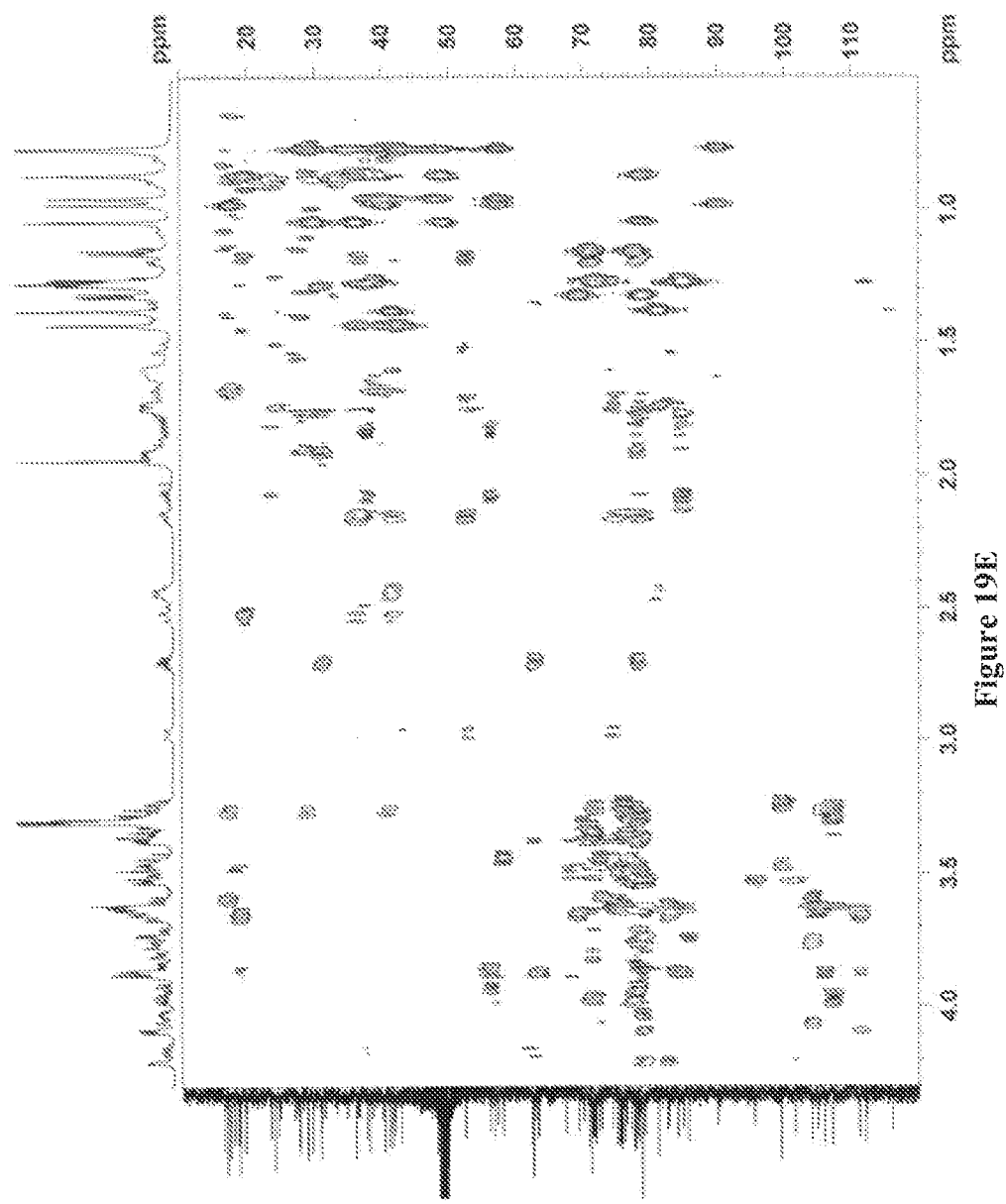
Figure 20A:
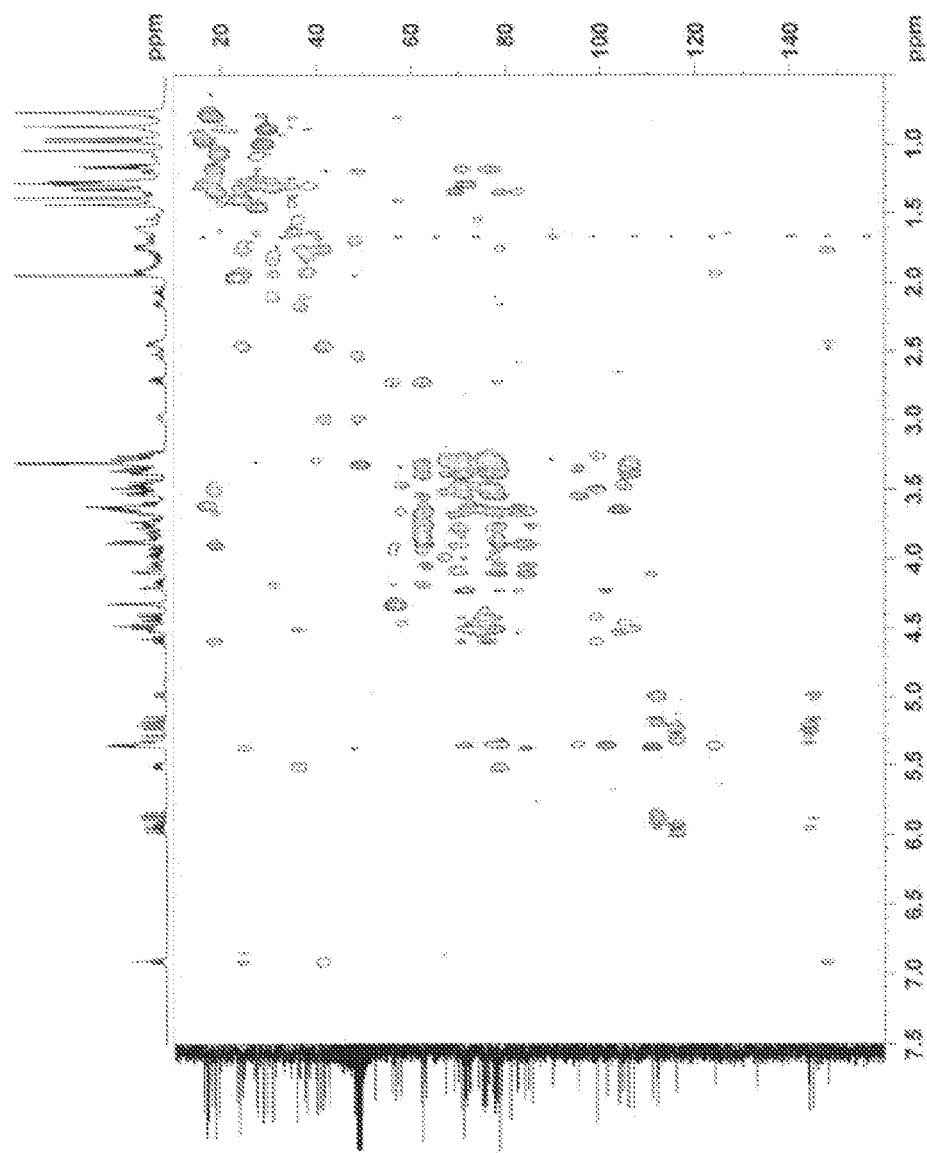
FIGS. 20A-20B are the HSQC-TOCSY spectra (500 MHz, CD$_3$OD) of Compound 8.
Figure 20B:
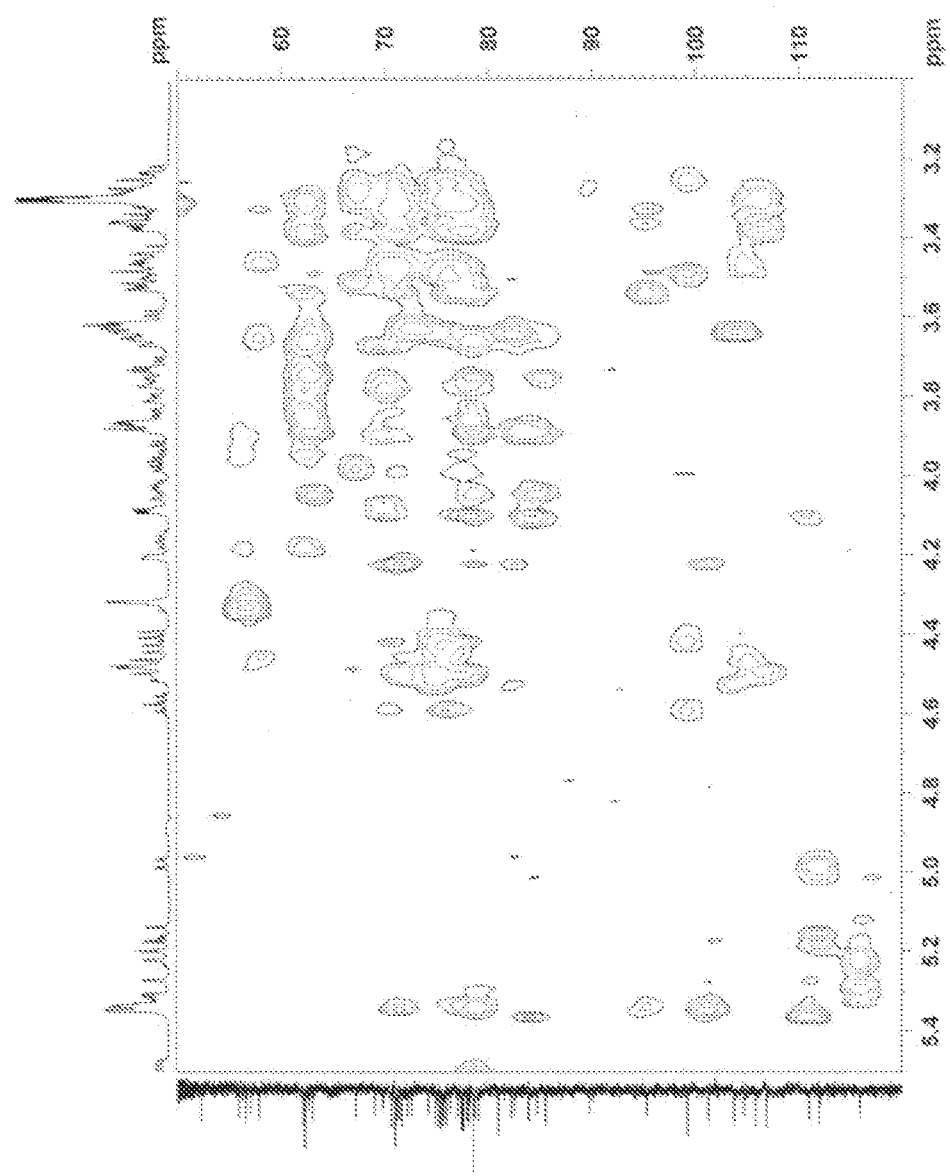

The formation of the oxetane ring leads to the introduction of 2 additional chiral centers in the structure of the metabolite. This leads to four possible diastereomers, two cis-oxetanes and two trans-oxetanes (see FIG. 36). Examination of the multiplets in the $^1$H NMR spectrum corresponding to H-2 and H-3 of the oxetane ring of the $MT_2$ fragment and H-4 of the quinovose moiety of the metabolite indicated the presence of two isomers in an approximately 2:1 ratio (FIG. 16). Further examination of the H-2 multiplet suggested coupling constants of 4.8, 7.8 and 7.8 Hz for the two isomers. This would support a cis-oxetane structure which would show a large coupling constant between H-2 and both H-3 and one of the H-9 protons together with a smaller coupling between H-2 and the H-9 proton on the opposite side of the ring. An attempt was made to further support this by acquisition of 2-D NOESY data for the metabolite. An examination of the 2-D NOESY data showed that although a significant number of correlations were observed for the metabolite structure overall, few correlations were observed for the $MT_2$ fragment. Therefore, the lack of a correlation between H-2 and H-3 does not allow an unambiguous determination. There were also no correlations observed between H-4 of the quinovose moiety and H-2 of the oxetane ring. The data indicate that two isomers of the metabolite are present and suggest that these are the two isomers with the cis-configuration of the oxetane ring.

CONCLUSIONS

Samples of Avicin D and a metabolite of Avicin D, Compound 8 were analyzed by NMR and a complete $^1$H and $^{13}$C assignment was made. Analysis of the data acquired for the metabolite in comparison with that acquired for Avicin D and data available in the literature allowed the structure of the metabolite to be determined. The data further indicated that the metabolite was present as a mixture of isomers. The observed coupling constants suggest that the mixture constants of the two diastereomers which have the cis-configuration at the oxetane ring.

Example 2

Comparison of the Cytoxicity of Avicin D Oxetane (Compound 8) with Avicin D

The $IC_{50}$ of the oxetane derivative of Avicin D (Compound 8, shown in FIG. 5), was compared to the $IC_{50}$ of Avicin D in 34 different cell lines. The assay results are summarized in Table 5 below.

The growth inhibitory effects of avicin D and oxetane derivative were measured using the MTT [3-(4,5-dimethylthiazol-2-yl)-2,5-diphenyl tetrazolium bromide] reduction assay as described in Haridas et al. (2001). Cells were cultured with varying concentrations of avicin D or oxetane in 96-well plates for 72 hrs at 37° C. At the end of 72 hrs, cells were stained with MTT for 2 hrs and then incubated with lysis buffer (20% SDS in 50% N,N-dimethylformamide) for another 6 hrs. Optical density at 570 nm was used as a measure of cell viability.

TABLE 5

Summary of Activity of Avicin D and Compound 8

| IC50 (uM) Avicin D | Cell Line | IC50 (uM) Compound 8 |
|---|---|---|
| 0.36 | 769P | 0.15 |
| 0.44 | A498 | 0.22 |
| 6.90 | A549 | 1.20 |
| 0.66 | B16F10 | 0.14 |
| 2.80 | BT474 | 0.90 |
| 1.10 | BT474 M1 | 0.70 |
| 4.80 | BT549 | 1.40 |
| 1.12 | CAKI-1 | 0.28 |
| 2.06 | CAKI-2 | 0.49 |
| 5.50 | CCRF-CEM | 0.63 |
| 13.20 | Hela | 1.87 |
| 0.44 | HepG2 | 0.31 |
| 0.42 | JEKO-1 | 0.16 |
| 0.17 | Jurkat | 0.09 |
| 0.47 | LnCAP | 0.19 |
| 15.20 | MCF7 | 2.60 |
| 0.42 | MINO | 0.06 |
| 0.10 | MM1 | 0.03 |
| 0.32 | MOLT4 | 0.20 |
| 1.30 | OVCAR3 | 0.21 |
| 0.52 | Panc-1 | 0.31 |
| 0.44 | PC3 | 0.19 |
| 1.27 | Raji | 0.62 |
| 0.31 | RL | 0.08 |
| 0.30 | RPMI 8226 | 0.16 |
| 1.00 | SKOV3 | 0.42 |
| 4.40 | U2OS | 1.20 |
| 0.30 | U266 | 0.08 |
| 0.52 | WSU-DLCL2 | 0.14 |
| 0.67 | ZR751 | 0.34 |
| 3.80 | 3T3 L1 | 0.80 |
| 30.10 | GM0131 | 12.00 |
| 6.50 | HEK293 | 6.80 |
| 6.10 | HS27 | 2.50 |

The cell lines 769P, A498, CAKI-1, and CAKI-2 are derived from primary human renal-cell cancers (RCC). A549 is a human lung adenocarcinoma epithelial cell line. B16F10 is a mouse melanoma cell line. BT474, BT 474 M1, BT549, MCF7, MINO, and ZR751 are breast cancer cell lines. CCRF-CEM, Jurkat, and MOLT4 are leukemia cell lines. HELA is cell line derived from cervical caner. HepG2 is a human hepatocellular liver carcinoma cell line. JeKo-1 is a mantle cell lymphoma (MCL) cell line. LnCAP is a cell line was established from a metastatic lesion of human prostatic adenocarcinoma. MM.1 and RPMI-8226 are human multiple myeloma cell lines. OVCAR3 and SKOV3 are ovarian cancer cell lines. Panc-1 is a pancreatic cancer cell line. PC3 is a prostate cancer cell line. Raji is a Burkitt's lymphoma cell line. RL is a non-Hodgkin's lymphoma cell line. U2OS is a human osteosarcoma cell line. U266 is a myeloma cell line. WSU-DLCL2 is a human diffuse large cell lymphoma cell line. 3T3 LI is a fibroblast cell line. GM0131 is a wild type human fibroblast cell line. HEK293 is a human embryonic kidney cell line. Hs27 cells is a human foreskin fibroblast cell line.

The $IC_{50}$ for the oxetane derivative was lower for all cell lines tested except HEK293.

Example 3

Comparison of Nrf2 Activation of Avicin D Oxetane (Compound 8) with Avicin D

Nrf2, a master regulator of the antioxidant response, has been shown to play a key role in the amelioration of oxidative stress. Activation of Nrf2 is believed to be beneficial in some diseases such as Parkinson's disease where the underlying cause is oxidative stress. However, in cancer, recent studies have suggested that activation of the Nrf2 pathway could confer a protective effect to the tumor cells by reducing the oxidative stress. The decreased ability of Compound 8 to activate Nrf2 along with its increased cytotoxic effect is consistent with improved anti-cancer potential compared to Avicin D. The Nrf2 activation results and $IC_{50}$ values are summarized in Table 6.

Activation of Nrf2 was assessed by measuring the antioxidant response element (ARE)-mediated gene expression as described previously by Haridas et al., 2004, which is incorporated herein by reference. Briefly, ARE is a cis-acting regulatory sequence identified in the promoter region of several genes encoding phase 2 detoxification enzymes, that binds to Nrf2. Hep G2 (human hepatocarcinoma) cells were transfected with a human ARE-driven luciferase (luc) containing plasmid, hARE-luc. Following exposure to avicin D/compound 8, the luciferase activity induced in these cells was measured using a dual-luciferase assay kit (Promega) according to the manufacturer's protocol.

The IC50 values indicate the concentrations of avicin D/compound 8 required to induce a 50% reduction in call viability. These studies were done in Jurkat (human T-cell leukemia) cells and have been described previously in Haridas et al., 2001, which is incorporated herein by reference.

TABLE 6

Summary of Activity of Avicin D and Compound 8

| Compound | Fold Nrf2 activation | $IC_{50}$ (μM) |
|---|---|---|
| Avicin D | 2.10 | 0.18 |
| Compound 8/X-20/Oxetane | 0.98 | 0.04 |

Example 4

Comparison of Avicin D Oxetane (Compound 8) with Avicin D Cytotoxicity in Cancer Stem Cell Model Human mammary epithelial cells were transfected with transcription factor TWIST acquiring mesenchymal stem cell-like traits, including the ability to form mammospheres. See Cano et al., 2000; Yang et al., Cell, 2004; Mani et al., 2008, which are all incorporated herein by reference.

HMLE cells expressing TWIST were plated at 100 cells/ 0.1 ml in 96-well plates. The cells were cultured in MEGM media supplemented with 20 ng/mL bFGF, 10 ng/mL EGF, 4 ug/mL heparin, and 1% methyl cellulose. Formation of spheres could be seen around day 7. Avicin D/Compound 8 (60 nM) was first added to the cultures on day 7 and subsequently every $7^{th}$ day. Shown are the representative images (10× magnification) of the mammospheres from untreated and avicinD/Compound 8 treated cultures, as seen on day 21. Both Avicin D and Compound 8 appear to inhibit the development of these spheres as measured by the size of these spheres. See FIGS. 6A-D, which show mammospheres treated with 60 nM of Avicin D or Compound 8 for fourteen days. The ability of these agents to induce cell kill in both the tumor cell population as well as the stem-like cells enhances their potential for use as a cancer therapy.

REFERENCES

The following references to the extent that they provide exemplary procedural or other details supplementary to those set forth herein, are specifically incorporated herein by reference.

U.S. Pat. No. 6,444,233
Beutler et. al. *Bioorg. Med. Chem.* 5:1509-1517, 1997.
Cano et al., Nat. Cell Biol., 2:76-83, 2000.
Cao, et. al. *J. Nat. Prod.* 70:361-366, 2007.
Gonda, In: *Critical Reviews in Therapeutic Drug Carrier Systems,* 6:273-313, 1990.
*Handbook of Pharmaceutical Salts: Properties, and Use,* Stahl and Wermuth (Eds.), Verlag Helvetica Chimica Acta, 2002.
Haridas et al., *J. Clin. Invest.,* 113(1):65-73, 2004.
Haridas et al., *Proc. Natl. Acad. Sci. USA,* 98:5821-5826, 2001.
Jayatilake, et. al. *J. Nat. Prod.* 66:779-783, 2003.
Larock, *Comprehensive Organic Transformations,* $2^{nd}$ Ed., Wiley-VCH, 1999.
*March's Advanced Organic Chemistry: Reactions, Mechanisms, and Structure,* 2007.
Mani et al., *Cell,* 133:704-15, 2008.
Patton and Platz, *Adv. Drug Del. Rev.,* 8:179-196, 1992.
*Pharmaceutical dosage form tablets,* Liberman et. al. (Eds.), NY, Marcel Dekker, Inc., 1989.
*Pharmaceutical dosage forms and drug delivery systems,* $6^{th}$ Ed., Ansel et al. (Eds.), Media, Pa., Williams and Wilkins, 1995.
Remington—*The science and practice of pharmacy,* $20^{th}$ Ed., Jennaro et. al. (Eds.), Phila, Lippencott, Williams, and Wilkens, 2000.
Reya et al., *Nature,* 414:111-15, 2001.
Yang et al., *Cell,* 117:927-939, 2004.

What is claimed is:
1. A compound of the formula:

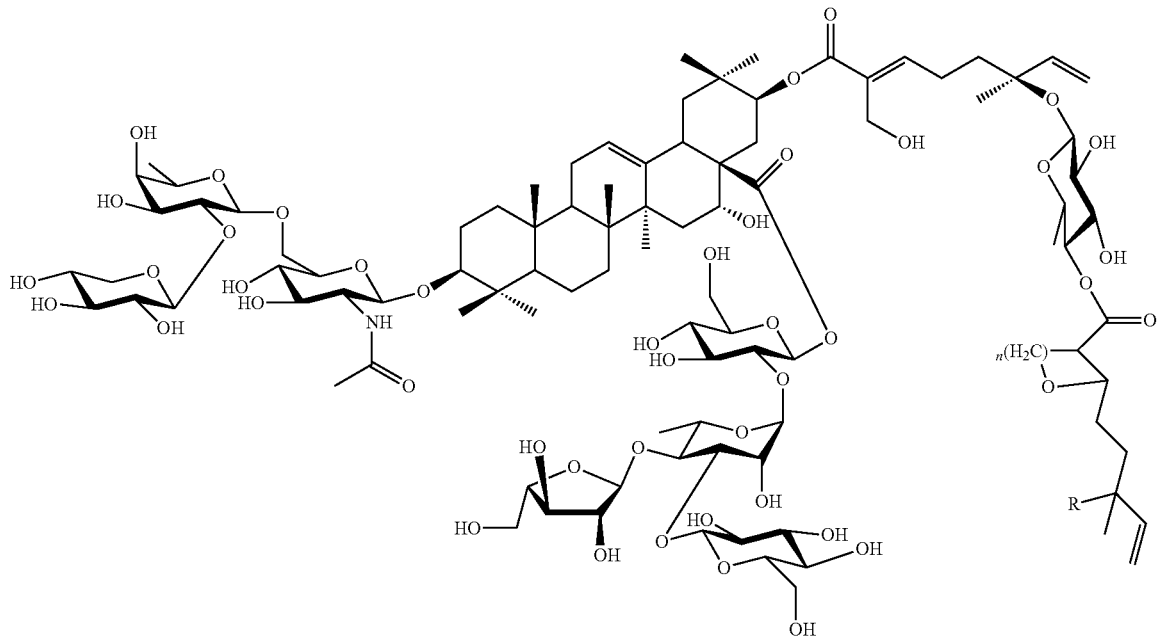

wherein:
  n is 0-3, and
  R is —H or —OH;
or a pharmaceutically acceptable salt, acetal, ketal or tautomer thereof.

2. The compound of claim 1, further defined as:

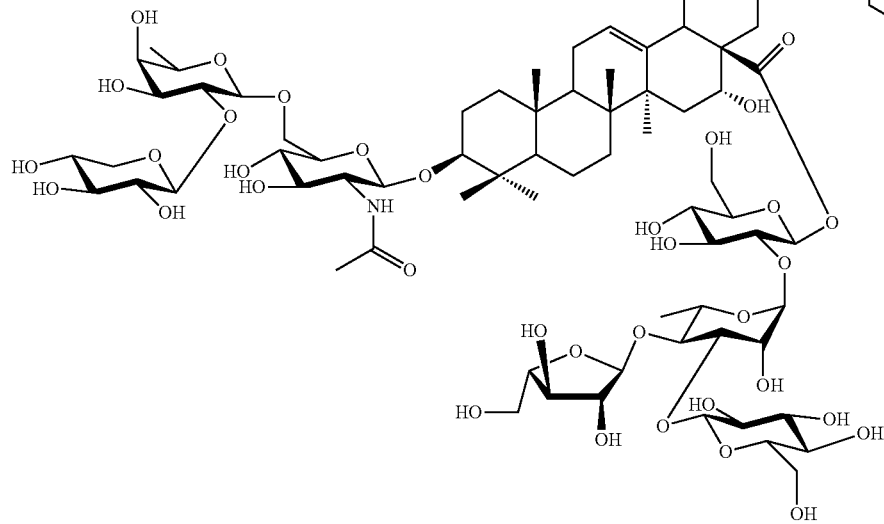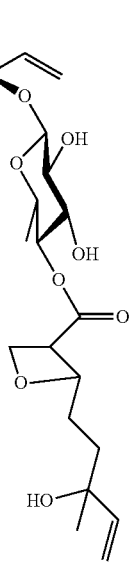

or a pharmaceutically acceptable salt, acetal, ketal or tautomer thereof.

3. A pharmaceutical composition comprising the compound according to claim 2 and a pharmaceutically acceptable carrier.

4. The pharmaceutical composition of claim 3, wherein the composition is formulated for oral administration.

5. The pharmaceutical composition of claim 3, further comprising one or more pharmaceutically acceptable excipients.

6. The pharmaceutical composition of claim 3, wherein the composition is formulated for controlled release.

7. A method of treating a proliferative disorder, the method comprising administering to a patient in need thereof an effective amount of the compound according to claim 2.

8. The method of claim 7, wherein the proliferative disorder is cancer.

* * * * *